(12) United States Patent
Reich et al.

(10) Patent No.: US 9,011,530 B2
(45) Date of Patent: Apr. 21, 2015

(54) PARTIALLY-ADJUSTABLE ANNULOPLASTY STRUCTURE

(75) Inventors: Tal Reich, Binyamina (IL); Tal Hammer, Ramat Gan (IL); Uriel Aba Pomerantz, Kfar Sava (IL); Oz Cabiri, Macabim-Reut (IL)

(73) Assignee: Valtech Cardio, Ltd., Or Yehuda (IL)

( * ) Notice: Subject to any disclaimer, the term of this patent is extended or adjusted under 35 U.S.C. 154(b) by 0 days.

(21) Appl. No.: 13/167,444

(22) Filed: Jun. 23, 2011

(65) Prior Publication Data

US 2012/0022644 A1  Jan. 26, 2012

Related U.S. Application Data

(63) Continuation-in-part of application No. 12/341,960, filed on Dec. 22, 2008, now Pat. No. 8,241,351.

(51) Int. Cl.
*A61F 2/24* (2006.01)
*A61B 17/072* (2006.01)
*A61B 17/068* (2006.01)
*A61B 17/00* (2006.01)
*A61B 17/064* (2006.01)

(52) U.S. Cl.
CPC ............. *A61F 2/2445* (2013.01); *A61F 2/2448* (2013.01); *A61B 17/072* (2013.01); *A61B 2017/00243* (2013.01); *A61B 2017/003* (2013.01); *A61B 2017/0649* (2013.01); *A61F 2/2466* (2013.01); *A61F 2250/0004* (2013.01); *A61B 17/068* (2013.01)

(58) Field of Classification Search
CPC .................................................... A61F 2/2448
USPC ......................................................... 623/2.37
See application file for complete search history.

(56) References Cited

U.S. PATENT DOCUMENTS

| 3,604,488 | A | 9/1971 | Wishart et al. |
|---|---|---|---|
| 3,656,185 | A | 4/1972 | Carpentier |
| 4,042,979 | A | 8/1977 | Angell |
| 4,118,805 | A | 10/1978 | Reimels |
| 4,434,828 | A | 3/1984 | Trincia |
| 4,602,911 | A | 7/1986 | Ahmadi et al. |
| 4,625,727 | A | 12/1986 | Leiboff |

(Continued)

FOREIGN PATENT DOCUMENTS

| WO | 92/05093 | 4/1992 |
|---|---|---|
| WO | 01/26586 | 4/2001 |

(Continued)

OTHER PUBLICATIONS

O'Reilly S et al., "Heart valve surgery pushes the envelope," Medtech Insight 8(3): 73, 99-108 (2006).
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Swain CP et al., "An endoscopically deliverable tissue-transfixing device for securing biosensors in the gastrointestinal tract," Gastrointestinal Endoscopy 40(6): 730-734 (1994).
Odell JA et al., "Early Results of a Simplified Method of Mitral Valve Annuloplasty," Circulation 92:150-154 (1995).

(Continued)

*Primary Examiner* — Jacqueline Woznicki
(74) *Attorney, Agent, or Firm* — Sughrue Mion, PLLC

(57) ABSTRACT

Apparatus and methods are described including an annuloplasty structure configured for implantation along an annulus of an atrioventricular valve of a heart of a subject. The structure includes a coiled element comprising at least one first portion thereof which is flexible and longitudinally compressible, and at least one second portion thereof in series with the first portion, the second portion being flexible and less longitudinally compressible than the first portion. Other applications are also described.

21 Claims, 23 Drawing Sheets

(56) References Cited

U.S. PATENT DOCUMENTS

| | | | |
|---|---|---|---|
| 4,778,468 A | 10/1988 | Hunt et al. |
| 4,917,698 A | 4/1990 | Carpentier et al. |
| 5,061,277 A | 10/1991 | Carpentier et al. |
| 5,104,407 A | 4/1992 | Lam et al. |
| 5,108,420 A | 4/1992 | Marks |
| 5,300,034 A | 4/1994 | Behnke et al. |
| 5,306,296 A | 4/1994 | Wright |
| 5,450,860 A | 9/1995 | O'Connor |
| 5,477,856 A | 12/1995 | Lundquist |
| 5,593,424 A | 1/1997 | Northrup III |
| 5,669,919 A | 9/1997 | Sanders et al. |
| 5,674,279 A | 10/1997 | Wright et al. |
| 5,810,882 A | 9/1998 | Bolduc |
| 5,843,120 A | 12/1998 | Israel et al. |
| 5,855,614 A | 1/1999 | Stevens et al. |
| 5,876,373 A | 3/1999 | Giba et al. |
| 5,961,440 A | 10/1999 | Schweich et al. |
| 5,961,539 A | 10/1999 | Northrup, III et al. |
| 6,045,497 A | 4/2000 | Schweich et al. |
| 6,050,936 A | 4/2000 | Schweich et al. |
| 6,059,715 A | 5/2000 | Schweich et al. |
| 6,074,401 A | 6/2000 | Gardiner et al. |
| 6,102,945 A | 8/2000 | Campbell |
| 6,143,024 A | 11/2000 | Campbell |
| 6,165,119 A | 12/2000 | Schweich et al. |
| 6,183,411 B1 | 2/2001 | Mortier |
| 6,187,040 B1 | 2/2001 | Wright |
| 6,217,610 B1 | 4/2001 | Carpentier et al. |
| 6,231,602 B1 | 5/2001 | Carpentier |
| 6,251,092 B1 | 6/2001 | Qin et al. |
| 6,319,281 B1 | 11/2001 | Patel |
| 6,332,893 B1 | 12/2001 | Mortier et al. |
| 6,402,780 B2 | 6/2002 | Williamson, IV |
| 6,406,420 B1 | 6/2002 | McCarthy et al. |
| 6,419,696 B1 * | 7/2002 | Ortiz et al. ............... 623/2.37 |
| 6,451,054 B1 | 9/2002 | Stevens |
| 6,470,892 B1 | 10/2002 | Forsell |
| 6,524,338 B1 | 2/2003 | Gundry |
| 6,537,314 B2 | 3/2003 | Langberg et al. |
| 6,547,801 B1 | 4/2003 | Dargent |
| 6,564,805 B2 | 5/2003 | Garrison et al. |
| 6,569,198 B1 | 5/2003 | Wilson |
| 6,579,297 B2 | 6/2003 | Bicek et al. |
| 6,589,160 B2 | 7/2003 | Schweich et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | Dell et al. |
| 6,629,921 B1 | 10/2003 | Schweich et al. |
| 6,651,671 B1 | 11/2003 | Donlon et al. |
| 6,652,556 B1 | 11/2003 | VanTasel |
| 6,682,558 B2 | 1/2004 | Tu et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,709,456 B2 | 3/2004 | Langberg et al. |
| 6,718,985 B2 | 4/2004 | Hlavka et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,510 B2 | 7/2004 | Vidlund |
| 6,786,924 B2 | 9/2004 | Ryan |
| 6,797,002 B2 | 9/2004 | Spence et al. |
| 6,802,319 B2 | 10/2004 | Gifford, III et al. |
| 6,805,710 B2 | 10/2004 | Bolling et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,986,775 B2 | 1/2006 | Morales et al. |
| 6,989,028 B2 | 1/2006 | Lashinski et al. |
| 7,004,176 B2 | 2/2006 | Lau |
| 7,011,669 B2 | 3/2006 | Kimblad |
| 7,011,682 B2 | 3/2006 | Lashinski et al. |
| 7,037,334 B1 | 5/2006 | Hlavka et al. |
| 7,077,862 B2 | 7/2006 | Vidlund |
| 7,087,064 B1 | 8/2006 | Hyde |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,150,737 B2 | 12/2006 | Purdy et al. |
| 7,159,593 B2 | 1/2007 | McCarthy |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,189,199 B2 | 3/2007 | McCarthy et al. |
| 7,226,467 B2 | 6/2007 | Lucatero et al. |
| 7,238,191 B2 | 7/2007 | Bachmann |
| 7,294,148 B2 | 11/2007 | McCarthy |
| 7,297,150 B2 | 11/2007 | Cartledge et al. |
| 7,311,728 B2 | 12/2007 | Solem et al. |
| 7,316,710 B1 | 1/2008 | Cheng et al. |
| 7,329,280 B2 | 2/2008 | Bolling et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,452,376 B2 | 11/2008 | Lim et al. |
| 7,455,690 B2 | 11/2008 | Cartledge et al. |
| 7,507,252 B2 | 3/2009 | Lashinski et al. |
| 7,530,995 B2 | 5/2009 | Quijano |
| 7,549,983 B2 | 6/2009 | Roue |
| 7,563,267 B2 | 7/2009 | Goldfarb et al. |
| 7,563,273 B2 | 7/2009 | Goldfarb et al. |
| 7,588,582 B2 | 9/2009 | Starksen et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,753,924 B2 | 7/2010 | Starksen et al. |
| 7,992,567 B2 | 8/2011 | Hirotsuka |
| 7,993,368 B2 | 8/2011 | Gambale et al. |
| 8,070,804 B2 | 12/2011 | Hyde |
| 8,123,800 B2 | 2/2012 | McCarthy |
| 8,142,495 B2 | 3/2012 | Hasenkam |
| 8,147,542 B2 | 4/2012 | Maisano |
| 8,152,844 B2 | 4/2012 | Rao |
| 8,226,711 B2 | 7/2012 | Mortier |
| 8,241,351 B2 | 8/2012 | Cabiri |
| 8,252,050 B2 | 8/2012 | Maisano |
| 8,287,591 B2 | 10/2012 | Keidar |
| 8,353,956 B2 | 1/2013 | Miller |
| 8,523,940 B2 | 9/2013 | Richardson |
| 2001/0021874 A1 | 9/2001 | Carpentier |
| 2002/0042621 A1 | 4/2002 | Liddicoat |
| 2002/0087048 A1 | 7/2002 | Brock et al. |
| 2002/0103532 A1 | 8/2002 | Langberg |
| 2002/0151961 A1 | 10/2002 | Lashinski |
| 2002/0173841 A1 | 11/2002 | Ortiz et al. |
| 2002/0177904 A1 | 11/2002 | Huxel et al. |
| 2003/0018358 A1 | 1/2003 | Saadat |
| 2003/0050693 A1 | 3/2003 | Quijano et al. |
| 2003/0078465 A1 | 4/2003 | Pai et al. |
| 2003/0105519 A1 | 6/2003 | Fasol et al. |
| 2003/0167062 A1 | 9/2003 | Gambale et al. |
| 2003/0191528 A1 | 10/2003 | Quijano et al. |
| 2003/0199974 A1 | 10/2003 | Lee et al. |
| 2003/0229350 A1 | 12/2003 | Kay |
| 2003/0229395 A1 | 12/2003 | Cox |

(56) References Cited

U.S. PATENT DOCUMENTS

| | | |
|---|---|---|
| 2003/0233142 A1 | 12/2003 | Morales |
| 2004/0019377 A1 | 1/2004 | Taylor |
| 2004/0024451 A1 | 2/2004 | Johnson et al. |
| 2004/0039442 A1 | 2/2004 | St. Goar et al. |
| 2004/0049207 A1 | 3/2004 | Goldfarb et al. |
| 2004/0092962 A1 | 5/2004 | Thornton et al. |
| 2004/0122514 A1 | 6/2004 | Fogarty et al. |
| 2004/0127982 A1 | 7/2004 | Machold et al. |
| 2004/0127983 A1 | 7/2004 | Mortier et al. |
| 2004/0133274 A1 | 7/2004 | Webler |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1* | 7/2004 | Cartledge et al. ............ 623/2.37 |
| 2004/0153146 A1 | 8/2004 | Lashinski |
| 2004/0181287 A1 | 9/2004 | Gellman |
| 2004/0186566 A1 | 9/2004 | Hindrichs |
| 2004/0193191 A1 | 9/2004 | Starksen et al. |
| 2004/0236419 A1 | 11/2004 | Milo |
| 2004/0243227 A1 | 12/2004 | Starksen et al. |
| 2004/0260393 A1 | 12/2004 | Rahdert et al. |
| 2004/0260394 A1 | 12/2004 | Douk et al. |
| 2005/0004668 A1 | 1/2005 | Aklog |
| 2005/0016560 A1 | 1/2005 | Voughlohn |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee |
| 2005/0090827 A1 | 4/2005 | Gedebou |
| 2005/0096740 A1 | 5/2005 | Langberg et al. |
| 2005/0171601 A1 | 8/2005 | Cosgrove et al. |
| 2005/0177228 A1 | 8/2005 | Solem et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222678 A1 | 10/2005 | Lashinski et al. |
| 2005/0273138 A1 | 12/2005 | To et al. |
| 2005/0288778 A1 | 12/2005 | Shaoulian et al. |
| 2005/0288781 A1 | 12/2005 | Moaddeb et al. |
| 2006/0020326 A9 | 1/2006 | Bolduc et al. |
| 2006/0025787 A1 | 2/2006 | Morales et al. |
| 2006/0041319 A1 | 2/2006 | Taylor et al. |
| 2006/0069429 A1 | 3/2006 | Spence et al. |
| 2006/0116757 A1 | 6/2006 | Lashinski et al. |
| 2006/0129166 A1 | 6/2006 | Lavelle |
| 2006/0161265 A1 | 7/2006 | Levine et al. |
| 2006/0195134 A1 | 8/2006 | Crittenden |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0282161 A1 | 12/2006 | Huynh et al. |
| 2006/0287716 A1 | 12/2006 | Banbury et al. |
| 2007/0016287 A1* | 1/2007 | Cartledge et al. ............ 623/2.11 |
| 2007/0016288 A1 | 1/2007 | Gurskis |
| 2007/0027536 A1 | 2/2007 | Mihaljevic et al. |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0080188 A1 | 4/2007 | Spence et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0162111 A1 | 7/2007 | Fukamachi et al. |
| 2007/0198082 A1 | 8/2007 | Kapadia et al. |
| 2007/0213582 A1 | 9/2007 | Zollinger et al. |
| 2007/0219558 A1 | 9/2007 | Deutsch |
| 2007/0244556 A1 | 10/2007 | Rafiee et al. |
| 2007/0250160 A1 | 10/2007 | Rafiee |
| 2007/0255397 A1 | 11/2007 | Ryan |
| 2007/0255400 A1 | 11/2007 | Parravicini et al. |
| 2007/0282375 A1 | 12/2007 | Hindrichs et al. |
| 2007/0295172 A1 | 12/2007 | Swartz |
| 2008/0004697 A1 | 1/2008 | Lichtenstein et al. |
| 2008/0027483 A1 | 1/2008 | Cartledge |
| 2008/0035160 A1 | 2/2008 | Woodson et al. |
| 2008/0051703 A1 | 2/2008 | Thornton |
| 2008/0058595 A1 | 3/2008 | Snoke et al. |
| 2008/0086203 A1 | 4/2008 | Roberts |
| 2008/0097523 A1 | 4/2008 | Bolduc et al. |
| 2008/0167714 A1 | 7/2008 | St. Goar |
| 2008/0177382 A1 | 7/2008 | Hyde et al. |
| 2008/0195126 A1 | 8/2008 | Solem |
| 2008/0262609 A1 | 10/2008 | Gross et al. |
| 2008/0275551 A1* | 11/2008 | Alfieri .................. 623/2.36 |
| 2008/0281411 A1 | 11/2008 | Berreklouw |
| 2008/0288044 A1 | 11/2008 | Osborne |
| 2009/0043153 A1 | 2/2009 | Zollinger et al. |
| 2009/0054969 A1 | 2/2009 | Salahieh et al. |
| 2009/0099650 A1 | 4/2009 | Bolduc et al. |
| 2009/0171439 A1 | 7/2009 | Nissl |
| 2009/0177266 A1 | 7/2009 | Powell et al. |
| 2009/0248148 A1 | 10/2009 | Shaolian |
| 2009/0287304 A1 | 11/2009 | Dahlgren et al. |
| 2009/0326648 A1 | 12/2009 | Machold et al. |
| 2010/0010538 A1 | 1/2010 | Juravic et al. |
| 2010/0023117 A1 | 1/2010 | Yoganathan |
| 2010/0023118 A1 | 1/2010 | Medlock |
| 2010/0042147 A1 | 2/2010 | Janovsky |
| 2010/0094248 A1 | 4/2010 | Nguyen |
| 2010/0130992 A1 | 5/2010 | Machold et al. |
| 2010/0152845 A1 | 6/2010 | Bloom |
| 2010/0161041 A1 | 6/2010 | Maisano et al. |
| 2010/0161042 A1 | 6/2010 | Maisano |
| 2010/0161043 A1 | 6/2010 | Maisano et al. |
| 2010/0161047 A1 | 6/2010 | Cabiri |
| 2010/0168845 A1 | 7/2010 | Wright |
| 2010/0174358 A1 | 7/2010 | Rabkin et al. |
| 2010/0179574 A1 | 7/2010 | Longoria |
| 2010/0211166 A1* | 8/2010 | Miller et al. ................ 623/2.37 |
| 2010/0217382 A1 | 8/2010 | Chau et al. |
| 2010/0234935 A1 | 9/2010 | Bashiri et al. |
| 2010/0280604 A1 | 11/2010 | Zipory |
| 2010/0280605 A1 | 11/2010 | Hammer |
| 2010/0286767 A1 | 11/2010 | Zipory |
| 2010/0324598 A1 | 12/2010 | Anderson |
| 2011/0029066 A1 | 2/2011 | Gilad |
| 2011/0082538 A1 | 4/2011 | Dahlgren |
| 2011/0093002 A1 | 4/2011 | Rucker et al. |
| 2011/0106247 A1 | 5/2011 | Miller |
| 2011/0166649 A1 | 7/2011 | Gross et al. |
| 2011/0184510 A1 | 7/2011 | Maisano et al. |
| 2011/0190879 A1 | 8/2011 | Bobo et al. |
| 2011/0208283 A1 | 8/2011 | Rust |
| 2011/0238088 A1 | 9/2011 | Bolduc |
| 2011/0282361 A1 | 11/2011 | Miller |
| 2012/0078355 A1 | 3/2012 | Zipory |
| 2012/0123531 A1 | 5/2012 | Tsukashima |
| 2012/0136436 A1 | 5/2012 | Cabiri |
| 2012/0330410 A1 | 12/2012 | Hammer |
| 2013/0116780 A1 | 5/2013 | Miller |

FOREIGN PATENT DOCUMENTS

| | | |
|---|---|---|
| WO | 02/085251 | 10/2002 |
| WO | 02/085252 | 10/2002 |
| WO | 03/047467 | 6/2003 |
| WO | 2004/103434 | 12/2004 |
| WO | 2005/021063 | 3/2005 |
| WO | 2005/046488 | 5/2005 |
| WO | 2006/012013 | 2/2006 |
| WO | 2006/012038 | 2/2006 |
| WO | 2006/086434 | 8/2006 |
| WO | 2006/097931 | 9/2006 |
| WO | 2006/105084 | 10/2006 |
| WO | 2006/116558 | 11/2006 |
| WO | 2007/011799 | 1/2007 |
| WO | 2007/136783 | 11/2007 |
| WO | 2008/068756 | 12/2007 |
| WO | 2010/004546 | 1/2010 |
| WO | 2010/073246 | 7/2010 |

(56) References Cited

FOREIGN PATENT DOCUMENTS

| WO | 2010/128502 | | 11/2010 |
|---|---|---|---|
| WO | 2010/128503 | | 11/2010 |
| WO | 2011/067770 | A1 | 6/2011 |
| WO | 2011/089601 | | 7/2011 |
| WO | 2012/014201 | | 2/2012 |

OTHER PUBLICATIONS

An International Search Report dated Sep. 8, 2009, which issued during the prosecution of Applicant's PCT/IL09/00593.
U.S. Appl. No. 60/873,075, filed Dec. 5, 2006.
U.S. Appl. No. 60/902,146, filed Feb. 16, 2007.
U.S. Appl. No. 61/001,013, filed Oct. 29, 2007.
U.S. Appl. No. 61/132,295, filed Jun. 16, 2008.
"Two dimensional real-time ultrasonic imaging of the heart and great vessels", Mayo Clin Proc. vol. 53:271-303, 1978.
An International Search Report and a Written Opinion both dated Jun. 10, 2010, which issued during the prosecution of Applicant's PCT/IL09/01209.
An Office Action dated Apr. 6, 2010, which issued during the prosecution of Applicant's U.S. Appl. No. 12/484,512.
An Office Action dated Aug. 4, 2010, which issued during the prosecution of Applicant's U.S. Appl. No. 12/341,960.
An Office Action dated Oct. 6, 2010, which issued during the prosecution of Applicant's U.S. Appl. No. 12/484,512.
An International Search Report and a Written Opinion, both dated Nov. 8, 2010, issued during the prosecution of Applicant's PCT/IL10/00358.
An Office Action dated Jul. 20, 2012, which issued during the prosecution of U.S. Appl. No. 12/843,412.
An Office Action dated Mar. 9, 2012, which issued during the prosecution of U.S. Appl. No. 13/689,635.
An Office Action dated Jan. 23, 2012, which issued during the prosecution of U.S. Appl. No. 12/692,061.
An Office Action dated Dec. 29, 2011, which issued during the prosecution of U.S. Appl. No. 12/563,952.
An International Search Report dated Aug. 17, 2010, which issued during the prosecution of Applicant's PCT/IL2010/000357.
An International Preliminary Report on Patentability dated Nov. 9, 2011, which issued during the prosecution of Applicant's PCT/IL2010/000357.
U.S. Appl. No. 61/207,908, filed Feb. 17, 2009.
U.S. Appl. No. 61/265,936, filed Dec. 2, 2009.
An International Search Report dated Feb. 2, 2012, which issued during the prosecution of Applicant's PCT/IL2011/000600.
U.S. Appl. No. 61/283,445, filed Dec. 2, 2009.
An Office Action dated Aug. 5, 2010 which issued during the prosecution of U.S. Appl. No. 11/950,930.
An Office Action dated Feb. 17, 2010 which issued during the prosecution of U.S. Appl. No. 11/950,930.
An Office Action dated Sep. 16, 2009 which issued during the prosecution of U.S. Appl. No. 11/950,930.
An Office Action dated Mar. 29, 2011 which issued during the prosecution of U.S. Appl. No. 12/341,960.
An Office Action dated Sep. 28, 2011 which issued during the prosecution of U.S. Appl. No. 12/437,103.
An Office Action dated Jun. 13, 2012 which issued during the prosecution of U.S. Appl. No. 12/437,103.
An Office Action dated Dec. 29, 2011 which issued during the prosecution of U.S. Appl. No. 12/563,952.
An Office Action dated May 24, 2012 which issued during the prosecution of U.S. Appl. No. 12/563,952.
An International Preliminary Report on Patentability dated Jun. 29, 2011, which issued during the prosecution of Applicant's PCT/IL2009/001209.
An International Preliminary Report on Patentability dated Nov. 9, 2011, issued during the prosecution of Applicant's PCT/IL10/00358.
An International Search Report and a Written Opinion both dated Dec. 6, 2012, which issued during the prosecution of Applicant's PCT/IL2012/000250.
An Office Action dated Nov. 30, 2012, which issued during the prosecution of U.S. Appl. No. 12/689,635.
Supplementary European Search Report dated Dec. 4, 2012, which issued during the prosecution of European Patent Application No. 09834225.
An Office Action dated Feb. 14, 2013, which issued during the prosecution of U.S. Appl. No. 13/167,492.
An International Search Report and a Written Opinion both dated Feb. 22, 2013, which issued during the prosecution of Applicant's PCT/IL2012/050451.
Supplementary European Search Report dated Mar. 28, 2013, which issued during the prosecution of EP Patent Application No. 10772091.
An Office Action dated Apr. 1, 2013, which issued during the prosecution of U.S. Appl. No. 13/167,476.
An Office Action dated Jun. 7, 2013, which issued during the prosecution of U.S. Appl. No. 13/141,606.
Office Action, dated Feb. 3, 2014, issued by the United States Patent and Trademark Office, in counterpart U.S. Appl. No. 12/689,693.
International Search Report and Written Opinion, dated Apr. 9, 2014, issued by the International Searching Authority, in counterpart Application No. PCT/IL13/50860.
Final Office Action issued in U.S. Appl. No. 13/167,492 on Oct. 2, 2013.
An Office Action dated Dec. 16, 2013, which issued during the prosecution of U.S. Appl. No. 13/666,262.
An Office Action dated Nov. 21, 2013, which issued during the prosecution of U.S. Appl. No. 13/167,476.
An Office Action dated Dec. 18, 2013, which issued during the prosecution of U.S. Appl. No. 13/666,141.
An Office Action dated Dec. 19, 2013, which issued during the prosecution of U.S. Appl. No. 14/027,934.
An Office Action dated Dec. 27, which issued during the prosecution of U.S. Appl. No. 12/785,717.
English Translation of an Office Action dated Jul. 25, 2014, issued by the the State Intellectual Property Office of the People's Republic of China in counterpart Application No. 200980157331.3.
Communication dated Oct. 14, 2014, issued by the United States Patent and Trademark Office in counterpart U.S. Appl. No. 13/319,030.
Communication dated Sep. 29, 2014, issued by the United States Patent Office in counterpart U.S. Appl. No. 13/504,870.
Communication dated Aug. 22, 2014, issued by the United States Patent and Trademark Office in counterpart U.S. Appl. No. 14/027,934.
Communication dated Oct. 3, 2014, issued by the United States Patent and Trademark Office in counterpart U.S. Appl. No. 13/749,153.
An Office Action dated Jun. 2, 2014, which issued during the prosecution of U.S. Appl. No. 13/319,030.
An Office Action dated Jun. 10, 2014, which issued during the prosecution of U.S. Appl. No. 13/167,492.
An Office Action dated Jun. 4, 2014, which issued during the prosecution of U.S. Appl. No. 12/840,463.
An English translation of an Office Action dated Apr. 23, 2014, which issued during the prosecution of Chinese Patent Application No. 201080059948.4.
An Office Action dated Jun. 11, 2014, which issued during the prosecution of U.S. Appl. No. 14/027,934.
Notice of Allowance dated Jun. 11, 2014, which issued during the prosecution of U.S. Appl. No. 12/689,693.
Notice of Allowance dated Jun. 25, 2014, which issued during the prosecution of U.S. Appl. No. 13/666,262.

\* cited by examiner

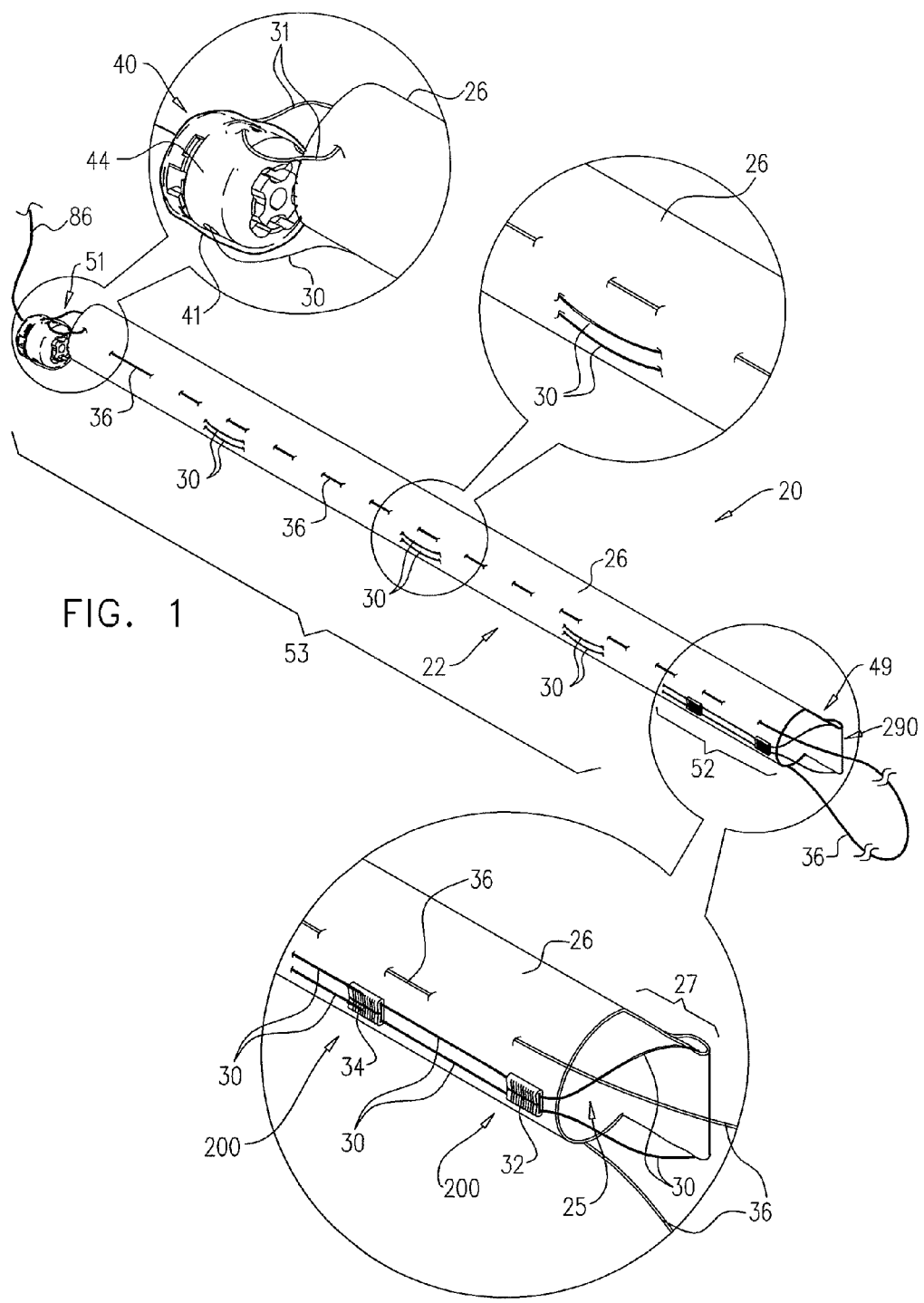

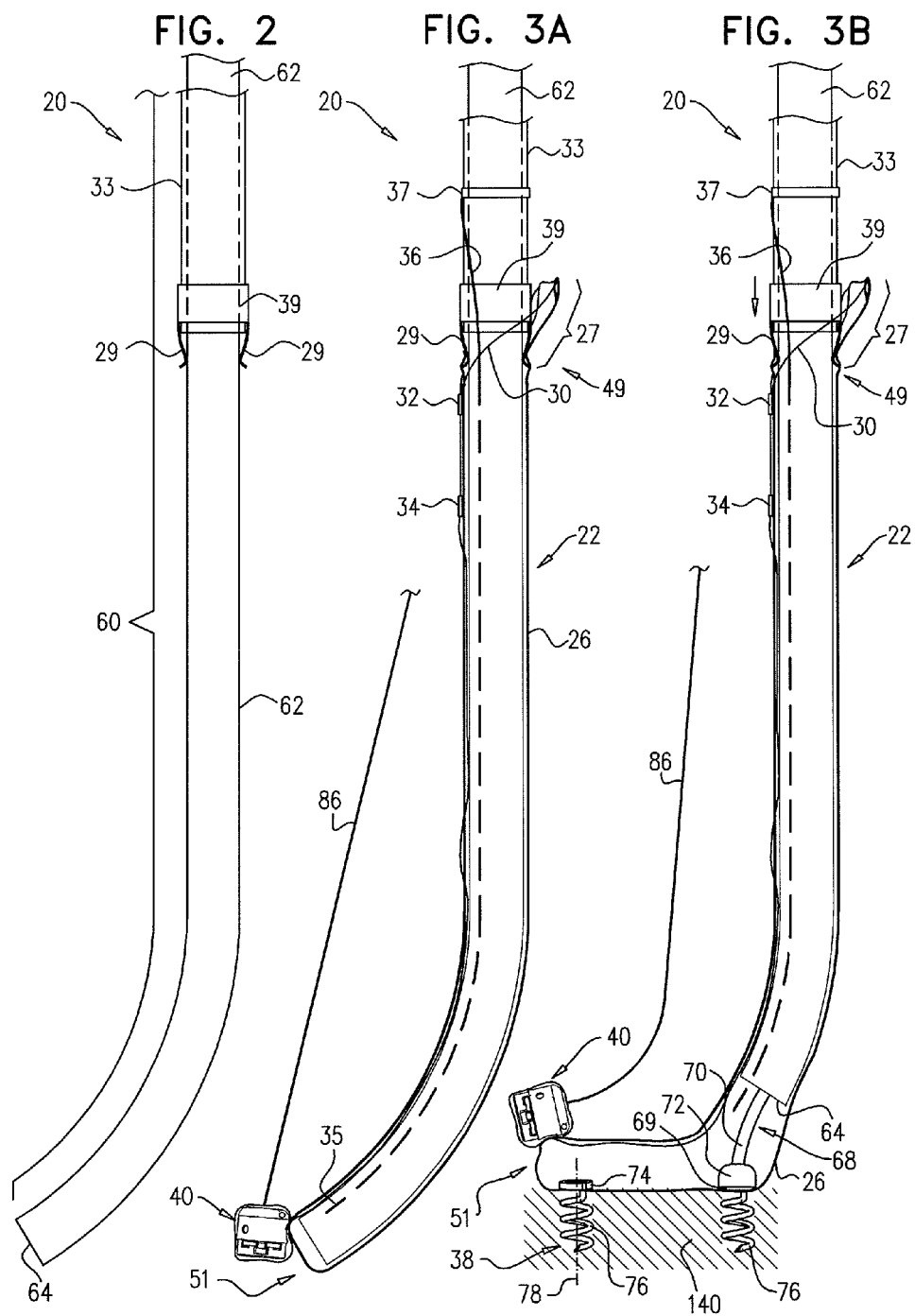

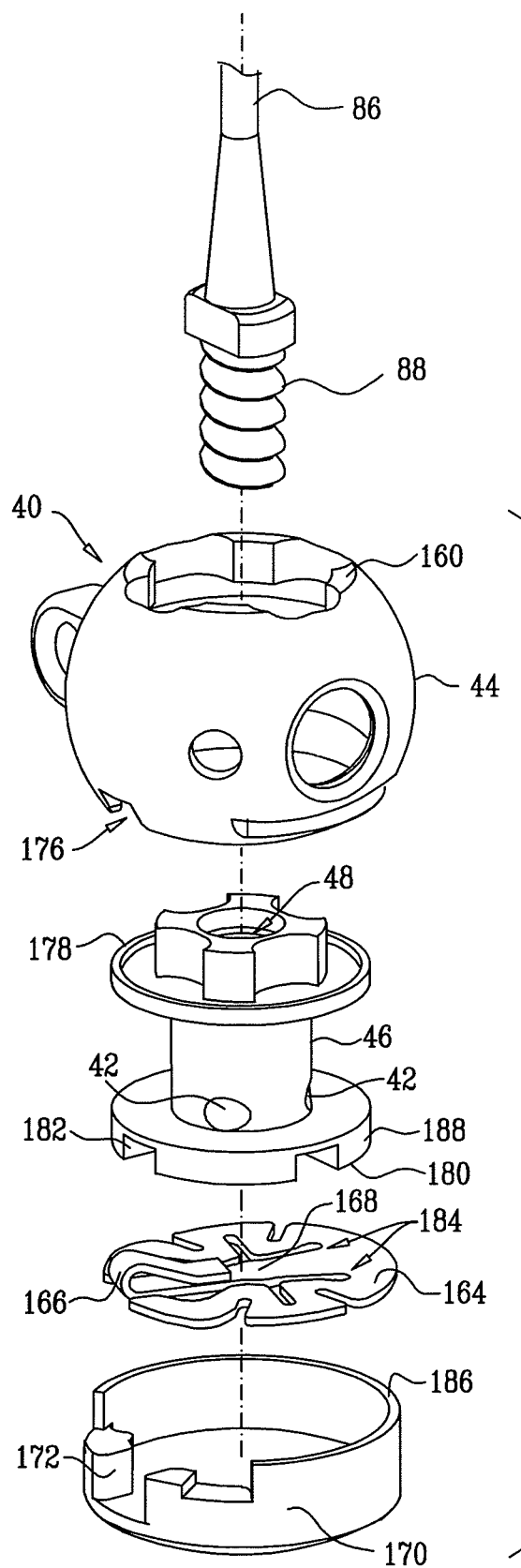

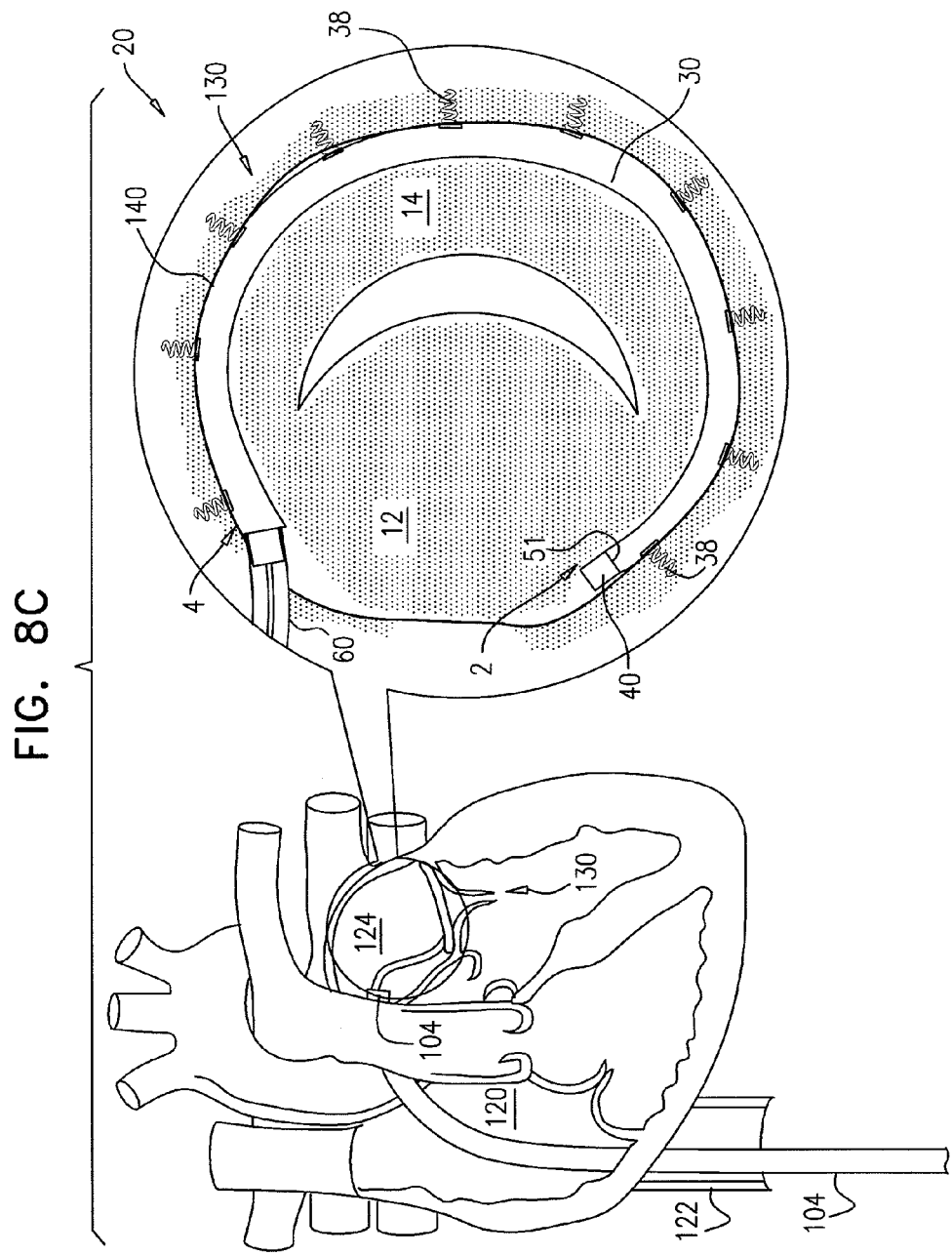

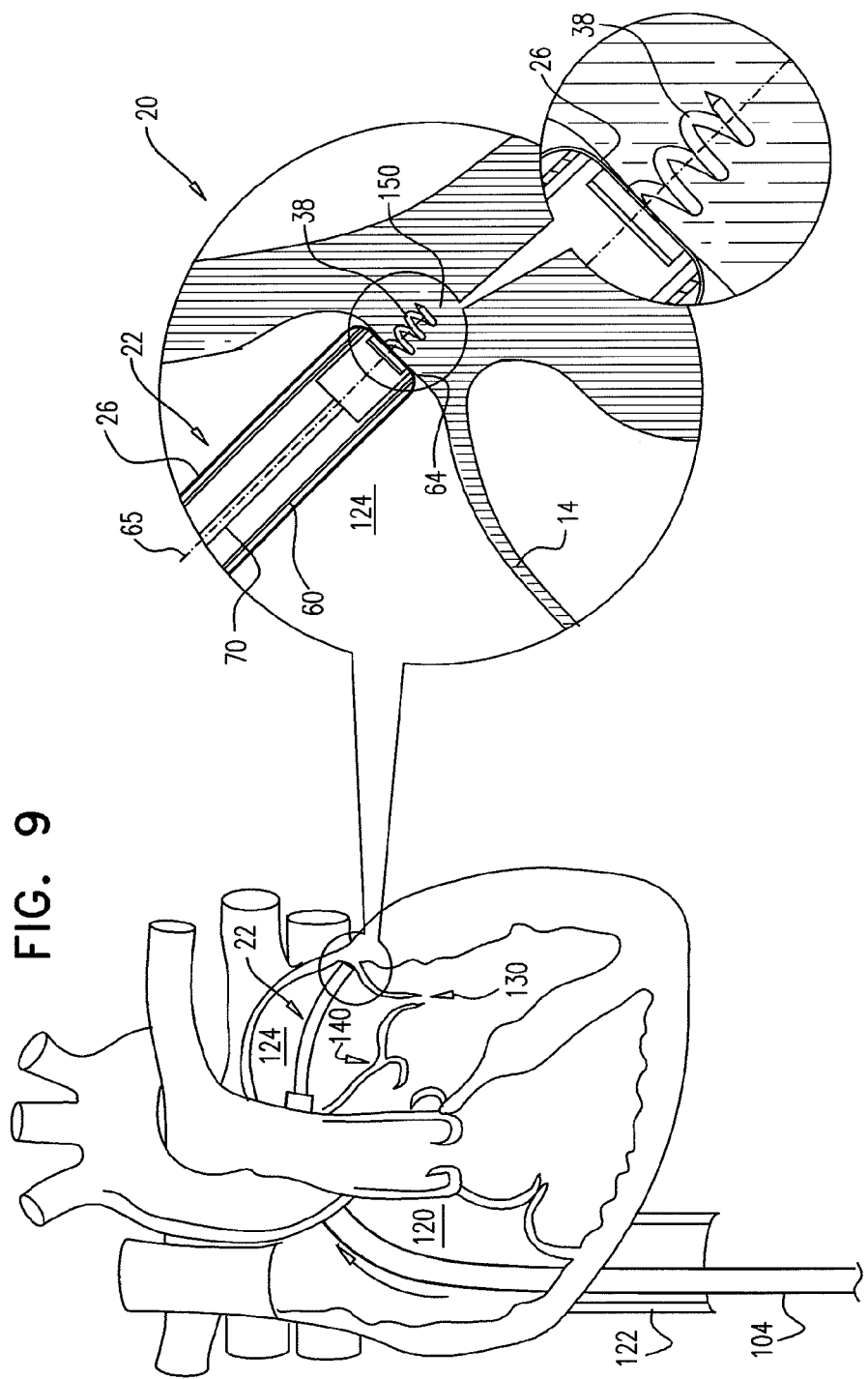

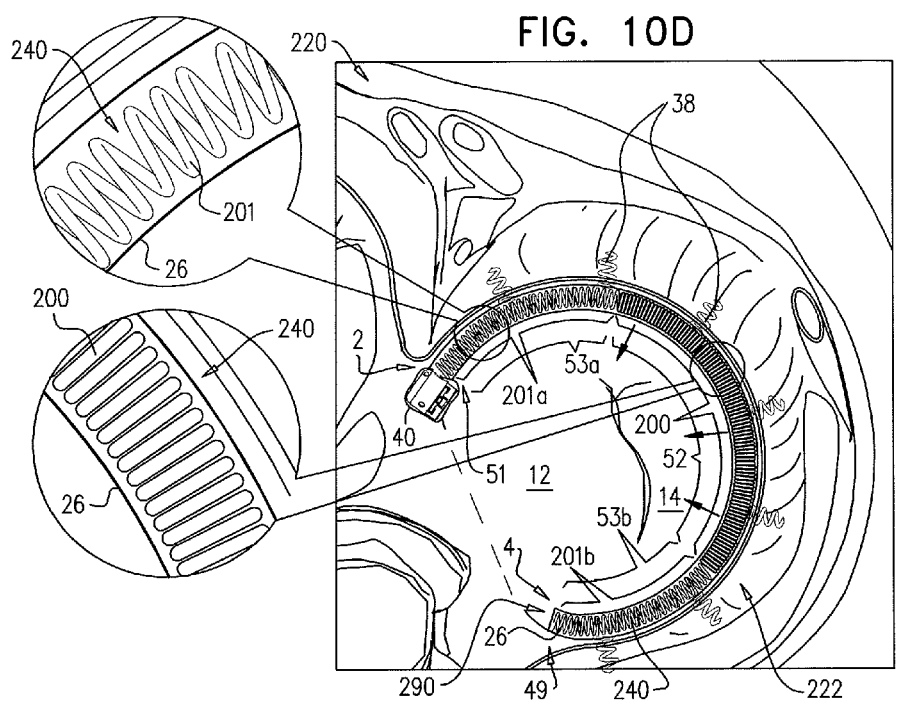
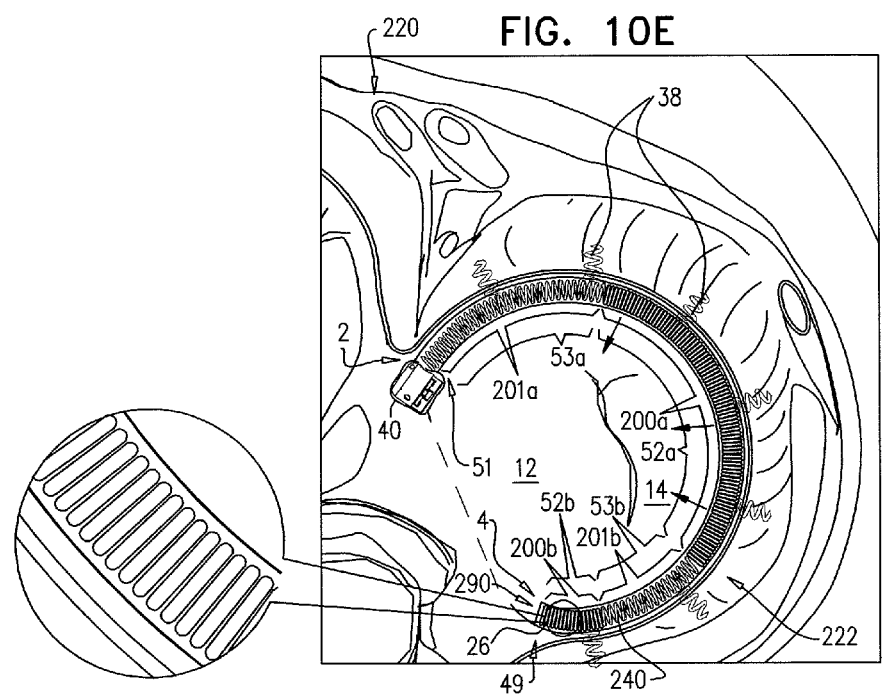

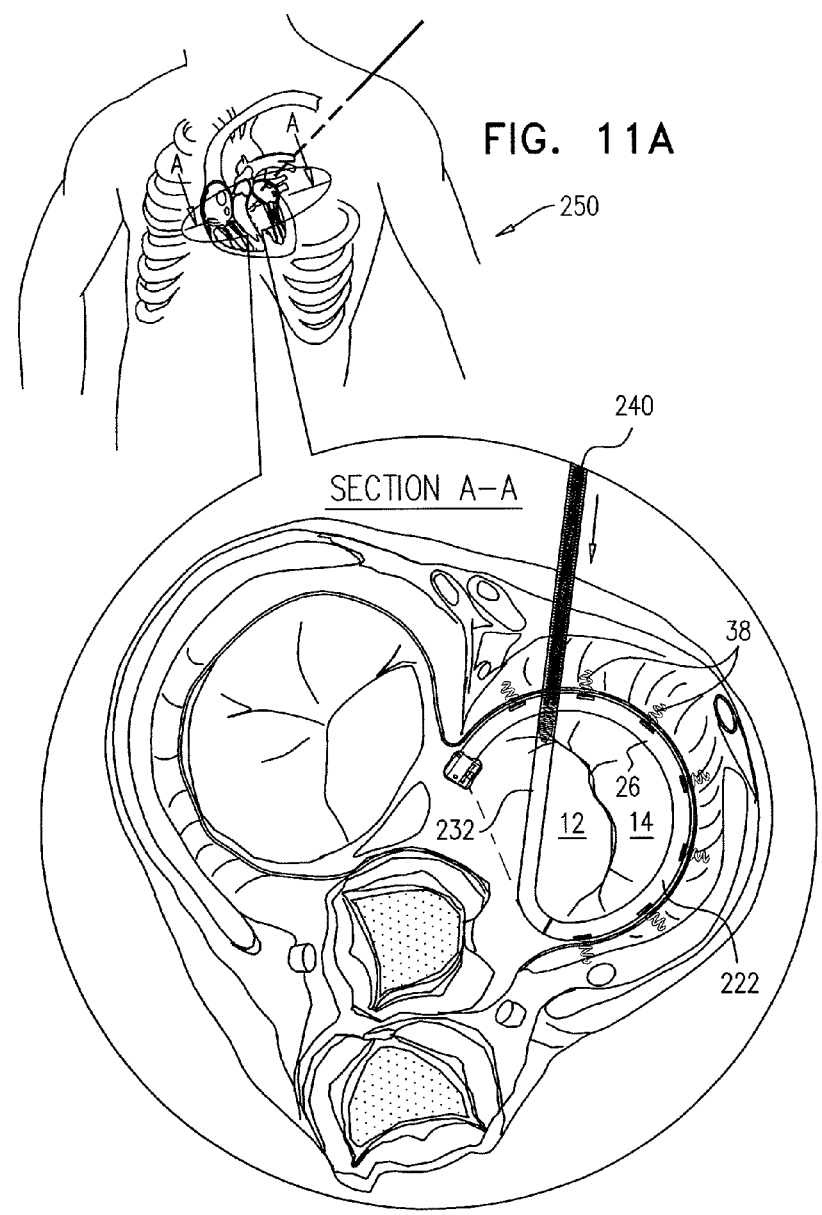

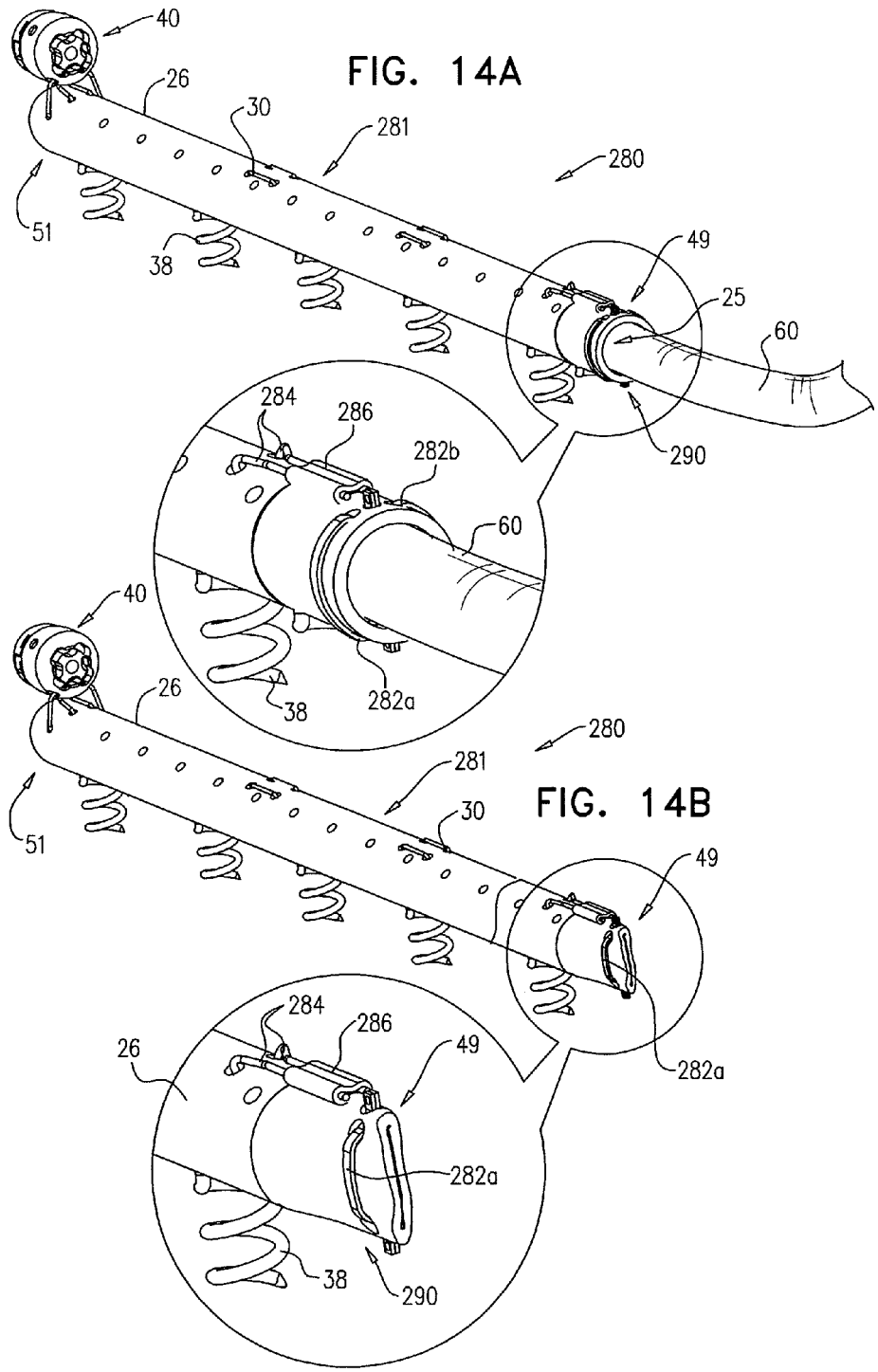

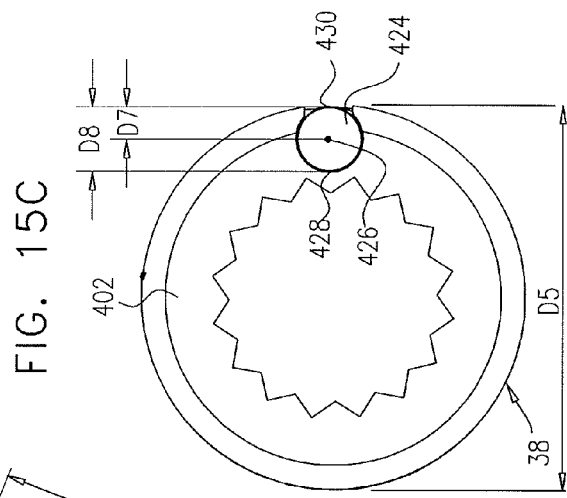
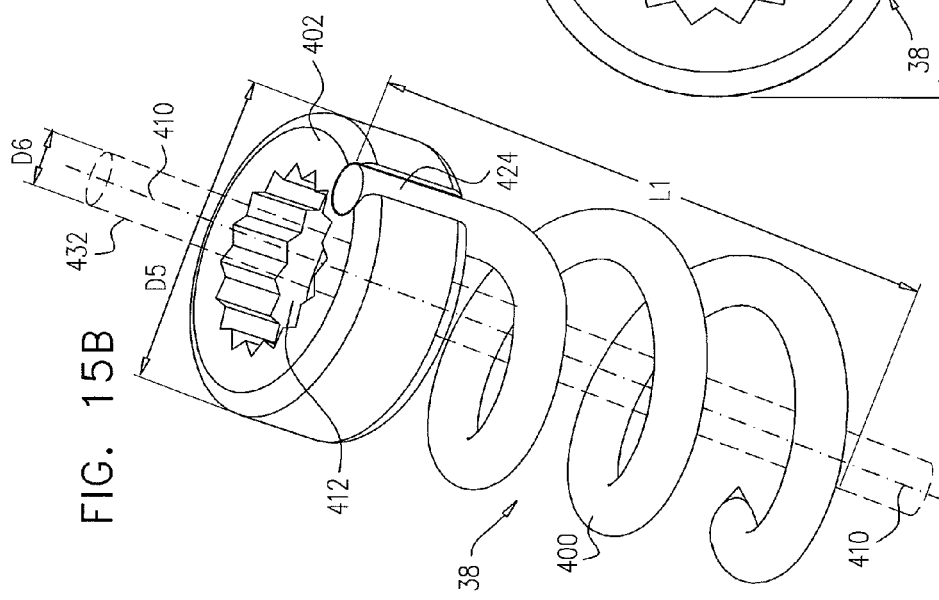
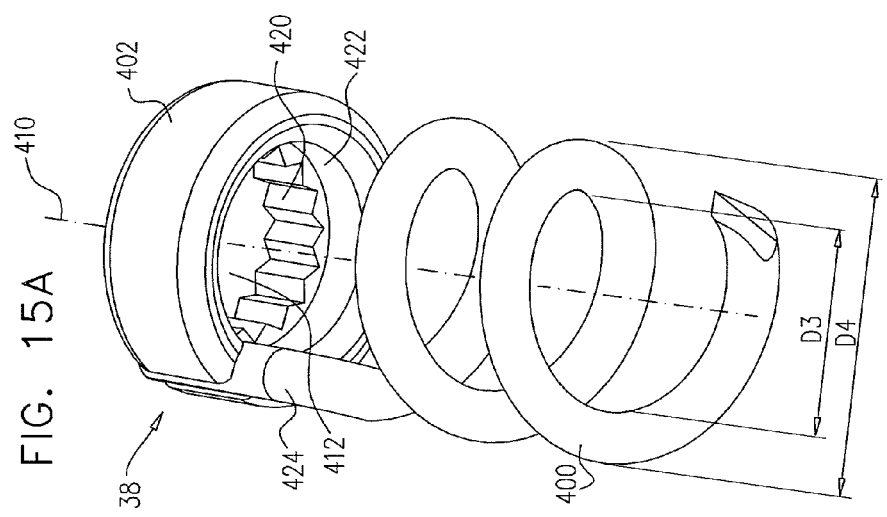

PARTIALLY-ADJUSTABLE ANNULOPLASTY STRUCTURE

CROSS-REFERENCES TO RELATED APPLICATIONS

The present patent application is a continuation-in-part of U.S. patent application Ser. No. 12/341,960 to Cabiri, filed Dec. 22, 2008 (published as US 2010/0161047 and is now U.S. Pat. No. 8,241,351), which is incorporated herein by reference.

FIELD OF THE INVENTION

Some embodiments of the present invention relate in general to valve repair, and more specifically to repair of an atrioventricular valve of a patient.

BACKGROUND

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

SUMMARY

In some applications of the present invention, apparatus is provided that comprises an implant structure comprising a sleeve having a lumen and at least one opening at a first end of the implant structure. The implant structure additionally comprises a closure element (e.g., a closure mechanism) configured to close the at least one opening at the first end of the implant structure. The implant structure comprises a contracting mechanism configured to contract and expand the implant structure at least in part. For some applications, the closure mechanism comprises at least one end flap, and the contracting mechanism is configured to actuate the end flap so as to cover the at least one opening. For other applications, the closure mechanism comprises self-closing strips which are biased to close around the portion of the implant structure that defines the at least one opening.

Typically, the implant structure comprises at least part of an annuloplasty structure (e.g., a partial annuloplasty ring) for repairing a dilated valve annulus of a native atrioventricular valve, such as a mitral valve, of a patient. One or more flexible, longitudinal contracting members (e.g., a wire, string, or suture) are coupled to the sleeve of the implant structure by being threaded one or more times through the sleeve. Additionally, the contracting member is coupled at a first portion thereof to the contracting mechanism. For applications in which the closure mechanism comprises the end flap, a second portion of the contracting member is coupled to the end flap. When the contracting mechanism is actuated in a first actuation direction, the contracting mechanism pulls on the contracting member which, in turn, pulls on the end flap, thereby covering the opening at least in part. One or more contraction-restricting elements are coupled to the implant structure and/or to the contracting member. The one or more contraction-restricting elements are configured to restrict contraction of at least a first portion of the implant structure beyond a predetermined amount while the contraction of the remaining portion(s) of the implant structure is ongoing.

The contracting mechanism comprises a rotatable structure, arranged such that rotation of the rotatable structure adjusts a perimeter of the implant structure. A longitudinal guide member (e.g., a wire, string, or suture) is coupled to the rotatable structure. A rotation tool is provided for rotating the rotatable structure. The tool is configured to be guided along (e.g., over, alongside, or through) the longitudinal guide member, to engage the rotatable structure, and to rotate the rotatable structure in response to a rotational force applied to the tool.

In some applications of the present invention, the apparatus comprises a plurality of anchors. An anchor deployment manipulator is advanced into a lumen of the sleeve, and, from within the lumen, deploys the anchors through a wall of the sleeve and into cardiac tissue, thereby anchoring the sleeve around a portion of the valve annulus. The anchor deployment manipulator is typically deflectable.

In some applications of the present invention, the anchor deployment manipulator comprises a steerable tube in which is positioned an anchor driver having an elongated, flexible shaft. Rotation of the anchor driver screws the anchors into the cardiac tissue. The anchors may, for example, be helical in shape. One or more stiffening elements, e.g., wires or sutures, are threaded through one or more portions of the sleeve in order to maintain relative positioning of the anchor driver relative to the implant structure during deflection of the anchor driver within the sleeve.

For some applications, the annuloplasty ring is typically configured to be placed only partially around the valve annulus (e.g., to assume a C-shape), and, once anchored in place, to be contracted so as to circumferentially tighten the valve annulus. To this end, the annuloplasty ring comprises the flexible contracting member. For some applications of the present invention, the implant structure comprises one or more contraction-restricting elements configured to restrict contraction of at least a portion of the implant structure. Thus, the implant structure is partially-contractible.

Typically, a first anchor is deployed at or in a vicinity of a first trigone of the valve, and a second anchor is deployed at or in a vicinity of a second trigone. For valves which are particularly distended, the implant structure is anchored to the first trigone at a first free end thereof and is anchored to the second trigone at a second free end thereof. For applications in which the implant structure is implanted along an annulus of a mitral valve, the body portion of the implant structure extends from the first trigone and toward and along a portion of the annulus that is adjacent to the posterolateral leaflet. For such an application, the contraction-restricted portion is disposed along the annulus and therefore, a portion of the implant structure is contracted (i.e., a contraction-facilitated portion), thereby contracting a portion of the annulus that is between the first and second trigones and adjacent to the posterolateral leaflet and, thereby, reducing a perimeter of the valve annulus and drawing the leaflets together.

For other applications, the second free end is not anchored to the trigone, but is instead anchored to a portion of the atrial wall (e.g., a portion of the interatrial septum or a portion of a free wall) of the heart of the patient while the first free end or a first portion of the implant structure adjacent the first free end is anchored to the first trigone. For some applications, the entire contraction-restricted portion is attached to the portion of the atrial wall and the contraction-facilitated portion is disposed between the first and second trigones and runs along the portion of the annulus that is adjacent to the posterolateral leaflet. For such applications in which the implant structure is implanted at the mitral valve, the entire portion of the annulus that is between the first and second trigones and adjacent the posterolateral leaflet is contracted, thereby reducing a perimeter of the valve annulus and drawing the leaflets together.

For some applications, the contracting mechanism comprises a spool to which a first end of the contracting member is coupled. Rotation of the spool winds a portion of the contracting member around the spool, thereby contracting the implant structure. For some applications, the contracting mechanism comprises a housing that houses the spool, and the rotation tool is configured to engage and rotate the spool with respect to the housing. For some applications, the rotation tool comprises a tube, which is configured to be passed over the longitudinal member coupled to the contracting mechanism, and to engage the housing, such that the housing is held rotationally stationary when the tube is held rotationally stationary.

For some application in which the implant structure comprises an annuloplasty ring, all of the tools and elements of the annuloplasty system that are introduced into left atrium are contained within the sleeve of the annuloplasty ring, which reduces the risk that any elements of the system will accidentally be released to the blood circulation, or damage surrounding tissue. In addition, the lumen of the sleeve provides guidance if it should be necessary to return to a previously deployed anchor, such as to tighten, loosen, remove, or relocate the anchor. For some applications, the anchors comprise helical screws, which facilitate such adjusting or removing.

The annuloplasty ring may be advanced toward the annulus of a valve in any suitable procedure, e.g., a transcatheter procedure, a percutaneous procedure, a minimally invasive procedure, or an open heart procedure.

There is therefore provided, in accordance with some applications of the present invention, apparatus, including:

an implant structure configured to treat a native atrioventricular valve of a patient, the implant structure including:
a sleeve having a lumen and at least one end, the at least one end being shaped so as to define an opening; and
a closure element disposed in a vicinity of the at least one end, the closure element being configured to facilitate closure of the opening; and
a contracting mechanism coupled to the implant structure and configured to contract at least a contraction-facilitated portion of the implant structure.

For some applications, the implant structure has a length of between 50 mm and 150 mm.

For some applications, the implant structure has a diameter of between 1 mm and 10 mm.

For some applications, the apparatus is configured to be implanted along an annulus of a mitral valve of the patient in a manner in which the implant structure is formed into at least a portion of an annuloplasty ring.

For some applications, the closure element includes a closure mechanism that includes one or more strips coupled to the sleeve in the vicinity of the at least one end of the sleeve, and the one or more strips have a tendency to be in a closed state in which the one or more strips close around at least a portion of the opening.

For some applications, the apparatus further includes a delivery tool advanceable within the lumen of the sleeve through the opening, and the tool is configured to expand the one or more strips while advanceable within the lumen of the sleeve and to facilitate positioning of the one or more strips in the closed state when removed from within the lumen of the sleeve.

For some applications, the apparatus further includes a contracting member coupled to the sleeve that facilitates contraction of the contraction-facilitated portion of the implant structure, the contracting member having a first portion thereof that is coupled to the contracting element.

For some applications, the contracting member is threaded through the sleeve one or more times to facilitate generally-even contraction of the implant structure.

For some applications, the apparatus further includes one or more contraction-restricting elements coupled to at least a contraction-restricted portion of the implant structure, the one or more contraction-restricting elements being configured to restrict contraction of at least the contraction-restricted portion of the implant structure beyond a predetermined amount.

For some applications, the one or more contraction-restricting elements is coupled to an outer surface of the implant structure.

For some applications, each one of the one or more contraction-restricting elements includes a segment having at least a portion thereof that is non-compressible along a longitudinal axis of the segment.

For some applications, at least one of contraction-restricting elements is disposed adjacently to one or more contraction-facilitated elements that are compressible along the longitudinal axis of the segment and facilitate contraction of respective portions of the implant structure in vicinities of the one or more contraction-facilitating elements.

For some applications, each one of the contraction restriction-elements is configured to restrict contraction of the contraction-restricted portion of the implant structure while facilitating radial movement of the contraction-restricted portion of the implant structure.

For some applications, at least one of the contraction-restricting elements includes a coiled element, and at least a portion of the coiled element is non-compressible.

For some applications, the coiled element includes a shape-memory material and is configured to be generally straightened from a coiled state during delivery of the implant structure to an implantation site of a body of the patient.

For some applications, the coiled element includes an elongate coiled element disposed within the lumen of the sleeve.

For some applications, the coiled element includes an elongate coiled element that is coupled to a portion of an outer surface of the sleeve and is disposed alongside the portion of the outer surface of the sleeve.

For some applications, the implant is configured for implantation along a native annulus of the native atrioventricular valve of the patient in a manner in which the contraction-restricted portion of the implant structure is disposed along a portion of the annulus at a posterior leaflet of the valve, and the contraction-restricting element is coupled to the contraction-restricted portion.

For some applications, the contraction restriction-element is configured to restrict contraction of the contraction-restricted portion while facilitating radial movement of the contraction-restricted portion.

For some applications:
the closure element includes at least one end flap that is disposed at the at least one end of the sleeve, and
the first portion of the contracting member is coupled to the end flap in a manner in which, in response to at least initial actuation of the contracting mechanism, the contracting member draws the end flap at least partially over the opening at the at least one end of the sleeve.

For some applications, the one or more contraction-restricting elements each have a length of between 3 and 120 mm.

For some applications:

the one or more contraction-restricting elements are coupled to the contracting member in a vicinity of the first portion thereof, the one or more contraction-restricting elements are disposed along the implant structure at a distance of between 3 and 45 mm from the at least one end of the sleeve, the contraction-restricted portion of the implant structure is between 3 and 45 mm from the at least one end of the sleeve, and the one or more contraction-restricting elements are configured to restrict contraction of the contraction-restricted portion of the implant structure during contraction of a remaining portion of the implant structure by the contracting member.

For some applications, the contracting mechanism is disposed at a first portion of the implant structure, and the contracting member extends along the implant structure from the first portion thereof to the at least one end of the sleeve.

For some applications, the one or more contraction-restricting elements are disposed in a vicinity of the at least one end of the sleeve, and the contracting member is looped through a portion of the flap and extends back toward the one or more contraction-restricting elements.

For some applications, the contracting mechanism includes a rotatable structure, and the actuation includes rotation of the rotatable structure in a first rotational direction in order to actuate the contracting member to draw the flap over the opening.

For some applications, in response to rotation of the rotatable structure in a second rotational direction that is opposite the first rotational direction, the contracting member draws the end flap at least partially away from the opening at the at least one end of the sleeve.

For some applications:

the at least one end of the sleeve defines a first free end of the implant structure, the implant structure is shaped so as to define a second free end, the apparatus is configured to be implanted along an annulus of an atrioventricular valve of the patient, and in response to actuation of the contracting mechanism, the first and second free ends of the implant structure are drawn toward one another.

For some applications, the apparatus is configured to be implanted along an annulus of a mitral valve of the patient, the first end of the implant structure is configured to be coupled to a first location along the annulus in a vicinity of a first trigone adjacent to the mitral valve, and the second end of the implant structure is configured to be coupled to a second location along the annulus in a vicinity of a second trigone adjacent to the mitral valve.

For some applications, the contracting mechanism includes a rotatable structure, and the actuation includes rotation of the rotatable structure in a first rotational direction to contract the implant structure.

For some applications, in response to rotation of the rotatable structure in a second rotational direction that is opposite the first rotational direction, the contracting member expands the implant structure.

For some applications, in response to rotation of the rotatable structure in a first rotational direction, successive portions of the contracting member advance in a first advancement direction with respect to the rotatable structure and contact the rotatable structure.

For some applications, the rotatable structure includes a spool, and, in response to the rotation of the spool in the first rotational direction, the contracting member is configured to be wound around the spool.

For some applications, in response to continued advancement of the contracting member in the first advancement direction by continued rotation of the rotatable structure in the first rotational direction, the at least one end of the sleeve is pulled toward the contracting mechanism.

For some applications:

the implant structure is configured to be implanted along an annulus of a mitral valve of the patient, the contracting member is configured to contract the implant structure in response to the rotation of the rotatable structure in the first rotational direction, and, the implant structure is configured to contract the annulus in response to the contraction of the implant structure.

For some applications, the successive portions of the contracting member are configured to be advanced in a second advancement direction with respect to the rotatable structure and thereby to facilitate expansion of the implant structure in response to rotation of the rotatable structure in a second rotational direction the second rotational direction being opposite the first rotational direction, and the second advancement direction being opposite the first advancement direction.

For some applications:

the rotatable structure has a first end shaped to define a first opening, and a second end shaped to define a second opening, the rotatable structure being shaped to define a channel extending from the first opening to the second opening, the channel being configured for passage therethrough of an elongate tool, and the second end of the rotatable structure has a lower surface thereof shaped to define one or more recesses.

For some applications, the apparatus further includes a mechanical element having a planar surface coupled to the lower surface of the rotatable structure, the mechanical element being shaped to provide:

a protrusion protruding out of a plane of the planar surface of the mechanical element, the protrusion being disposed within one of the recesses during a resting state of the mechanical element, in a manner that restricts rotation of the rotatable structure, and a depressible portion coupled to the protrusion, the depressible portion being disposed in communication with the second opening of the lower surface, and configured to dislodge the protrusion from within the recess in response to a force applied thereto by the elongate tool.

For some applications, the apparatus further includes:

one or more tissue anchors; and a deployment manipulator tube, which is configured to be removably positioned at least partially within the lumen of the sleeve, such that the deployment manipulator tube extends out of the at least one end of the sleeve; and an anchor driver which is reversibly coupleable to the one or more tissue anchors and which is configured to be at least partially positioned within the deployment manipulator tube, and, while so positioned, to deploy the one or more tissue anchors through a wall of the sleeve.

For some applications, the anchor driver is deflectable within the sleeve of the implant structure, and the apparatus further includes one or more stiffening elements, the one or more stiffening elements being threaded through one or more portions of the sleeve in order to maintain relative positioning of the manipulator tube relative to the implant structure during deflection of the anchor driver within the sleeve.

For some applications, the manipulator tube is deflectable within the sleeve of the implant structure, and the one or more stiffening elements are configured to maintain relative positioning of the implant structure relative to the manipulator tube during deflection of the manipulator tube.

For some applications, the apparatus further includes a pusher tube, which is configured to pass over a portion of the deployment manipulator tube, such that a distal end of the pusher tube is in contact with the at least one end of the sleeve.

For some applications, the distal end of the pusher tube is removably coupled to the at least one end of the sleeve.

For some applications, the pusher tube includes one or more coupling elements, which are configured to removably couple the distal end of the pusher tube to the at least one end of the sleeve.

For some applications, the apparatus is configured such that:

when the deployment manipulator tube is positioned within the lumen of the sleeve, the deployment manipulator tube causes the coupling elements to engage the sleeve, thereby removably coupling the distal end of the pusher tube to the at least one end of the sleeve, and when the deployment manipulator tube is withdrawn from the sleeve, the coupling elements disengage from the sleeve, thereby decoupling the distal end of the pusher tube from the at least one end of the sleeve.

For some applications, the coupling elements are configured to have a natural tendency to flex inwards toward a central longitudinal axis of the sleeve that passes through the at least one end of the sleeve, and the deployment manipulator tube, when positioned within the lumen of the sleeve, pushes the coupling elements outwards away from the longitudinal axis, thereby causing the coupling elements to engage the sleeve.

There is further provided, in accordance with some applications of the present invention, apparatus, including:

an implant structure configured to treat a native atrioventricular valve of a patient, the implant structure including:
  a sleeve having a lumen and at least one end, the at least one end being shaped so as to define an opening; and
  a closure element disposed in a vicinity of the at least one end, the closure element being configured to facilitate closure of the opening; and
an anchor delivery tool advanceable through the opening and within the lumen of the sleeve when the closure element does not facilitate closure of the opening.

There is additionally provided in accordance with some applications of the present invention, apparatus, including:

an implant structure configured to treat a native atrioventricular valve of a patient, the implant structure having a length of between 50 mm and 150 mm and a diameter of between 1 mm and 10 mm, the implant structure including:
  a sleeve having a lumen and at least one end, the at least one end being shaped so as to define an opening; and
  a closure element disposed in a vicinity of the at least one end, the closure element being configured to facilitate closure of the opening.

There is further provided, in accordance with some applications of the present invention, a method, including:

positioning an implant structure along an annulus of an atrioventricular valve of a patient, the implant structure including a sleeve having a lumen and at least one end, the at least one end being shaped so as to define an opening;

fastening at least a portion of the implant structure to the annulus; and closing the opening of the at least one end of the sleeve by actuating a closure element of the implant structure to close.

For some applications, positioning the implant structure along the annulus of the atrioventricular valve includes transcatheterally positioning the implant structure along the annulus of the atrioventricular valve.

For some applications, the method further includes driving one or more tissue anchors through a wall of the sleeve from within the lumen of the sleeve.

For some applications, positioning the implant structure along the annulus of the atrioventricular valve includes positioning the implant structure along the annulus in a manner in which the implant structure is formed into a least a portion of an annuloplasty ring.

For some applications, the closure element includes a closure mechanism that includes one or more strips coupled to the sleeve in a vicinity of the at least one end of the implant structure, the one or more strips have a tendency to be in a closed state in which the one or more strips close around at least a portion of the opening, and the method further includes:

expanding the one or more strips from the closed state by introducing a tool within the lumen of the sleeve, and facilitating positioning of the one or more strips in the closed state by extracting the tool from within the lumen of the sleeve.

For some application, fastening includes:

anchoring a first location of the implant structure to a first trigone of the valve; and anchoring a second location of the implant structure to a second trigone of the valve.

For some applications, anchoring the first location includes anchoring a first free end of the implant structure to the first trigone, and anchoring the second location includes anchoring a second free end of the implant structure to the second trigone.

For some applications, the method further includes contracting at least a first portion of the implant structure by actuating a contracting mechanism coupled to the implant structure.

For some applications, the method further includes restricting the contracting of at least a second portion of the implant structure that is less than the entire implant structure, during ongoing contracting of the first portion of the implant structure.

For some applications, restricting the contracting of the second portion of the implant structure includes restricting contraction of a contraction-restricted portion of the implant structure that has a length of between 3 mm and 120 mm.

For some applications, restricting the contracting includes coupling to the second portion of the implant structure a segment having at least a portion thereof that is non-compressible along a longitudinal axis of the segment.

For some applications, coupling the segment to the second portion of the implant structure includes coupling the segment to an outer surface of the implant structure in a vicinity of the second portion of the implant structure.

For some applications, coupling the segment to the outer surface of the implant structure includes restricting contraction of the portion of the implant structure while facilitating radial movement of the portion of the implant structure.

For some applications, positioning the implant structure along the annulus of the atrioventricular valve includes positioning the implant structure in a manner in which the second portion of the implant structure is disposed along a portion of the annulus at a posterior leaflet of the valve, and restricting contraction of the second portion of the implant structure includes restricting contraction of the portion of the annulus at the posterior leaflet of the valve.

For some applications, restricting the contracting of the second portion of the implant structure includes advancing into at least a portion of the lumen of the sleeve, a segment having at least a portion thereof that is non-compressible along a longitudinal axis of the segment.

For some applications, advancing the segment into the portion of the lumen of the sleeve includes advancing a segment that is disposed adjacently to one or more portions that are compressible along the longitudinal axis of the segment.

For some applications, advancing the segment into the portion of the lumen of the sleeve includes advancing a coiled segment into the portion of the sleeve.

For some applications, the method further includes, prior to advancing the coiled segment within the sleeve, advancing the coiled segment toward the sleeve in a generally straightened configuration, and advancing the coiled segment into the portion of the sleeve includes allowing the segment to form a coil within the sleeve.

For some applications, advancing the segment into the portion of the lumen of the sleeve includes restricting contraction of the second portion of the implant structure while facilitating radial movement of the second portion of the implant structure.

For some applications, positioning the implant structure along the annulus of the atrioventricular valve includes positioning the implant structure in a manner in which the second portion of the implant structure is disposed along a portion of the annulus at a posterior leaflet of the valve, and restricting contraction of the second portion of the implant structure includes restricting contraction of the portion of the annulus at the posterior leaflet of the valve.

For some applications, restricting the contracting of the second portion of the implant structure includes restricting contraction of a contraction-restricted portion of the implant structure that is between 3 and 45 mm from the at least one end of the sleeve, while facilitating contraction of a contraction-facilitated portion of the implant structure.

For some applications:
the at least one end of the sleeve defines a first free end of the implant structure,
the implant structure defines a second free end, and
the method further includes:
fastening the implant structure to a first trigone of the valve by fastening the implant structure to the valve in a vicinity of the first free end; and
fastening the implant structure to a second trigone of the valve by fastening the implant structure to the valve in a vicinity of the second free end.

For some applications:
fastening the implant structure to the first trigone includes fastening the first free end of the of the implant structure to the first trigone,
fastening the implant structure to the second trigone includes fastening the second free end of the of the implant structure to the second trigone,
fastening the at least the portion of implant structure to the annulus includes fastening the entire implant structure along the annulus between the first and second trigones, and
contracting the first portion of the implant structure includes contracting the contraction-facilitated portion of the implant structure that is between the second end and the contraction-restricted portion of the implant structure.

For some applications:
fastening the implant structure to the first trigone includes:
fastening the first free end of the of the implant structure to a portion of an atrial wall of a heart of the patient, and
fastening a portion of the implant structure that is adjacent to the first free end to the first trigone, and
anchoring the implant structure to the second trigone includes anchoring the second free end of the of the implant structure to the second trigone.

For some applications:
fastening the first free end of the of the implant structure to the portion of the atrial wall includes fastening the contraction-restricted portion of the implant structure to the portion of the atrial wall,
fastening the portion of the implant structure to the annulus includes fastening the contraction-facilitated portion of the implant to a posterior portion of the annulus between the first and second trigones, and
contracting the implant structure includes contracting the contraction-facilitated portion of the implant structure that is between the first and second trigones.

For some applications:
the atrioventricular valve includes a mitral valve;
the at least one end of the sleeve defines a first end of the implant structure,
the implant structure is shaped so as to define a second end, and
positioning the implant structure along the annulus includes:
positioning the first end of the implant structure at a first trigone of the mitral valve; and
positioning the second end of the implant structure at a second trigone of the mitral valve.

For some applications, contracting the first portion of the implant structure includes drawing the first and second ends of the implant structure toward one another.

For some applications, actuating the contracting mechanism includes rotating a rotatable structure of the contracting mechanism, and contracting the implant includes rotating the rotatable structure in a first rotational direction.

For some applications, the method further includes locking the contracting mechanism during a period that is subsequent to the rotating of the rotating structure.

For some applications, the closure element includes a flap at a vicinity of the opening of the sleeve, and the method further includes at least partially drawing the flap over the opening during a first period, by rotating the rotating mechanism in the first rotational direction.

For some applications, the method further includes, during a second period, drawing the end flap at least partially away from the opening at the at least one end of the sleeve by rotating the rotatable structure in a second rotational direction that is opposite the first rotational direction.

For some applications, responsively to rotating the rotatable structure, advancing in a first advancement direction with respect to the rotatable structure successive portions of a contracting member that is coupled to the implant structure, the contracting member is and is configured to contract the implant structure.

For some applications, the rotatable structure includes a spool, and advancing the successive portions of the contracting member in the first advancement direction includes winding the successive portions of the contracting member around the spool.

For some applications, contracting the first portion of the implant structure includes rotating further the rotatable member and advancing further successive portions of the contracting member in the first advancement direction, and the contracting includes drawing the at least one end of the sleeve toward the contracting mechanism.

For some applications, contracting the implant structure includes contracting the annulus of the atrioventricular valve.

For some applications, the method further includes expanding the implant structure by advancing the successive portions of the contracting member in a second advancement direction that is opposite the first advancement direction by rotating the rotatable structure in a second rotational direction that is opposite the first rotational direction.

For some applications, fastening the at least the portion of the implant structure to the annulus includes:
removably positioning a deployment manipulator tube through the opening and at least partially within the lumen of the sleeve of the implant structure, such that the deployment manipulator tube extends out of the at least one end of the sleeve; and
driving one or more tissue anchors through a wall of the sleeve from within the lumen of the sleeve.

For some applications:
driving the one or more anchors includes advancing through the deployment manipulator tube an anchor driver that is reversibly couplable to the one or more anchors,
exposing a distal end of the anchor driver from within a distal end of the deployment manipulator tube; and
deflecting through the sleeve the distal end of the anchor driver.

For some applications, the method further includes maintaining relative positioning of the implant structure relative to the manipulator tube during the deflecting by applying a force to one or more stiffening elements that are threaded through the sleeve of the implant structure.

For some applications, the method further includes placing a pusher tube over the deployment manipulator tube such that a distal end of the pusher tube is in contact with the at least one end of the sleeve.

For some applications, the at least one end of the sleeve includes a proximal end of the sleeve, and the method further includes withdrawing the sleeve from the deployment manipulator tube in a distal direction, and, while withdrawing, pushing the pusher tube against the proximal end of the sleeve.

For some applications, the method further includes, following the withdrawing, removably coupling the distal end of the pusher tube to the proximal end of the sleeve.

For some applications, removably coupling includes using one or more one or more coupling elements of the pusher tube to removably couple the distal end of the pusher tube to the proximal end of the sleeve.

For some applications, removably coupling includes positioning the deployment manipulator tube within the lumen of the sleeve such that the deployment manipulator tube causes the coupling elements to engage the sleeve, and the method further includes decoupling the distal end of the pusher tube from the proximal end of the sleeve by withdrawing the deployment manipulator tube from the sleeve such that the coupling elements disengage from the sleeve.

For some applications, positioning the implant structure along the annulus, and closing the opening of the at least one end of the sleeve include positioning the implant structure along the annulus, and closing the opening of the at least one end of the sleeve during a single procedure.

For some applications, positioning the implant structure along the annulus, and closing the opening of the at least one end of the sleeve include positioning the implant structure along the annulus, and closing the opening of the at least one end of the sleeve via a single catheter.

There is further provided, in accordance with some applications of the present invention, apparatus, including:
an annuloplasty structure configured for implantation along an annulus of an atrioventricular valve of a heart of a subject, the structure including:
a coiled element including:
at least one first portion thereof which is flexible and longitudinally compressible; and
at least one second portion thereof in series with the first portion, the second portion being flexible and less longitudinally compressible than the first portion.

For some applications, the coiled element is shaped such that a pitch of the coiled element at the second portion is smaller than a pitch of the coiled element at the first portion.

For some applications, a radius of curvature at a center of the first portion is smaller than a radius of curvature at a center of the second portion, when no external force is applied to the annuloplasty structure.

For some applications, the annuloplasty structure includes an annuloplasty ring.

For some applications, the annuloplasty structure includes a partial annuloplasty ring.

For some applications, the apparatus further includes a contraction-restricting element configured to be coupled to the second portion of the coiled element, and the second portion is configured to be flexible and less longitudinally compressible than the first portion at least in part by virtue of the contraction-restricting element being coupled thereto.

For some applications, the contraction-restricting element includes an element selected from the group consisting of: a suture, a staple, a ratchet mechanism, and a bracket.

For some applications, a total length of the first portion includes less than 50% of a resting length of the coiled element.

For some applications, a total length of the first portion includes less than 30% of a resting length of the coiled element.

For some applications, the valve includes a native mitral valve of the subject, and the structure is configured for implantation along the native mitral valve in a manner in which at least the second portion of the implant structure is disposed along a portion of the annulus at a posterior leaflet of the valve.

For some applications, the second portion is configured to restrict contraction of the second portion while facilitating radial movement of the second portion of the implant structure.

For some applications,
the atrioventricular valve includes a mitral valve,
the coiled element includes a plurality of second portions, and
the annuloplasty structure is configured for implantation along the annulus in a manner in which:
a first one of the second portions is configured to be coupled to the annulus in a vicinity of a left trigone adjacent to the mitral valve, and
a second one of the second portions is configured to be coupled to the annulus in a vicinity of a right trigone adjacent to the mitral valve.

For some applications, the combined length of the first and second of the second portions is 10-50 mm.

For some applications, the annuloplasty structure is configured for implantation along the annulus in a manner in which a third one of the second portions is disposed along a portion of the annulus at a posterior leaflet of the valve.

For some applications, a length of the third one of the second portions is 3-120 mm.

For some applications, a length of the third one of the second portions includes more than 20% of a resting length of the coiled element.

For some applications, the annuloplasty structure includes:

a sleeve, the sleeve having first and second end portions, respectively, and a body portion that is between the first and second end portions; and a contracting member that extends along the body portion between the first and second end portions of the sleeve, the contracting member having first and second end portions, the first end portion of the contracting member being coupled to the sleeve in a vicinity of the first end portion thereof, and the second end portion of the contracting member being coupled to the sleeve in a vicinity of the second end portion thereof, the coiled element being configured to be coupled to the sleeve.

For some applications, the annuloplasty structure has a length of between 50 mm and 150 mm.

For some applications, the annuloplasty structure has a diameter of between 1 mm and 10 mm.

For some applications, the annuloplasty structure is configured to be implanted along an annulus of a mitral valve of the subject in a manner in which the annuloplasty structure is formed into at least a portion of an annuloplasty ring.

For some applications, the annuloplasty structure includes a partial annuloplasty ring having first and second free ends, the first end of the sleeve defining the first free end of the partial annuloplasty ring, and the second end of the sleeve defining the second free end of the partial annuloplasty ring.

For some applications, the coiled element includes a shape-memory material configured to be generally straightened from a coiled state during delivery of the annuloplasty structure to an implantation site of a body of the subject.

For some applications, the sleeve defines a lumen, and the coiled element includes an elongate coiled element disposed within the lumen of the sleeve.

For some applications, the coiled element includes an elongate coiled element that is configured to be coupled to a portion of an outer surface of the sleeve and rest alongside the portion of the outer surface of the sleeve.

There is additionally provided, in accordance with some applications of the present invention, apparatus, including:

an implant structure that is contractible at least in part, the implant structure including a sleeve, the sleeve having first and second end portions, respectively, and a body portion that is between the first and second end portions;

a contracting member that extends along the body portion between the first and second end portions of the sleeve, the contracting member having first and second end portions, the first end portion of the contracting member being coupled to the sleeve in a vicinity of the first end portion thereof, and the second end portion of the contracting member being coupled to the sleeve in a vicinity of the second end portion thereof; and at least one contraction-restricting element that is coupled to the sleeve and configured to restrict contraction of a contraction-restricted portion of the implant structure during contraction of a remaining portion of the implant structure by the contracting member, the one or more contraction-restricting elements being coupled to the first end portion of the contracting member and disposed along the implant structure at a distance of between 3 and 45 mm from the first end of the sleeve, the contraction-restricting element being configured to restrict contraction of the contraction-restricted portion of the implant structure during contraction of a remaining portion of the implant structure by the contracting member.

For some applications, the implant is configured for implantation along a native annulus of a native atrioventricular valve of a patient in a manner in which at least the contraction-restricted portion of the implant structure is disposed along a portion of the annulus in a vicinity of a trigone of the valve, and the contraction-restriction element is coupled to the contraction-restricted portion.

For some applications, the apparatus further includes a contracting mechanism coupled to the implant structure and configured to contract at least a contraction-facilitated portion of the implant structure.

For some applications, the contracting mechanism is disposed at a first portion of the implant structure, and the contracting member extends along the implant structure toward the second end of the sleeve.

There is additionally provided, in accordance with some applications of the present invention, a method, including:

positioning an annuloplasty structure along an annulus of an atrioventricular valve of a subject, the implant structure including a sleeve;

fastening the annuloplasty structure to the annulus;

while the annuloplasty structure is in a fastened state with respect to the annulus, coupling at least one contraction-restricting element to at least one contraction-restricted portion of the annuloplasty structure; and subsequently, contracting at least one contraction-facilitated portion of the annuloplasty structure, the contraction-restricting element restricting contraction of the contraction-restricted portion during the contracting.

For some applications, coupling the contraction-restricting element to the contraction-restricted portion of the annuloplasty structure includes coupling the contraction-restricting element to a portion of the annuloplasty structure disposed along a portion of the annulus at a posterior leaflet of the valve.

For some applications, coupling the contraction-restricting element to the contraction-restricted portion of the annuloplasty structure includes coupling the contraction-restricting element to an outer surface of the annuloplasty structure.

For some applications, coupling the contraction-restricting element to the contraction-restricted portion of the annuloplasty structure includes restricting contraction of the contraction-restricted portion of the annuloplasty structure while facilitating radial movement of the contraction-restricted portion of the annuloplasty structure.

For some applications, positioning the annuloplasty structure along the annulus of the atrioventricular valve includes positioning the annuloplasty structure in a manner in which the contraction-restricted portion of the annuloplasty structure is disposed along a portion of the annulus at a posterior leaflet of the valve, and coupling the contraction-restricting element to the contraction-restricted portion of the annuloplasty structure includes restricting contraction of the contraction-restricted portion of the annulus at the posterior leaflet of the valve.

For some applications, coupling the contraction-restricting element to the contraction-restricted portion of the annuloplasty structure includes advancing into at least a portion of a lumen of the sleeve of the annuloplasty structure, a segment having at least a portion thereof that is non-compressible along a longitudinal axis of the segment.

For some applications, advancing the segment into the portion of the lumen of the sleeve includes advancing a segment that is disposed adjacently to one or more portions that are compressible along the longitudinal axis of the segment.

For some applications, advancing the segment into the portion of the lumen of the sleeve includes restricting contraction of the contraction-restricted of the annuloplasty structure while facilitating radial movement of the contraction-restricted portion of the annuloplasty structure.

For some applications, advancing the segment into the portion of the lumen of the sleeve includes advancing a coiled segment into the portion of the sleeve.

For some applications, the method further includes, prior to advancing the coiled segment within the sleeve, advancing the coiled segment toward the sleeve in a generally straightened configuration, and advancing the coiled segment into the portion of the sleeve includes allowing the segment to form a coil within the sleeve.

For some applications, fastening the annuloplasty structure to the annulus includes:

removably positioning a deployment manipulator tube through the opening and at least partially within the lumen of the sleeve of the annuloplasty structure, such that the deployment manipulator tube extends out of the at least one end of the sleeve; and driving one or more tissue anchors through a wall of the sleeve from within the lumen of the sleeve.

For some applications:

driving the one or more anchors includes advancing through the deployment manipulator tube an anchor driver that is reversibly couplable to the one or more anchors, exposing a distal end of the anchor driver from within a distal end of the deployment manipulator tube; and deflecting through the sleeve the distal end of the anchor driver.

For some applications, the method further includes maintaining relative positioning of the annuloplasty structure relative to the manipulator tube during the deflecting by applying a force to one or more stiffening elements that are threaded through the sleeve of the annuloplasty structure.

For some applications, coupling the contraction-restricting element to the contraction-restricted portion includes coupling the contraction-restricting element to a portion of the annuloplasty structure that is between 3 and 45 mm from at least one end of the sleeve, while facilitating contraction of the contraction-facilitated portion of the annuloplasty structure.

For some applications:

the at least one end of the sleeve defines a first free end of the annuloplasty structure, the annuloplasty structure defines a second free end, and fastening the annuloplasty structure to the annulus includes:

fastening the first free end of the of the annuloplasty structure to the portion of the atrial wall by fastening the contraction-restricted portion of the annuloplasty structure to the portion of the atrial wall, fastening the contraction-facilitated portion of the annuloplasty to a posterior portion of the annulus between the first and second trigones, and contracting the first portion of the annuloplasty structure includes contracting the contraction-facilitated portion of the annuloplasty structure that is between the first and second trigones.

For some applications:

the at least one end of the sleeve defines a first free end of the annuloplasty structure, the annuloplasty structure defines a second free end, and fastening the annuloplasty structure to the annulus includes:

fastening the annuloplasty structure to a first trigone of the valve by fastening the annuloplasty structure to the valve in a vicinity of the first free end; and fastening the annuloplasty structure to a second trigone of the valve by fastening the annuloplasty structure to the valve in a vicinity of the second free end.

For some applications:

fastening the annuloplasty structure to the first trigone includes fastening the first free end of the of the annuloplasty structure to the first trigone, fastening the annuloplasty structure to the second trigone includes fastening the second free end of the of the annuloplasty structure to the second trigone, fastening the annuloplasty structure to the annulus includes fastening the entire annuloplasty structure along the annulus between the first and second trigones, and contracting the contraction-facilitated portion of the annuloplasty structure includes contracting a portion of the annuloplasty structure that is between the second end and the contraction-restricted portion of the annuloplasty structure.

For some applications:

fastening the annuloplasty structure to the first trigone includes:

fastening the first free end of the of the annuloplasty structure to a portion of an atrial wall of a heart of the subject, and fastening a portion of the annuloplasty structure that is adjacent to the first free end to the first trigone, and fastening the annuloplasty structure to the second trigone includes fastening the second free end of the of the annuloplasty structure to the second trigone.

For some applications:

the atrioventricular valve includes a mitral valve;

the annuloplasty structure is shaped so as to define a first end and a second end, and positioning the annuloplasty structure along the annulus includes:

positioning the first end of the annuloplasty structure at a first trigone of the mitral valve; and positioning the second end of the annuloplasty structure at a second trigone of the mitral valve.

For some applications, contracting the first portion of the annuloplasty structure includes drawing the first and second ends of the annuloplasty structure toward one another.

For some applications, fastening includes:

anchoring a first location of annuloplasty structure to a first trigone of the valve; and anchoring a second location of the annuloplasty structure to a second trigone of the valve.

For some applications, anchoring the first location includes anchoring a first free end of the annuloplasty structure to the first trigone, and anchoring the second location includes anchoring a second free end of the annuloplasty structure to the second trigone.

The present invention will be more fully understood from the following detailed description of embodiments thereof, taken together with the drawings, in which:

BRIEF DESCRIPTION OF THE DRAWINGS

FIG. 1 is a schematic illustration of an implant structure comprising a sleeve having at least one end flap and a contracting mechanism, in accordance with some applications of the present invention;

FIG. 2 is a schematic illustration of an anchor deployment manipulator that facilitates deployment of one or more anchors through the sleeve of the implant structure of FIG. 1, in accordance with some applications of the present invention;

FIGS. 3A-3C are schematic illustrations of the anchor deployment manipulator of FIG. 2 advancing and deploying anchors from within the sleeve of the implant structure of FIG. 1, in accordance with some applications of the present invention;

FIGS. 6A-B show individual components of a contracting mechanism, in accordance with some applications of the present invention;

FIGS. 8A-C are schematic illustrations of a procedure for implanting the implant structure of FIG. 1 to treat a mitral valve, in accordance with some applications of the present invention;

FIG. 9 is a schematic illustration of the deployment of one of the tissue anchors into cardiac tissue, in accordance with some applications of the present invention;

FIGS. 10A-E are schematic illustrations of coupling of a contraction-restricting element to an implant structure configured to treat the mitral valve, in accordance with some applications of the present invention;

FIGS. 11A-D are schematic illustrations of coupling of a contraction-restricting element to the implant structure of FIGS. 10A-E, in accordance with another application of the present invention;

FIGS. 14A-B are schematic illustrations of an implant structure comprising a sleeve having at least one opening and a closure mechanism for the opening in accordance with some applications of the present invention; and FIGS. 15A-C are schematic illustrations of an anchor, in accordance with some applications of the present invention.

DETAILED DESCRIPTION OF EMBODIMENTS

Figure 3C:
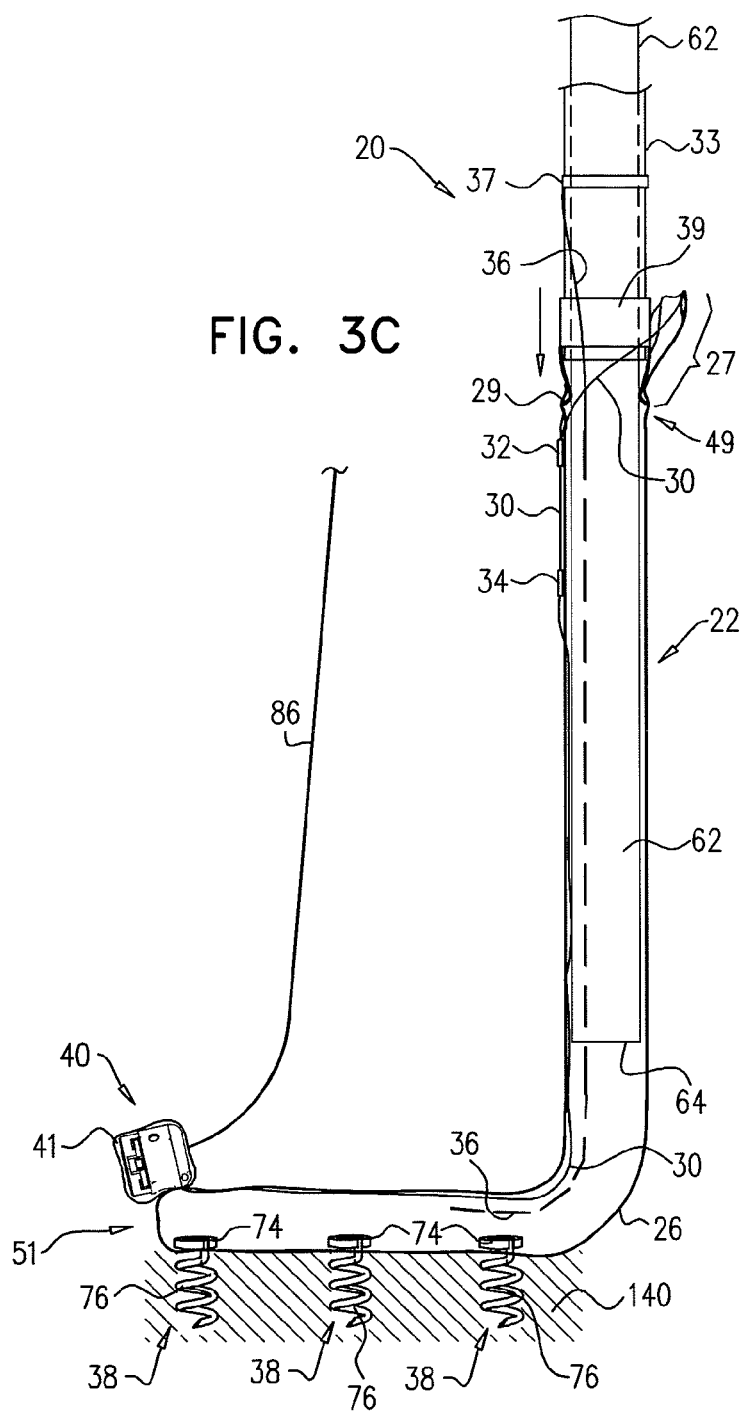

FIGS. 1 and 2 are schematic illustrations of a system 20 for repairing a dilated atrioventricular valve, such as a mitral valve, in accordance with some applications of the present invention. System 20 comprises an adjustable implant structure 22, shown alone in FIG. 1 in a non-contracted state, and an anchor deployment manipulator 60, shown alone in FIG. 2. For some applications, implant structure 22 comprises an annuloplasty ring, e.g., a partial annuloplasty ring. Implant structure 22 comprises a flexible sleeve 26. At least a distal portion of anchor deployment manipulator 60 is advanceable within sleeve 26, as shown hereinbelow, and, from within the sleeve, deploys a plurality of tissue anchors through a wall of the sleeve into cardiac tissue, thereby anchoring or otherwise fastening implant structure 22 around at least a portion of the valve annulus. Typically, sleeve 26 has a length of between 50 mm and 150 mm (e.g., between 70 mm and 120 mm), and a diameter of between 1 mm and 10 mm (e.g., between 2.5 mm and 3.5 mm).

Sleeve 26 is typically configured to be placed only partially around the valve annulus (i.e., to assume a C-shape), and, once anchored in place, to be contracted so as to circumferentially tighten the valve annulus. Alternatively, implant structure 22 is configured to be placed entirely around the valve annulus. In order to tighten the annulus, implant structure 22 comprises a contracting mechanism 40 that actuates a flexible elongated contracting member 30 which extends along implant structure 22. As shown, contracting member 30 is threaded one or more times through sleeve 26. For applications in which implant structure 22 comprises a partial annuloplasty ring as shown, sleeve 26 comprises first and second free ends 49 and 51, respectively (i.e., proximal and distal ends 49 and 51, respectively). First free end 49 is shaped so as to define an opening 25 for passage therethrough of manipulator 60 into a lumen of sleeve 26. First free end 49 is shaped so as to provide a first end flap 27 which is coupled to (e.g., by being looped through) a portion of contracting member 30. When contracting mechanism 40 is actuated, contracting member 30 is pulled or released in order to close or open flap 27 over opening 25. Thus, implant structure 22 comprises a closure element (e.g., closure mechanism 290) for closing opening 25. For such an application, closure mechanism 290 comprises flap 27 and the portion of contracting member 30 coupled thereto. Typically, closure mechanism 290 is remotely-controlled by the operating physician.

(In this context, in the specification and in the claims, "proximal" means closer to the orifice through which system 20 is originally placed into the body of the patient, and "distal" means further from this orifice.)

Following the closing of flap 27 over opening 25, contracting mechanism 40 facilitates contracting of implant structure 22. Contracting mechanism 40 is described in more detail hereinbelow. In addition, system 20 comprises a plurality of tissue anchors, typically between about 5 and about 20 anchors, such as about 10 or about 16 anchors. The anchors are configured to be deployed through the wall of sleeve 26 by anchor deployment manipulator 60. The insertion of the anchors into the sleeve and deployment of the anchors into cardiac tissue is described in detail hereinbelow.

It is noted that although closure element is shown in FIG. 1 as including closure mechanism 290, the scope of the present invention includes using other closure elements for closing opening 25. For example, a plug (such as a silicone plug) may be used to close the opening. Or, an elastomeric band (such as a silicone band) may be configured to automatically close the opening, upon removal of the manipulator therefrom. Or, flap 27 may be folded over and an anchor (e.g., a tissue anchor 38, as described herein) may be used to anchor the folded-over flap to the patient's tissue.

Typically, the closure elements described herein reduce the likelihood of a thrombosis forming inside sleeve 26, by closing opening 25, relative to if opening 25 were left opened. Alternatively or additionally, the closure elements described herein are used to close opening 25 for a different reason.

Typically, the closure of opening 25 (e.g., using the closure elements described herein) and the deployment of implant structure 22 is performed during a single procedure, e.g., by deploying the implant structure and closing opening 25 via a single catheter. For some applications (not shown), sleeve 26 defines openings 25 at first and second ends thereof, and closure elements are used to close the openings at the first and second ends of the sleeve.

Flexible sleeve 26 may comprise a braided, knitted, or woven mesh or a tubular structure comprising ePTFE. For some applications, the braid comprises metal and fabric fibers. The metal fibers, which may comprise Nitinol for example, may help define the shape of the sleeve, e.g., hold the sleeve open to provide space for passage and manipulation of deployment manipulator 60 within the sleeve. The fabric fibers may promote tissue growth into the braid. Optionally, the sleeve is somewhat elastic, which gives the sleeve a tendency to longitudinally contract, thereby helping tighten the sleeve. For example, the sleeve may be bellows-shaped or accordion-shaped.

Reference is now made to FIGS. 1, 2, 8A-C and 9, which are schematic illustrations of a procedure for implanting implant structure 22 to repair a mitral valve, in accordance with some applications of the present invention. Typically, the sleeve is configured to have a tendency to assume a straight shape. This straightness helps the surgeon locate the next site for each subsequent anchor during the implantation procedure, as described hereinbelow with reference to FIGS. 8A-C. For example, because sleeve 26 assumes a generally straight shape, the sleeve may help provide an indication of distance between adjacent anchoring sites.

As shown, sleeve 26 is configured to have a controllably variable stiffness. For example, one or more generally stiff stiffening elements 36 (shown in FIG. 1), e.g., a wire or a suture, is threaded one or more times (e.g., a plurality of times) through sleeve 26 to provide the stiffness, and subsequently be removed at the conclusion of the implantation procedure when the stiffness is no longer useful, as is described hereinbelow. Since manipulator 60 and components that are slidable therein are deflectable and steerable, stiffening element 36 helps maintain the relative positioning of manipulator 60 with respect to sleeve 26 in order to present manipulator 60 from deploying an anchor through sleeve 26 in a vicinity of contracting member 30. That is, stiffening element 36 helps maintain the shape and integrity of structure 26 (i.e., prevents flailing of sleeve 26). For some applications, element 36 is pulled directly by an operating physician. For other applications, element 36 is coupled to a portion of manipulator 60 or a component that is slidable within a lumen of manipulator 60, and is pulled either by the manipulator or any component thereof. Stiffening element 36 helps ensure that the anchors are deployed through sleeve 26 without interfering with contracting member 30.

Elongated contracting member 30 comprises a wire, a ribbon, a rope, or a band, which typically comprises a flexible and/or superelastic material, e.g., nitinol, polyester, stainless steel, or cobalt chrome. For some applications, the wire comprises a radiopaque material. For some applications, contracting member 30 comprises a braided polyester suture (e.g., Ticron). For some applications, contracting member 30 is coated with polytetrafluoroethylene (PTFE). For some applications, contracting member 30 comprises a plurality of wires that are intertwined to form a rope structure.

By being threaded or sewn through sleeve 26, contracting member 30 is positioned at least partially within a lumen of the sleeve 26 alternately inside and outside of the sleeve along the length of the sleeve. Optionally, sleeve 26 defines an internal channel within which member 30 is positioned (configuration not shown). Alternatively, the contracting member is disposed outside the lumen of the sleeve, such as alongside an outer wall of the sleeve. For example, sleeve 26 may define an external channel within which member 30 is positioned, or the sleeve may comprise or be shaped so as to define external coupling elements, such as loops or rings (configuration not shown). For some applications, contracting member 30 is positioned approximately opposite the portion of sleeve 26 through which the anchors are deployed, as described hereinabove.

For some applications of the present invention, contracting mechanism 40 comprises a rotatable structure, such as a spool. The rotatable structure is arranged such that rotation thereof contracts implant structure 22. For some applications, a first end portion of contracting member 30 is coupled to the spool (e.g., by being looped through a portion of the spool). For some applications, contracting mechanism 40 further comprises a housing 44 that houses the rotatable structure, e.g., the spool. A braided fabric mesh 41 surrounds housing 44 so as to facilitate implantation thereof and induce fibrosis around housing 44. The spool is positioned in a vicinity of (e.g., within 1 cm of) end 51 of sleeve 26, as shown. As shown, a second end portion of contracting member 30 is coupled to sleeve 26 in a vicinity of (e.g., within 0.5 cm of) end 49 of the sleeve 26, opposite end 51 to which the contracting mechanism 40 is positioned. Typically, contracting mechanism 40 is sutured to sleeve 26 by coupling threads 31.

In the configuration shown, the second end portion of contracting member 30 is looped through a portion of flap 27 and extends back toward end 51 of sleeve 26. The second end portion of contracting member 30 is coupled to sleeve 26 in a vicinity of first end 49 of the sleeve at a distance of between 0.2 cm and 2 cm from end 49. Since contracting member 30 is looped through a portion of contracting mechanism 40, the free ends of contracting member 30 are brought together, and together serve as the second end portion of contracting member 30. Alternatively, contracting member 30 is not looped through a portion of contracting mechanism 40, a first end of contracting member 30 is fixedly coupled to contracting mechanism 40, while a second end of contracting member 30 defines the second end portion that is coupled to the portion of sleeve 26.

The second end portion of member 30 is coupled to sleeve 26 by contraction-restricting elements 200, e.g., crimping elements 32 and 34. Crimping elements 32 and 34 restrict contraction of a contraction-restricted portion 52 of sleeve 26 that has a length of between 5 mm and 30 mm. For some applications, the crimping elements are disposed such that the contraction-restricted portion of the sleeve is between 3 and 45 mm from one end of the sleeve. The remaining portion of sleeve 26, i.e., a contraction-facilitated portion 53 is contractible and expandable in response to respective tightening or loosening of contracting member 30 responsively to the actuation of contracting mechanism 40. Thus, while contraction of implant structure 22 is being ongoing (i.e., while contraction-facilitated portion 53 is being contracted), contraction-restricted portion 52 is restricted from being contracted. For some applications, contraction-restriction portions, each having a length of between 5 mm and 30 mm are disposed, are disposed in the vicinity of both ends of sleeve 26.

Rotation of the spool of contracting mechanism 40 in a first rotational direction winds a portion of contracting member 30 around the spool, thereby pulling the far end of implant structure 22 toward the spool and shortening and tightening implant structure 22.

Alternatively, in some configurations, contracting mechanism 40 is positioned at an intermediary position along the sleeve, rather than in a vicinity of one of the ends. For these configurations, contracting member 30 comprises two contracting members, which are respectively connected to the two ends of the sleeve, and both of which are connected to the spool. Rotating the spool contracts both contracting members. These configurations may be implemented using techniques described in U.S. patent application Ser. No. 12/341,960 to Cabiri (published as US 2010/0161047), which is incorporated herein by reference, with reference to FIG. 15 thereof.

For other applications, contracting member 30 comprises at least one wire (e.g., exactly one wire) that passes through a coupling mechanism of the spool of contracting mechanism 40, in order to couple the wire to the spool. As described hereinabove, the free ends of contracting member 30 are brought together, and together serve as the second end portion of contracting member 30, and may be coupled to one of the several locations of sleeve 26 mentioned hereinabove. In this configuration, approximately the longitudinal center of the wire serves as first end of the contracting member.

FIG. 2 shows manipulator 60 comprising an elongate outer tube 62 (sometimes referred to herein, including in the claims, as a "deployment manipulator tube") having a tube lumen and a distal end 64 which defines an opening for passage therethrough of the one or more anchors. Typically, the one or more anchors are coupled to an anchor driver (as described hereinbelow) which slides through the lumen of manipulator 60. A proximal pushing tube 33 slides along tube 62 of manipulator 60. A distal end of pushing tube 33 is coupled to a coupler 39 which increases friction at a distal end of pushing tube 33 so as to facilitate a sliding of pushing tube 33 along tube 62 of manipulator 60, while temporarily maintaining the distal end of pushing tube 33 in place with respect to tube 62 of manipulator 60. Coupler 39 comprises one or more (e.g., two, as shown) coupling elements 29 which are configured to removably couple the distal end of pushing tube 33 to proximal end 49 of sleeve 26, as described hereinbelow. Coupling elements 29 hold sleeve 26 surrounding deployment manipulator 60.

FIGS. 3A-C are schematic illustrations of manipulator advanced into a lumen of sleeve 26 of implant structure 22 in order to deploy one or more tissue anchors 38, in accordance with some applications of the present invention. Anchor deployment manipulator 60 is advanced into a lumen of sleeve 26, and, from within the lumen, deploys anchors 38 through a wall of the sleeve and into cardiac tissue, thereby anchoring the sleeve around a portion of the valve annulus. Typically, implant structure 22 and anchor deployment manipulator 60 are introduced into the heart via a sheath 104, as described hereinbelow with reference to FIGS. 8A-C.

As shown in FIG. 3B, an anchor driver 68 is slidable within a lumen of tube 62 of manipulator 60. Anchor driver 68 is coupled at a distal end thereof to a driving interface 69 that is either male (e.g., comprising a screwdriver head, having, such as a slot-head, an Allen-head, a Phillips-head, a Robertson-head, or a hex-head) or female (e.g., comprising a wrench head, having, for example, a square or hex opening), as appropriate for the driving interface provided. Anchor driver 68 is steerable and deflectable independently of the steerability and deflectability of tube 62 of manipulator 60.

For some applications, at least one of anchors 38 is deployed from a distal end 64 of deployment manipulator 60 while the distal end is positioned such that a central longitudinal axis 62 through distal end 60 of deployment manipulator 60 forms an angle of between about 45 and 90 degrees with the wall of sleeve 26 at the point at which the anchor penetrates the wall, such as between about 75 and 90 degrees, e.g., about 90 degrees (as shown hereinbelow with reference to FIGS. 8A-C). For other applications, as shown in FIG. 3B, at least one of anchors 38 is deployed from driving interface 69 while interface 69 is positioned such that a central longitudinal axis through the distal end of interface 69 forms an angle of between about 45 and 135 degrees with the wall of sleeve 26 at the point at which the anchor penetrates the wall, such as between about 75 and 100 degrees, e.g., about 90 degrees. Thus, manipulator 60 has steerability and anchor driver 68 has steerability that is independent from the steerability of manipulator 60. For some applications of the present invention, the steerability of manipulator 60 is in a different plane than the steerability of anchor driver 68.

This anchor-penetration point is typically at a portion of the sleeve that extends distally beyond distal end 64 of deployment manipulator 60. Typically, all of the anchors are deployed at such angles, with the possible exception of the first anchor deployed near the distal end of the sleeve.

Reference is now made to FIG. 3B. As shown, deployment manipulator 60 comprises outer tube 62 and anchor driver 68 which is at least partially positioned within tube 62. Anchor driver 68 comprises an elongated, flexible shaft 70, having at its distal end a driver head 72. Rotation of anchor driver 68 screws anchors 38 into the cardiac tissue. Each of anchors 38 is shaped so as to define a coupling head 74 and a tissue coupling element 76. The anchors are typically rigid. Tissue coupling elements 76 may, for example, be helical or spiral in shape (e.g., having the shape of a corkscrew), as shown in the figures, may comprise screws, or may have other shapes. Coupling heads 74 may be either male (e.g., a hex or square protrusion) or female (e.g., a straight slot, a hex opening, a Phillips opening, or a Robertson opening). The use of helical anchors, which are screwed into the cardiac tissue, generally minimizes the force that needs to be applied during deployment of the anchors into the cardiac tissue. Alternatively, the anchors may comprise staples, clips, spring-loaded anchors, or other tissue anchors described in the references incorporated hereinabove in the Background section, or otherwise known in the art.

For some applications, outer tube 62 of deployment manipulator 60 is steerable, as known in the catheter art. To provide steering functionality to deployment manipulator 60, outer tube 62 typically comprises one or more steering wires, the pulling and releasing of which cause deflection of the distal tip of the tube.

For some applications of the present invention, each of tissue coupling elements 76 is shaped so as to define a longitudinal axis 78 (shown in FIG. 3B), and is configured to penetrate the cardiac tissue in a direction parallel to longitudinal axis 78. Deployment manipulator 60 is configured to deploy tissue coupling element 76 from distal end 64 of the deployment manipulator through the wall of sleeve 26 in a direction parallel to longitudinal axis 78 and parallel to a central longitudinal axis 65 through distal end 64 of deployment manipulator 60 (axis 65 is shown hereinbelow in FIG. 9).

For some applications, the plurality of anchors are applied using the deployment manipulator by loading a first one of the anchors onto the anchor driver, and deploying the anchor into the cardiac tissue. The anchor driver is withdrawn from the patient's body (typically while leaving outer tube 62 of the deployment manipulator in place in the sleeve), and a second one of the anchors is loaded onto the anchor driver. The anchor driver is reintroduced into the outer tube of the deployment manipulator, and the second anchor is deployed. These steps are repeated until all of the anchors have been deployed. Alternatively, the entire deployment manipulator, including the anchor driver, is removed from the body and subsequently reintroduced after being provided with another anchor. Techniques for use with the refillable deployment manipulator may be practiced in combination with techniques described in U.S. patent application Ser. No. 12/689,635 to Zipory et al. (published as US 2010/0280604), entitled, "Over-wire rotation tool," filed Jan. 19, 2010, which is incorporated herein by reference, and with techniques described in PCT Patent Application PCT/IL2010/000358 to Zipory et al. (published as WO 10/128503), entitled, "Deployment techniques for annuloplasty ring," filed May 4, 2010, which is incorporated herein by reference. Further alternatively, the deployment manipulator is configured to simultaneously hold a plurality of anchors, and to deploy them one at a time.

Reference is again made to FIGS. 3A-C. FIG. 3A shows the slidable advancement of manipulator 60 through the lumen of sleeve 26 of implant structure 22. Manipulator 60 slides proximally from distal end 51 of sleeve 26 in order to facilitate implantation of anchors 38 within cardiac tissue of the patient. As shown in FIG. 3B, a first tissue anchor 38 is implanted in a vicinity of end 51 (e.g., at end 51 as shown). Anchor 38 is implanted when anchor driver 68 is rotated in order to corkscrew anchor 38 into the tissue. Following the anchoring of anchor 38 in the vicinity of end 51, manipulator 60 is withdrawn proximally so as to anchor a second anchor 38 into cardiac tissue.

Typically, the first anchor 38 is deployed most distally in sleeve 26 (generally at or within a few millimeters of end 51 of sleeve 26), and each subsequent anchor is deployed more proximally, such that sleeve 26 is gradually pulled off (i.e., withdrawn from) deployment manipulator 60 in a distal direction during the anchoring procedure. Typically, as the sleeve is pulled off the deployment manipulator, the deployment manipulator is moved generally laterally along the cardiac tissue, as shown in FIGS. 3B-C.

The pushing of sleeve 26 distally from manipulator 60 is facilitated by pushing tube 33. Pushing tube 33 passes over outer tube 62 of manipulator 60, and pushes gently in a distal direction on proximal end 49 of sleeve 26. The pusher tube is held in place against proximal end 49 of sleeve 26, typically by an external control handle (not shown for clarity of illustration) that is coupled to respective proximal ends of manipulator 60, tube 62, anchor driver 68, and pushing tube 33. As sleeve 26 is pulled off (i.e., withdrawn from) outer tube 62 of deployment manipulator 60, pushing tube 33 pushes sleeve 26 distally with respect to outer tube 62, helping withdraw the sleeve from the outer tube. If the pusher tube were not provided, the wall of sleeve 26 might snag on outer tube 62 (as mentioned above, the sleeve may comprise braided or woven fabric). In addition, if such snagging occurs, gentle pushing with the pusher tube in the distal direction may help free the snag.

In the configuration shown in FIG. 3A, pushing tube 33 comprises one or more coupling elements 29 (such as exactly one coupling element or exactly two coupling elements) at a distal end of tube 38. Coupling elements 29 are configured to removably couple proximal end 49 of sleeve 26 to the distal end of pushing tube 33, thereby allowing sleeve 26 from moving distally with respect to outer tube 62 of deployment manipulator 60 only to the extent that pushing tube 33 is released in the distal direction (as indicated by the downward arrow in FIG. 3B), such as using the external control handle, while manipulator 60 is pulled proximally. Alternatively, both pushing tube 33 and manipulator are pulled proximally (e.g., by pulling proximally the external control handle) and pushing tube 33 thereby applies a passive counter force in order to resist proximal end 49 of sleeve 26 in a manner in which, responsively to the passive force, proximal end 49 of sleeve 26 is advanced distally.

For some applications, coupling elements 29 have a natural tendency to flex inwards (toward a central longitudinal axis of sleeve 26 that passes through the proximal end of the sleeve). Outer tube 62, when positioned within the sleeve in a vicinity of the coupling elements, pushes the coupling elements outwards (away from the central longitudinal axis), causing the coupling elements to engage the sleeve. For example, the coupling elements may be curved to define outwardly-directed ends that push against or pierce the sleeve. Such pushing against or piercing engages the sleeve, which, as mentioned above, may comprise braided or woven fabric.

During the anchoring procedure, stiffening element 36 maintains relative dispositions of manipulator and/or anchor driver 68 with respect to sleeve 26. As shown, stiffening element 36 is threaded along sleeve 26. The relative stiffness of stiffening element to the flexibility of sleeve 26 maintains sleeve 26 in a relative spatial configuration in which contracting member 30 remains above tube 62 of manipulator 60 and/or anchor driver 68. In such a manner, stiffening element 36 helps ensure that anchors 38 do not interfere with contracting member 30 and that the portion of sleeve 26 that is opposite contracting member 30 is anchored to the annulus. Stiffening element 36 is loosely coupled (i.e., is not fixed by being knotted or otherwise fastened) to a distal end 35 thereof (shown in FIG. 3A) to a distal portion of sleeve 26 in a vicinity of end 51 of sleeve 26. A proximal end of stiffening element 36 is coupled to a coupler 37 (or a ring) which is coupled to pushing tube 33. As sleeve 26 is slid gradually distally from outer tube 62 of manipulator 60, as described hereinabove, since coupler 37 is fixed to pushing tube 33, the successive distal portions of stiffening element 36 are decoupled, by being unthreaded, from sleeve 26 responsively to the distal sliding of sleeve 26 from tube 62 of manipulator 60.

FIG. 3C shows anchoring of an additional tissue anchor 38 to the annulus of the valve. As described hereinabove, with each successive anchor 38 that is deployed, successive portions of sleeve 26 are slid of tube 62 of manipulator 60. For some applications, portions of stiffening element 36 are unthreaded from sleeve 26.

Following the anchoring of sleeve 26 by anchoring a suitable number of anchors around a desired portion of the annulus of the valve, sleeve 26 is slid off of manipulator 60 and decoupled from coupling elements 29 in order to release sleeve 26 from coupling elements 29. Proximal withdrawal of outer tube 62 from sleeve 26 (into or through pushing tube 33) allows coupling elements 29 to assume their natural inwardly-flexed position, thereby releasing sleeve 26 from the coupling elements, and decoupling the sleeve from the pusher tube. As described hereinabove, sleeve 26 is gradually pulled off (i.e., withdrawn from) deployment manipulator 60, including outer tube 62, in a distal direction during the anchoring procedure. Outer tube 62 of deployment manipulator 60 is proximally withdrawn completely from the sleeve at the conclusion of the anchoring procedure. The flexing of the coupling elements releases the sleeve at the conclusion of the procedure. As pushing tube 33 is decoupled from sleeve 26 and is withdrawn proximally, pushing tube 33 pulls on stiffening element 36 in order to entirely decouple, by unthreading stiffening element 36 from sleeve 26.

Figure 3D:
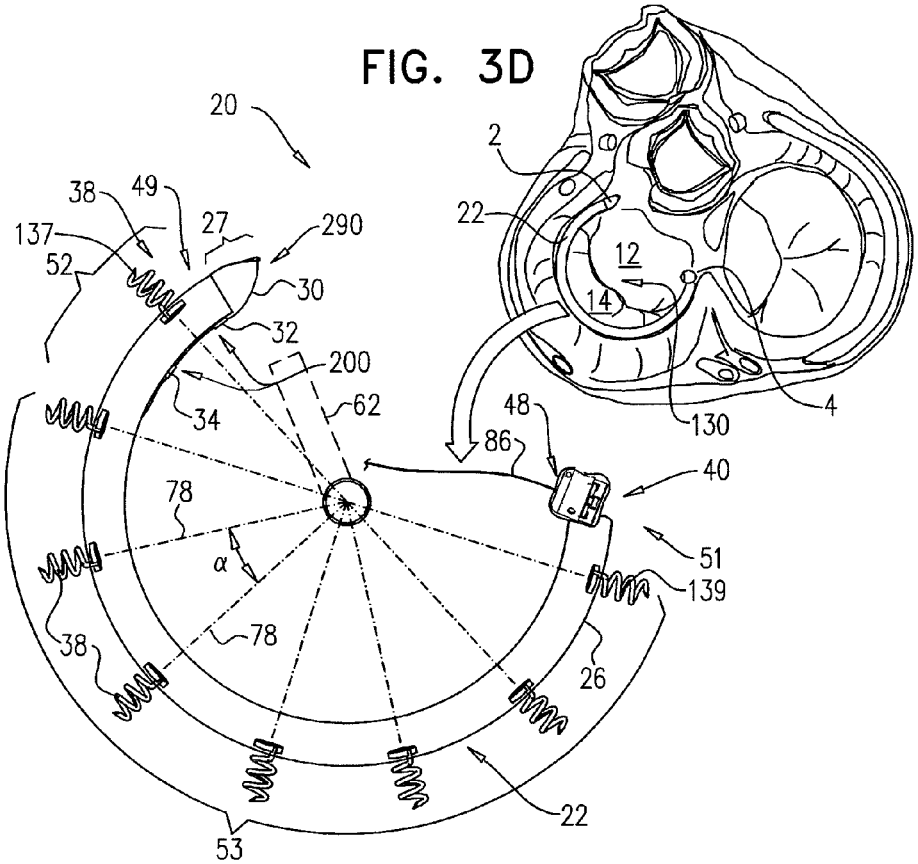
FIGS. 3D-E are schematic illustrations of the closing of the end flap of the implant structure following the anchoring of the structure to the annulus, in accordance with some applications of the present invention.

Reference is now made to FIG. 3D, which is a schematic illustration of implant structure 22 anchored to the annulus of a mitral valve 130 of the patient, in accordance with some applications of the present invention. A plurality of tissue anchors (e.g., 8 tissue anchors as shown by way of illustration and not limitation) anchor implant structure 22 to the annulus. As shown, in some applications of the present invention, first end 49 of structure 22 is anchored in a vicinity of a first trigone 2 (e.g., at first trigone 2) of valve 130 by a first anchor 137, and second end 51 of structure 22 is anchored in a vicinity of a second trigone 4 (e.g., at second trigone 4) of valve 130 by a second anchor 139. In such an embodiment in which first and second ends 49 and 51 are anchored to the annulus of the valve, both contraction-restricted portion 52 of sleeve 26 and contraction-facilitated portion 53 of sleeve 26 are disposed along a portion of the annulus that is between trigones 2 and 4 and along a junction of the annulus and a posterior leaflet 14 and portions of anterior leaflet 52. In such an application, since contraction-restricted portion 52 is disposed along the portion of the annulus, only a section of the portion of the annulus (i.e., the section along which contraction-facilitated portion 53 is disposed) is contracted by implant structure 22. For some applications, the sleeve defines two contraction-restricted portions 52, as described hereinabove. For such applications, typically upon implantation of the sleeve at the annulus, the contraction-restriction portions are disposed in the vicinity of trigones 2 and 4.

FIG. 3D shows implant structure 22 following extraction of manipulator 60 from within the lumen of sleeve 26. Immediately following the extraction of manipulator 60, flap 27 of closure mechanism 290 is disposed in an opened state, as shown. Additionally, implant structure 22 is shown in a non-contracted state having an angle α (alpha) between respective longitudinal axes 78 of successive anchors 38, angle α being between 10 degrees and 30 degrees.

As shown in FIGS. 1 and 3A-D, implant structure 22 comprises a contracting mechanism, such as contracting mechanism 40. Contracting mechanism 40 comprises a rotatable structure, arranged such that initial rotation of the rotatable structure in a first rotational direction in order to pull contracting member 30, closes flap 27 over the opening at end 49 of implant structure 22, and further rotation of the rotatable structure in the first rotational direction contracts at least a portion (e.g., the entire contraction-facilitated portion 53) of implant structure 22. It is to be noted that the rotatable structure is capable of being rotated bidirectionally such that following rotation of the rotatable structure in the first rotational direction in order to contract implant structure 22, the rotatable structure may be rotated initially in a second rotational direction that is opposite the first rotational direction, in order slacken contracting member 30 to expand at least a portion (e.g., the entire contraction-facilitated portion 53) of implant structure 22. In response to further rotation of the rotatable structure in the second rotational direction, flap 27 is opened. Implant structure 22 further comprises a longitudinal member 86, such as a wire, which is coupled to contracting mechanism 40 and passes out of the body of the patient.

Figure 3E:
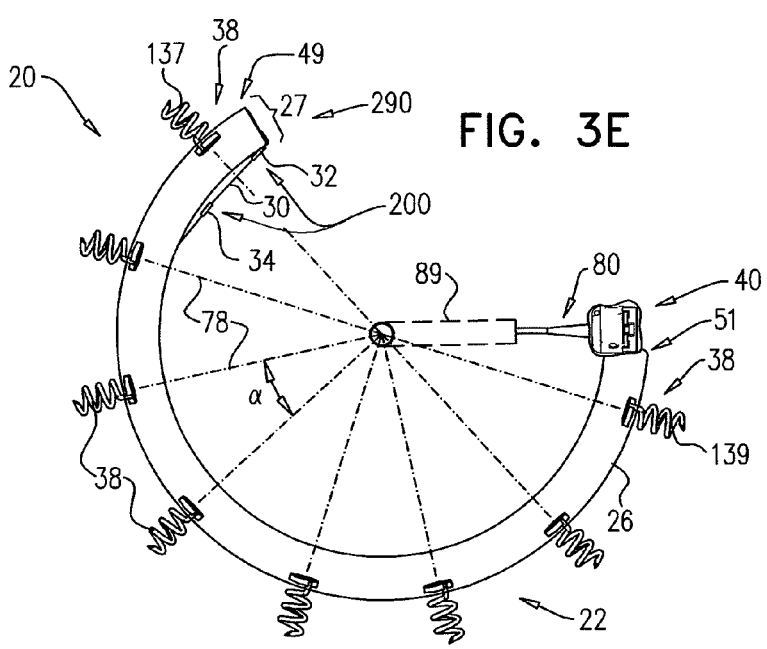
Figure 3F:
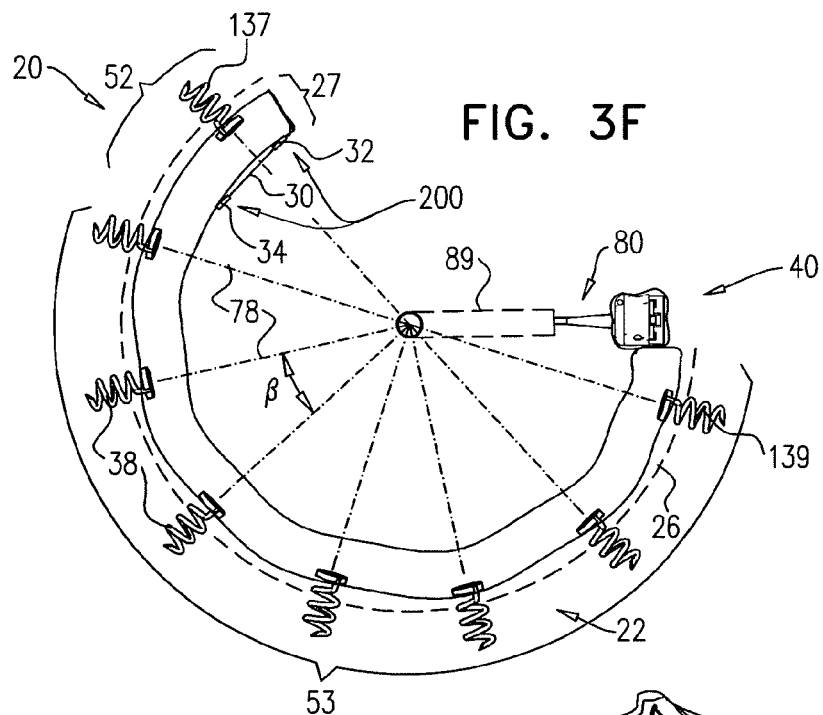
FIG. 3F shows contraction of at least part of the implant structure, in accordance with some applications of the present invention.

Reference is now made to FIGS. 3E-F, which are schematic illustrations of a rotation tool 80 used to facilitate contraction of implant structure 22 by actuating contracting mechanism 40. A tool, such as rotation tool 80, is provided for rotating the rotatable structure. Tool 80 is configured to be guided over longitudinal member 86, to engage the rotatable structure of contracting mechanism 40, and to rotate the rotatable structure in response to a rotational force applied to the tool.

Reference is now made to FIGS. 3D-E. As shown in FIG. 3D, contracting mechanism 40 is shaped so as to provide a driving interface 48 which facilitates coupling of rotation tool 80 to the rotatable structure of contracting mechanism 40. In order to readily bring the rotation tool to driving interface 48, rotation tool 80 is guided over (as shown in FIG. 3E) the longitudinal member, or alongside the longitudinal member (configuration not shown). Alternatively, longitudinal member 86 comprises a suture or other highly flexible element. For some applications, the longitudinal member comprises a tube, through which rotation tool 80 is passed to bring the tool to the driving interface 48. For some applications, longitudinal member 86 has a diameter of between 0.1 and 1 mm, such as 0.4 mm.

For some applications, longitudinal member 86 is looped through contracting mechanism 40, and both ends of the longitudinal member are brought together and extend outside of the patient's body. The longitudinal member is decoupled from the contracting mechanism by releasing one end of the longitudinal member, and pulling on the other end to draw the longitudinal member away from the contracting mechanism.

For some applications, contracting mechanism 40 is positioned in a vicinity of (e.g., within 1 cm of) distal end 51 of sleeve 26, and access to driving interface 48 is provided from outside sleeve 26, as shown in FIGS. 3E-F (in which the contracting mechanism is positioned in a vicinity of end 51 of the sleeve).

For some applications in which access to driving interface 48 is provided from outside sleeve 26, the rotation tool is initially removably attached to the driving interface, prior to the commencement of the implantation procedure, and is subsequently decoupled from the driving interface after the rotatable structure has been rotated. In these applications, contracting mechanism 40 may be positioned in a vicinity of distal end 51 or proximal end 49 of sleeve 26, or at an intermediate location along the sleeve. Optionally, at least a portion of a shaft of the rotation tool is positioned within a sheath 89 which advances through an access sheath that is disposed within the vasculature of the patient.

FIG. 3E shows implant structure 22 prior to contraction thereof. Contracting mechanism 40 is initially rotated in a first rotational direction so as to close flap 27 over the opening at end 49 of implant structure 22. As shown during the initial pulling of contracting member 30 by initial rotation of the rotatable structure of contracting mechanism 40, the angle between respective longitudinal axes 78 of successive anchors 38 remains angle α (alpha).

In FIG. 3F, contracting mechanism 40 is actuated further by rotation tool 80 in order to contract at least a portion of structure 22 (i.e., at least a portion or all of contraction-facilitated portion 53 of structure 22). As shown, an angle β (beta) between respective longitudinal axes 78 of successive anchors 38 of contraction-facilitated portion 53, angle β being between 5 degrees and 25 degrees, and being smaller than angle α (alpha) shown in FIGS. 3D-E. Additionally, as shown in FIG. 3F, sleeve 26 at contraction-facilitated portion 53 is shown as being in a contracted state (i.e., wavy, as shown), while sleeve 26 at contraction-restricted portion 52 is shown in a non-contracted state (i.e., straight, as shown).

Figure 4:
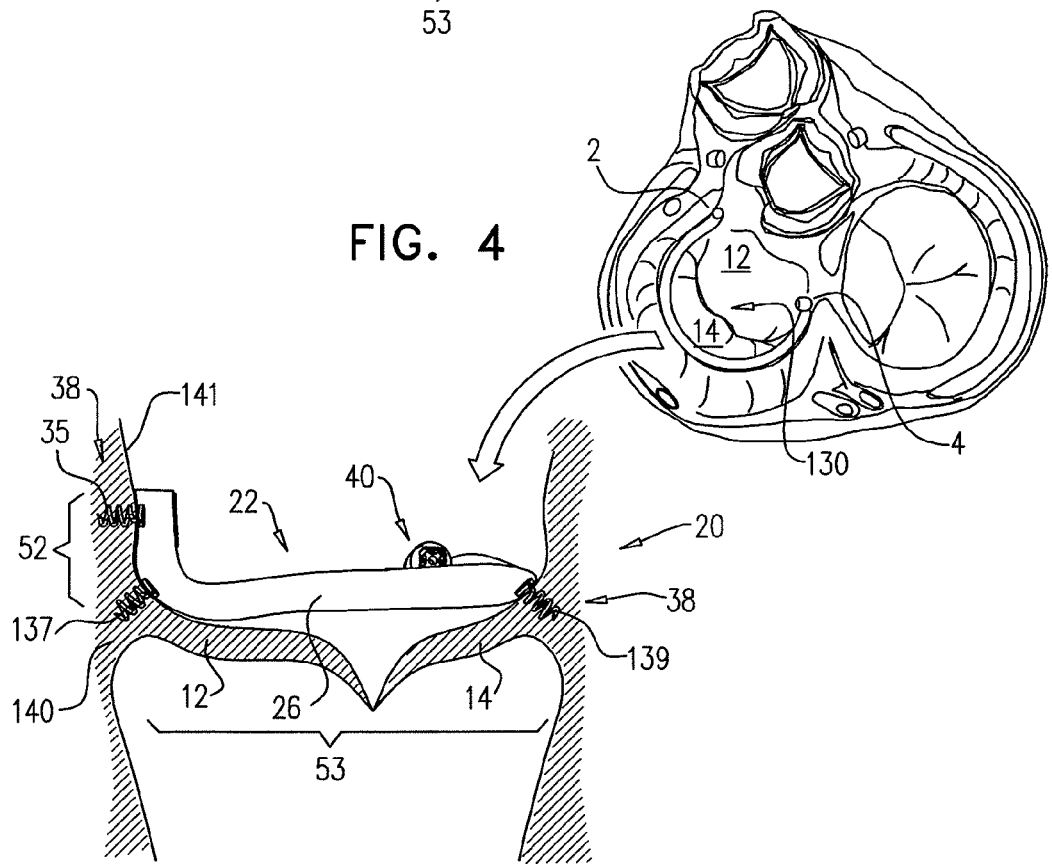
FIG. 4 is a schematic illustration showing a portion of the implant structure being coupled to a portion of an atrial wall of a heart of a patient; in accordance with some applications of the present invention.

Reference is now made to FIG. 4, which is a schematic illustration showing a portion of implant structure 22 being coupled to a portion of an atrial wall 141 of the heart of the patient, in accordance with some applications of the present invention. For some applications, a portion (e.g., the entire portion) of contraction-restricted portion 52 of is anchored to the portion of atrial wall 141. For such applications, the entire contraction-facilitated portion 53 may be coupled to the annulus of valve 130 along a portion of the annulus that is between trigones 2 and 4 and along a junction of the annulus and a posterior leaflet 14 and portions of anterior leaflet 12. In such an application, since contraction-restricted portion 52 is not disposed along the portion of the annulus, the entire portion of the annulus (i.e., the section along which contraction-facilitated portion 53 is disposed) is contracted by implant structure 22.

It is to be noted, as shown that first anchor 137 is anchored to the annulus in a vicinity of first trigone 2 (e.g., at first trigone 2), and second anchor 139 is anchored to the annulus in a vicinity of second trigone 4 (e.g., at second trigone 4).

Reference is now made to FIGS. 3D and 4. It is to be noted that implant structure 22, shown in either application in FIG. 3D or 4, has the same length when elongated along a longitudinal axis (i.e., when not formed into a curved structure, as shown). It is to be noted that anchoring structure to the annulus of valve 130 using either application as shown in FIG. 3D or 4 depends on the level of distention of valve 130 of a given patient. That is, for patients having a greater degree of distention, the entire structure 22 is coupled to the annulus along the portion thereof that is between first and second trigones 2 and 4, respectively, and along the junction of the annulus and posterior leaflet 14 and portions of anterior leaflet 12. For patients having a lesser degree of distention, excess portions of structure 22 may be anchored to the portion of atrial wall 141. It is to be noted that the portion of atrial wall 141 to which the portion of structure 22 is anchored may be a portion of a free wall of the atrium, as shown, or a portion of the interatrial septum (not shown). Typically, contraction-restricted portion 52 is anchored to the portion of atrial wall 141.

Figure 5:
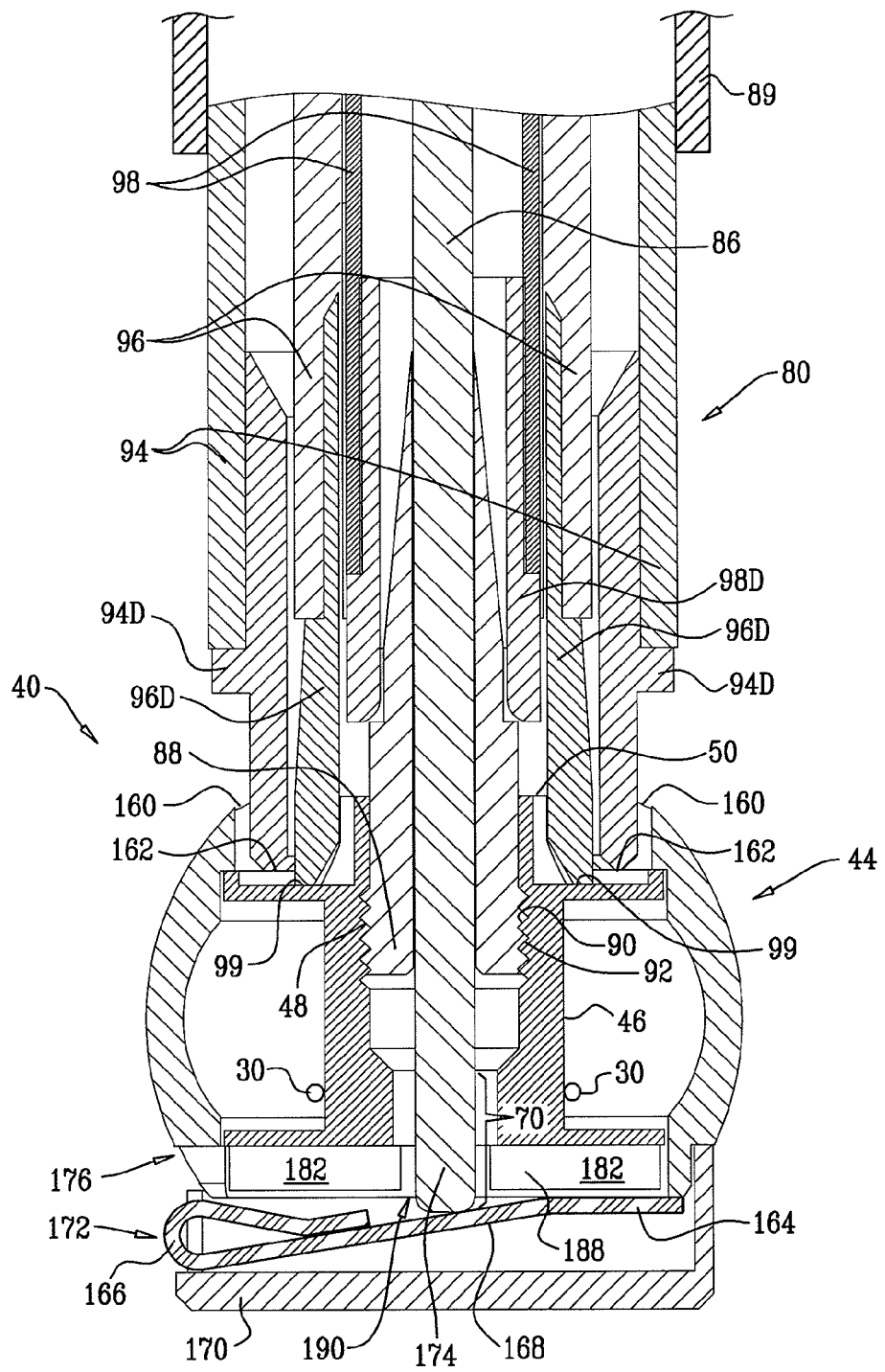
FIG. 5 is schematic cross-sectional illustration of a rotation tool being used to rotate a spool of a contracting mechanism of the implant structure of FIG. 10, in accordance with some applications of the present invention.

Reference is now made to FIG. 5, which is a schematic cross-sectional illustration of a configuration of rotation tool 80 being used to rotate the rotatable structure (e.g., a spool 46, as shown) of contracting mechanism 40 of implant structure 22, in accordance with some applications of the present invention. In this application, as in the configurations shown in FIGS. 1, 3A-F and 4, access to driving interface 48 is provided from outside sleeve 26. Contracting mechanism 40 comprises longitudinal member 86 that is attached to the contracting mechanism 40 and passes out of the body of the patient. In order to readily bring rotation tool 80 to driving interface 48, rotation tool 80 is guided over longitudinal member 86. In this application, rotation tool 80 comprises one or more tubes that pass over the longitudinal member, as described below.

As mentioned above, for some applications, longitudinal member 86 comprises a wire, which may comprise metal. Because the wire is fairly stiff, the wire generally maintains its direction and orientation with respect to contracting mechanism 40. The wire thus readily guides the tubes to the contracting mechanism such that the tubes have a desired orientation and position with respect to the contracting mechanism.

Longitudinal member 86 is removably coupled to contracting mechanism 40, typically to a central portion of an upper surface 50 of spool 46. For some applications, a distal portion 88 of longitudinal member 86 is shaped so as to define a screw thread 90 (i.e., a mechanical structure that is coupled to member 86 at a distal end portion thereof). Distal portion 88 is screwed into a threaded opening 92 of upper surface 50, in order to removably couple longitudinal member 86 to contracting mechanism 40. Typically, the distal portion is initially coupled to the contracting mechanism before implant structure 22 is placed into an atrium of the patient. As described below, the distal portion is decoupled from the contracting mechanism after spool 46 has been rotated to tighten implant structure 22. For some applications, distal portion 88 comprises a discrete element that is fixed to longitudinal member 86, while for other application, distal portion 88 is integral with longitudinal member 86.

For some applications, rotation tool 80 comprises an inner (first) tube 98, an intermediate (second) tube 96, and, optionally, an outer (third) tube 94. Rotation of each of the tubes is independently controlled, such as using techniques described in U.S. patent application Ser. No. 12/689,635 to Zipory et al. (published as US 2010/0280604), entitled, "Over-wire rotation tool," filed Jan. 19, 2010, which is incorporated herein by reference. For some applications, a distal portion of each of tubes 94, 96, and 98 that enters the patient's body comprises braided plastic, and a proximal portion of each of the tubes that does not enter the patient's body comprises a hard material, such as metal (not shown). For example, the distal and proximal portions may have lengths of between 50 and 100 cm and between 50 and 350 cm, respectively. Distal-most portions 94D, 96D, and 98D, respectively, of the distal portions typically comprise a hard material, such as metal, in order to engage other elements, as described immediately below. Typically, the distal-most portions comprise separate elements that are coupled to their respective tubes. For example, the distal-most portions may have lengths of between 1 and 10 mm.

Intermediate tube 96 is configured to rotate spool 46. To this end, intermediate tube 96 (such as distal-most portion 96D thereof) is configured to engage upper surface 50 of spool 46. To enable such engagement, the upper surface typically is shaped so as to define one or more indentations 99 (e.g., grooves), in which corresponding protrusions at the distal end of intermediate tube 96 are positioned, such as by gently rotating tube 96 (or all of the tubes) until such engagement occurs. (Spring may be provided to assist with such engagement.) The radius of intermediate tube 96 is approximately equal to the distance of each of the indentations from a center of upper surface 50, so that the protrusions at the distal end of the tube are aligned with the indentations. Alternatively, the upper surface defines one or more protrusions, which engage indentations on the distal end of tube 96 (configuration not shown). Indentations 99 or the protrusions thus serve as driving interface 48.

Rotation of intermediate tube 96 causes corresponding rotation of spool 46, thereby winding contracting member 30 around the spool, and tightening the contracting member.

An outer tube 94, if provided, is configured to prevent rotation of spool housing 44 during rotation of spool 46. To this end, outer tube 94 (such as distal-most portion 94D thereof) is configured to engage an upper surface 160 of spool housing 44. To enable such engagement, the upper surface typically is shaped so as to define one or more indentations 162 (e.g., grooves), in which corresponding protrusions at the distal end of outer tube 94 are positioned, such as by gently rotating the tube (or all of the tubes) until such engagement occurs. (Springs may be provided to assist with such engagement.) The radius of outer tube 94 is approximately equal to the distance of each of the indentations from a center of spool housing 44, so that the protrusions at the distal end of the tube are aligned with the indentations. Alternatively, the upper surface defines one or more protrusions, which engage indentations on the distal end of tube 94 (configuration not shown).

During rotation of intermediate tube 96 for rotating spool 46, outer tube 94 is held rotationally stationary, thereby stabilizing spool housing 44 and enabling spool 46 to rotate with respect to housing 44 either in a first rotational direction or a second rotational direction that is opposite the first rotational direction. For example, when distal portion 88 is rotated in the first rotational direction, contracting member 30 is wound around spool 46, and when distal portion 88 is rotated in the second rotational direction, contracting member 30 is unwound from around spool 46. As described hereinabove, tool 80 is slid within sheath 89.

Inner tube 98 is configured to decouple longitudinal member 86 from spool 46 after contracting member 30 has been sufficiently wound around the spool, as described above. To this end, a distal portion of the inner tube (such as distal-most portion 98D thereof) is shaped so as to engage a distal portion of longitudinal member 86, which is typically shaped so as to couple with the distal portion of the inner tube.

Rotation of inner tube 98, while intermediate tube 96 is prevented from rotating and thus prevents rotation of spool 46, causes corresponding rotation of longitudinal member 86, and unscrews the longitudinal member from spool 46. Longitudinal member 86 and spool 46 are typically configured such that this unscrewing rotation is in the opposite direction of the rotation of the spool that tightens the contracting member. For example, clockwise rotation of the spool (looking down on the spool) may wind the contracting member around the spool, while counterclockwise rotation of longitudinal member 86 may unscrew the longitudinal member from the spool. To enable the engagement of inner tube 98 with the distal portion of the longitudinal member, the distal portion may include a flat portion.

As shown, spool 46 is shaped to define a driving interface 48. For some applications, driving interface 48 is female. For example, the interface may be shaped to define a channel which extends through the cylindrical portion of spool 46 from an opening provided by an upper surface 178 (shown below in FIG. 6A, for example) of spool 46 to an opening provided by a lower surface 180 of spool 46. Alternatively, driving interface 48 is shaped so as to define an indentation (e.g., a groove) that does not extend entirely through the cylindrical portion of the spool. Further alternatively, driving interface 48 is male, and defines a protrusion, e.g., a hexagonal head or a head having another shape.

For some applications, a distal portion of a rotation tool 80, engages spool 46 via driving interface 48 and rotates spool 46 in response to a rotational force applied to the rotation tool. The rotational force applied to the rotation tool rotates spool 46 via the portion of the rotation tool that engages driving interface 48 of spool 46.

Spool 46 typically comprises a locking mechanism that prevents rotation of the spool after contracting member 30 has been tightened. For example, locking techniques may be used that are described with reference to FIG. 4 of above-mentioned U.S. application Ser. No. 12/341,960 to Cabiri (published as US 2010/0161047), and/or with reference to FIGS. 6B, 7, and 8 of U.S. patent application Ser. No. 12/689,635 to Zipory et al. (published as US 2010/0280604), entitled, "Over-wire rotation tool," filed Jan. 19, 2010, which are incorporated herein by reference.

Alternatively, for some applications, contracting mechanism 40 is configured to tighten contracting member 30, crimp the contracting member to hold the contracting member taut, and subsequently cut the excess length of the contracting member.

Distal portion 88 of rotation tool 80 has a head that is male (e.g., comprising a threaded screwdriver head, as shown) having, such as a slot-head, an Allen-head, a Phillips-head, a Robertson-head, or a hex-head. For some applications, distal portion 88 of rotation tool 80 has a head that is female (e.g., comprising a wrench head, having, for example, a square or hex opening), as appropriate for driving interface 48 provided. Typically, the rotation tool comprises a shaft (e.g., tube 94), at least a portion of which is flexible. For some applications, the rotation tool is used that is described in above-referenced U.S. patent application Ser. No. 12/341,960 (published as US 2010/0161047), with reference to FIG. 4 thereof.

Figure 6B:
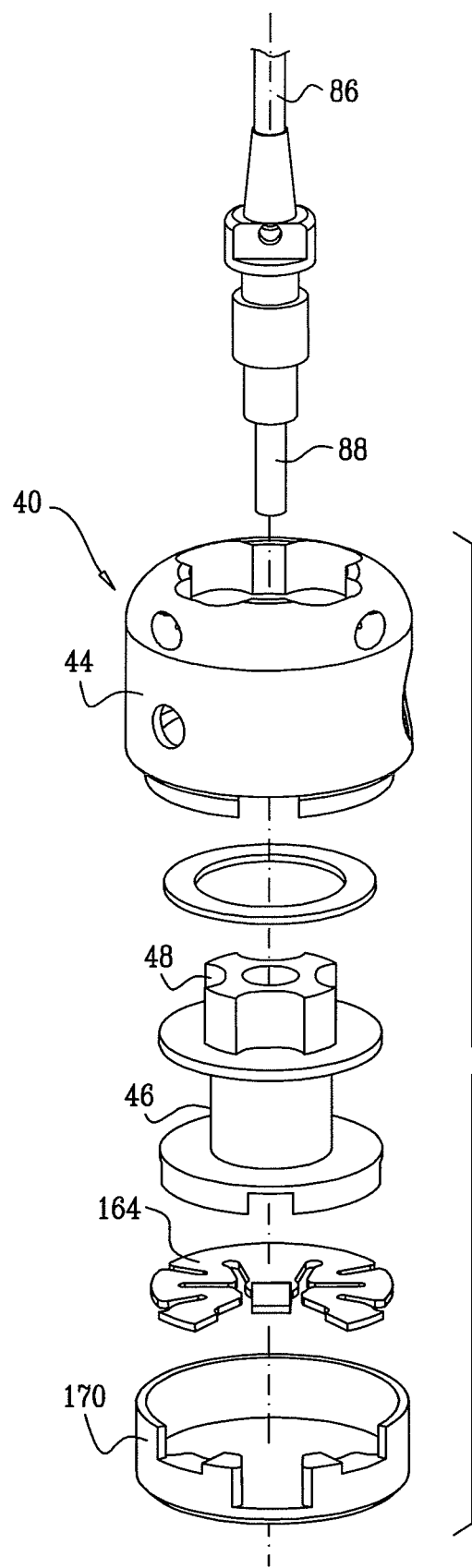

FIG. 6 shows a relationship among individual components of contracting mechanism 40, in accordance with some applications of the present invention. Contracting mechanism 40 is shown as comprising spool housing 44 which defines an upper surface 160 and a recessed portion 176. Spool 46 is configured to be disposed within housing 44 and defines an upper surface 178, a lower surface 180 and a cylindrical body portion disposed vertically between surfaces 178 and 180. For some applications, a contracting mechanism as shown in FIG. 6B is used, mutatis mutandis. Although some applications of the present invention are described with reference to a contracting mechanism as shown in FIG. 6A, the scope of the present invention includes using the contracting mechanism shown in FIG. 6B in combination with other components of the apparatus described herein.

Reference is now made to FIGS. 5 and 6A. Lower surface 180 of spool 46 is shaped to define one or more (e.g., a plurality, as shown) recesses 182 which define structural barrier portions 188 of lower surface 180. It is to be noted that any suitable number of recesses 182 may be provided, e.g., between 1 and 10 recesses, circumferentially (as shown) or otherwise with respect to lower surface 180 of spool 46.

For some applications, as mentioned above, spool 46 comprises a locking mechanism 164 (FIG. 5). For some applications, locking mechanism 164 is coupled, e.g., welded, at least in part to a lower surface of spool housing 44. Typically, locking mechanism 164 defines a mechanical element having a planar surface that defines slits 184. The surface of locking mechanism 164 may also be curved, and not planar. Locking mechanism 164 is shaped to provide a protrusion 166 which projects out of a plane defined by the planar surface of the mechanical element. The slits define a depressible portion 168 of locking mechanism 164 that is disposed in communication with and extends toward protrusion 166. Depressible portion 168 is moveable in response to a force applied thereto by a distal element 70 that extends in a distal direction from distal portion 88 of longitudinal member 86, beyond threaded opening 92 of upper surface 50, as shown in FIG. 5.

It is to be noted that the planar, mechanical element of locking mechanism 164 is shown by way of illustration and not limitation and that any suitable mechanical element having or lacking a planar surface but shaped to define at least one protrusion may be used together with locking mechanism 164.

A cap 170 is provided that is shaped so as to define a planar surface and an annular wall having an upper surface 186 that is coupled to, e.g., welded to, a lower surface of spool housing 44. The annular wall of cap 170 is shaped so as to define a recessed portion 172 of cap 170 that is in alignment with recessed portion 176 of spool housing 44.

For some applications, spool 46 of contracting mechanism 40 is shaped to provide a hole 42 or other coupling mechanism for coupling the first end portion of contracting member 30 to the spool, and thereby to contracting mechanism 40.

Figure 7:
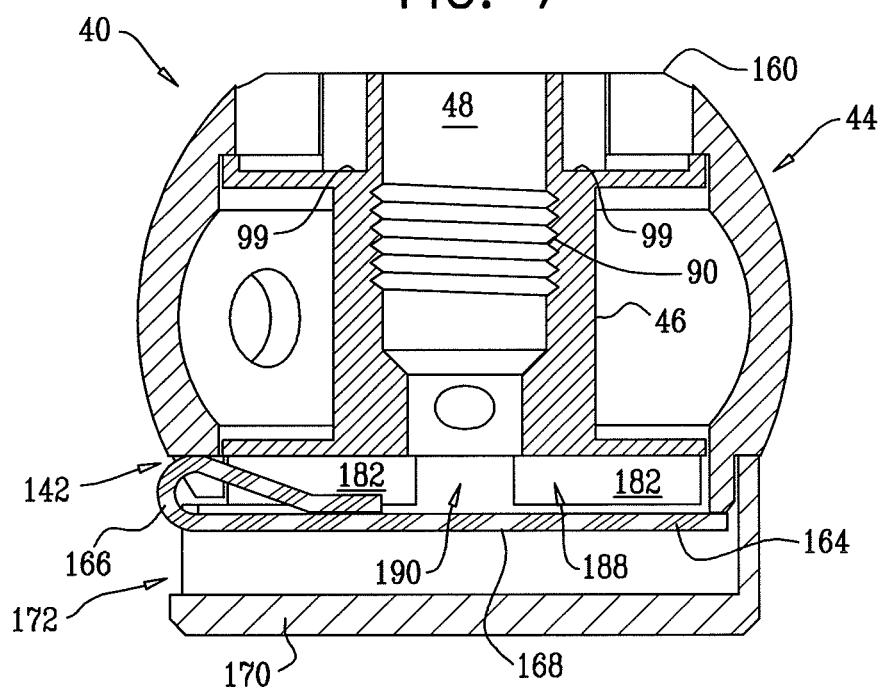
FIG. 7 is another cross-sectional illustration of the contracting mechanism of FIG. 5, in accordance with some applications of the present invention.

Reference is again made to FIG. 5, and is additionally made to FIG. 7, which is another cross-sectional illustration of contracting mechanism 40, in accordance with an application of the present invention. FIG. 5 shows contracting mechanism 40 in an unlocked state, while FIG. 7 shows the contracting mechanism in a locked state.

In the unlocked state shown in FIG. 5, protrusion 166 of locking mechanism 164 is disposed within recessed portion 172 of cap 170. Longitudinal member 86 is shaped so as to define a distal force applicator 174 that extends distally, typically beyond screw thread 90. In the unlocked state, the force applicator extends through spool 46 and pushes against depressible portion 168 of locking mechanism 164. The depressible portion is thus pressed downward, as shown in FIG. 5, freeing protrusion 166 from within a recess 190 defined by structural barrier portions 188 of the lower portion of spool 46. Additionally, protrusion 166 is freed from within recessed portion 176 provided by spool housing 44. As a result, contracting mechanism 40 is unlocked, and spool 46 may be rotated with respect to spool housing 44.

Cap 170 functions to restrict distal pushing of depressible portion 168 beyond a desired distance so as to inhibit deformation of locking mechanism 164. For applications in which contracting mechanism 40 is implanted in heart tissue, cap 170 also provides an interface between contracting mechanism 40 and the heart tissue. This prevents interference of heart tissue on contracting mechanism 40 during the locking and unlocking thereof. Additionally, cap 170 prevents damage to heart tissue by depressible portion 168 as it is pushed downward.

In the locked state shown in FIG. 7, protrusion 166 is positioned within a recess 190 of spool 46. Typically, the locked state is the resting state of locking mechanism 162. Depressible portion 168 is disposed in a horizontal position, in response to removal of distal force applicator 174 from within spool 46. Depressible portion 168 has a tendency to assume the horizontal position, as shown, and in the absence of a downward pushing force applied to depressible portion 168 by force applicator 174, depressible portion 168 returns to its horizontal position from its pushed-down state, as shown in FIG. 7. In this horizontal position, protrusion 166 of locking mechanism 164 is removed from recessed portion 172 of cap 170 and is returned within a recess 190 of spool 46 and thereby restricts movement of spool 46 and locks contracting mechanism 40. Additionally, protrusion 166 of locking mechanism 164 returns in part within recessed portion 176 of spool housing 44. Thus, recessed portion 176 of spool housing 44 provides supplemental locking of locking mechanism 164.

It is to be noted that although contracting mechanism 40 in FIG. 7 is shown without contracting member 30 for clarity of illustration, contracting member 30 is coupled to a portion of contracting mechanism 40.

Figure 8A:
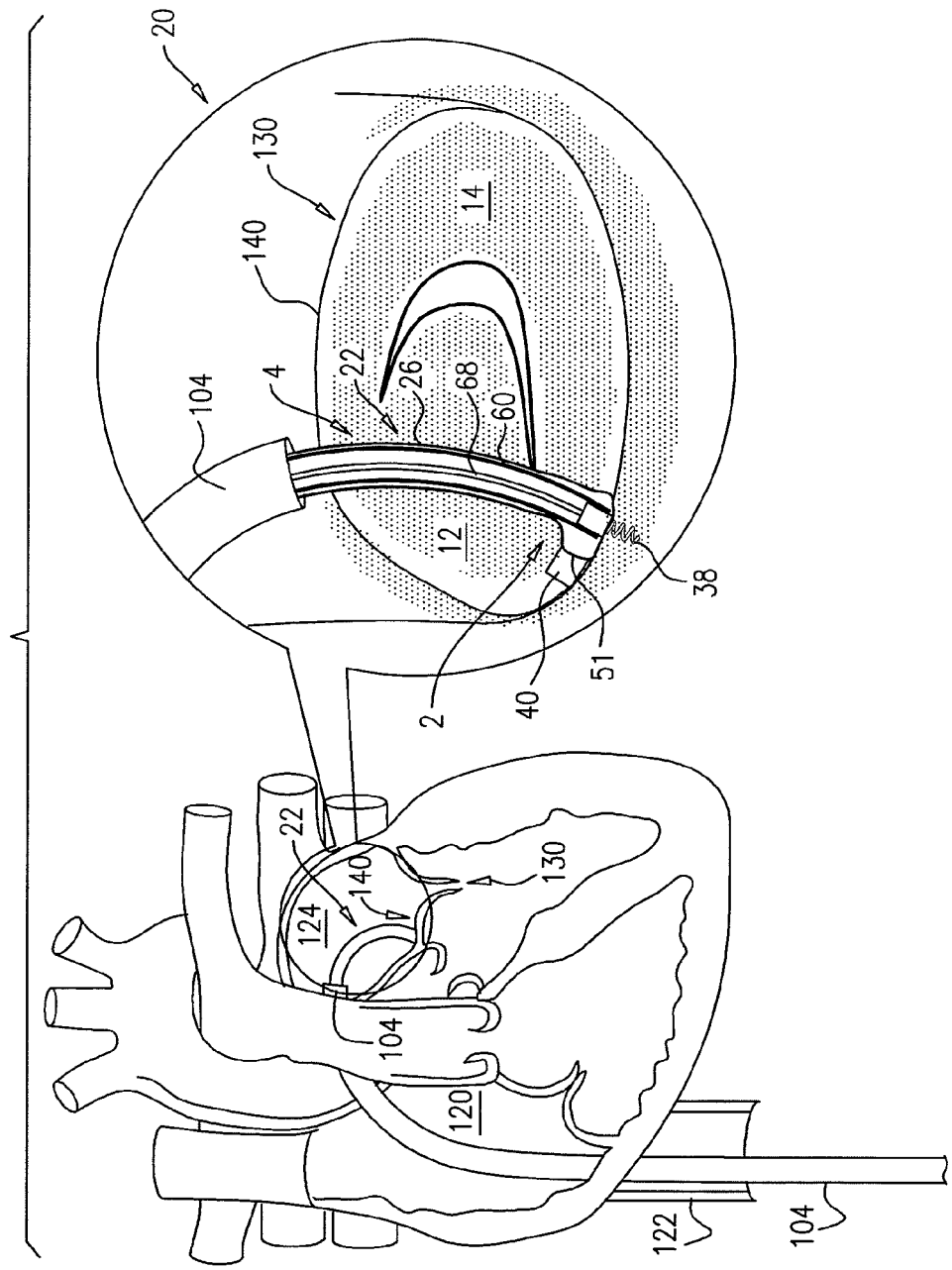
Figure 8B:
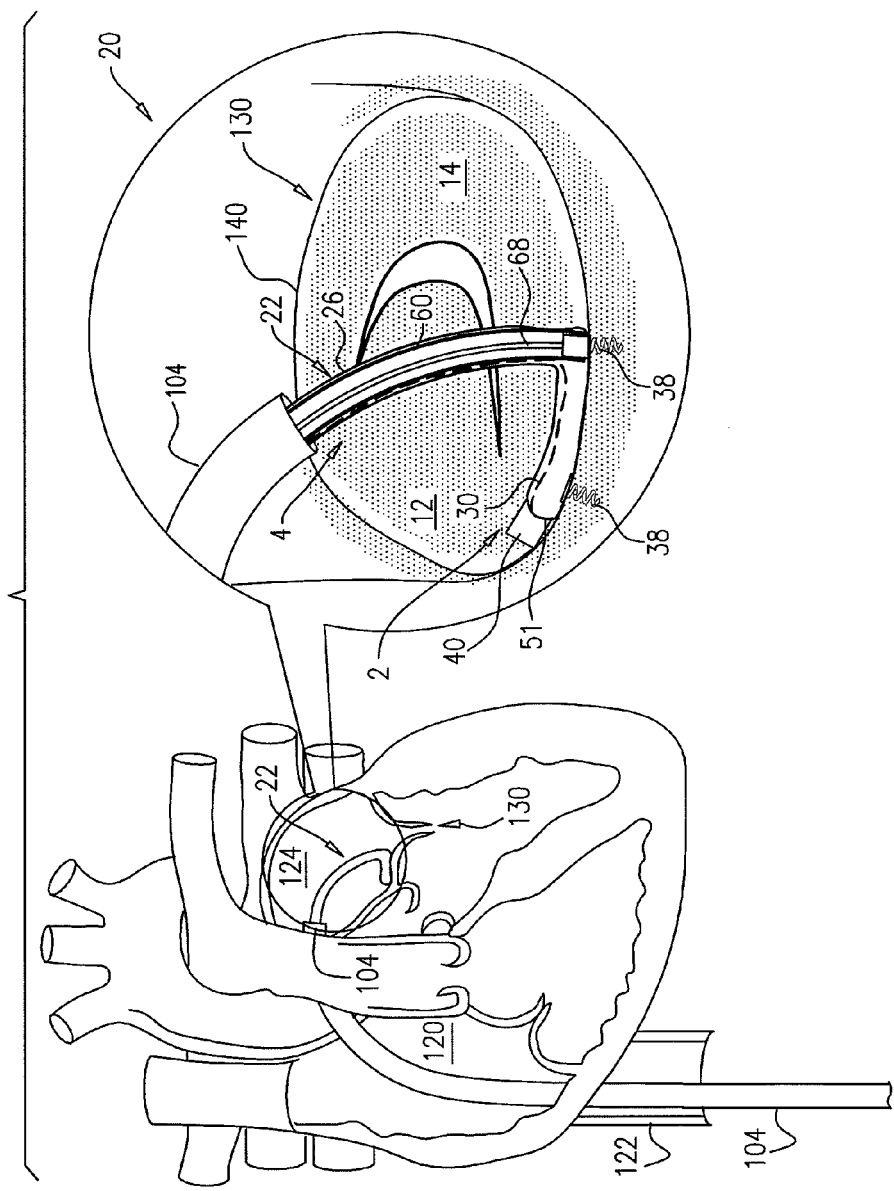

Reference is now made to FIGS. 8A-C, which are schematic illustrations of a procedure for implanting implant structure 22 to repair mitral valve 130, in accordance with an application of the present invention. The procedure is typically performed transluminally with the aid of imaging, such as fluoroscopy, transesophageal echo, and/or echocardiography.

The procedure typically begins by advancing a semi-rigid guidewire (not shown) into a right atrium 120 of the patient. The guidewire provides a guide for the subsequent advancement of an access sheath 104 therealong and into the right atrium. Once sheath 104 has entered the right atrium, the guidewire is retracted from the patient's body. Sheath 104 typically comprises a 14-20 F sheath, although the size may be selected as appropriate for a given patient. Sheath 104 is advanced through vasculature into the right atrium using a suitable point of origin typically determined for a given patient. For example:

sheath 104 may be introduced into the femoral vein of the patient, through an inferior vena cava 122, into right atrium 120, and into a left atrium 124 transseptally, typically through the fossa ovalis;

sheath 104 may be introduced into the basilic vein, through the subclavian vein to the superior vena cava, into right atrium 120, and into left atrium 124 transseptally, typically through the fossa ovalis;

sheath 104 may be introduced into the external jugular vein, through the subclavian vein to the superior vena cava, into right atrium 120, and into left atrium 124 transseptally, typically through the fossa ovalis; or sheath 104 may be introduced into left atrium 124 transatrially, e.g., via the interatrial groove, or via the upper surface of the left atrium.

For some applications of the present invention, sheath 104 is advanced through an inferior vena cava 122 of the patient (as shown) and into right atrium 120 using a suitable point of origin typically determined for a given patient.

Sheath 104 is advanced distally until the sheath reaches the interatrial septum.

A resilient needle and a dilator (not shown) are advanced through sheath 104 and into the heart. In order to advance sheath 104 transseptally into left atrium 124, the dilator is advanced to the septum, and the needle is pushed from within the dilator and is allowed to puncture the septum to create an opening that facilitates passage of the dilator and subsequently sheath 104 therethrough and into left atrium 124. The dilator is passed through the hole in the septum created by the needle. Typically, the dilator is shaped to define a hollow shaft for passage along the needle, and the hollow shaft is shaped to define a tapered distal end. This tapered distal end is first advanced through the hole created by the needle. The hole is enlarged when the gradually increasing diameter of the distal end of the dilator is pushed through the hole in the septum.

The advancement of sheath 104 through the septum and into the left atrium is followed by the extraction of the dilator and the needle from within sheath 104.

Implant structure 22 (with anchor deployment manipulator 60 therein) is advanced through sheath 104 into left atrium 124.

As shown in FIG. 8A, end 51 of sleeve 26 is positioned in a vicinity of a left fibrous trigone 2 of an annulus 140 of mitral valve 130. (It is noted that for clarity of illustration, end 51 of sleeve 26 is shown schematically in the cross-sectional view of the heart, although left trigone 2 is in reality not located in the shown cross-sectional plane, but rather out of the page closer to the viewer.) Alternatively, the tip is positioned in a vicinity of a right fibrous trigone 4 of the mitral valve (configuration not shown). Further alternatively, end 51 of sleeve 26 is not positioned in the vicinity of either of the trigones, but is instead positioned elsewhere in a vicinity of the mitral valve, such as in a vicinity of the anterior or posterior commissure. For some applications, outer tube 62 of anchor deployment manipulator 60 is steerable, as is known in the catheter art, while for other applications, a separate steerable tube is provided. In either case, the steering functionality typically allows the area near the distal end of the deployment manipulator to be positioned with six degrees of freedom. Once positioned at the desired site near the selected trigone, deployment manipulator 60 deploys a first anchor 38 through the wall of sleeve 26 into cardiac tissue near the trigone.

As shown in FIG. 8B, deployment manipulator 60 is repositioned along annulus 140 to another site selected for deployment of a second anchor 38. Typically, the first anchor is deployed most distally in the sleeve (generally at or within a few millimeters of the distal tip of the sleeve), and each subsequent anchor is deployed more proximally, such that the sleeve is gradually pulled off (i.e., withdrawn from) the deployment manipulator in a distal direction during the anchoring procedure. The already-deployed first anchor 38 holds the anchored end of sleeve 26 in place, so that the sleeve is drawn from the site of the first anchor towards the site of the second anchor. Typically, as sleeve 26 is pulled off (i.e., withdrawn from) the deployment manipulator, the deployment manipulator is moved generally laterally along the cardiac tissue, as shown in FIG. 8B. Deployment manipulator 60 deploys the second anchor through the wall of sleeve 26 into cardiac tissue at the second site. Depending on the tension applied between the first and second anchor sites, the portion of sleeve 26 therebetween may remain tubular in shape, or may become flattened, which may help reduce any interference of implant structure 22 with blood flow.

For some applications, in order to provide the second and subsequent anchors, anchor driver 68 is withdrawn from the patient's body via sheath 104 (typically while leaving outer tube 62 of the deployment manipulator in place in the sleeve), provided with an additional anchor, and then reintroduced into the patient's body and into the outer tube. Alternatively, the entire deployment manipulator, including the anchor driver, is removed from the body and subsequently reintroduced upon being provided with another anchor. Further alternatively, deployment manipulator 60 is configured to simultaneously hold a plurality of anchors, and to deploy them one at a time at the selected sites.

As shown in FIG. 8C, deployment manipulator 60 is repositioned along the annulus to additional sites, at which respective anchors are deployed, until the last anchor is deployed in a vicinity of right fibrous trigone 4 (or left fibrous trigone 2 if the anchoring began at the right trigone). Alternatively, the last anchor is not deployed in the vicinity of a trigone, but is instead deployed elsewhere in a vicinity of the mitral valve, such as in a vicinity of the anterior or posterior commissure.

As described hereinabove with reference to FIGS. 6 and 7, rotation tool 80 used to rotate spool 46 of contracting mechanism 40, in order to tighten implant structure 22. (For clarity of illustration, contracting member 30 of implant structure 22, although provided, is not shown in FIGS. 8A-C.)

For some applications, sleeve 26 is filled with a material (e.g., polyester, polytetrafluoroethylene (PTFE), polyethylene terephthalate (PET), or expanded polytetrafluoroethylene (ePTFE)) after being implanted. The material is packed within at least a portion, e.g., 50%, 75%, or 100%, of the lumen of sleeve 26. The filler material functions to prevent (1) formation within the lumen of sleeve 26 of clots or (2) introduction of foreign material into the lumen which could obstruct the sliding movement of contracting member 30.

As described hereinabove with reference to FIGS. 3D-E, end 49 of sleeve 26 is closed upon completion of the implantation procedure. Alternatively, the proximal end of the sleeve may have a natural tendency to close when not held open by deployment manipulator 60.

Reference is made to FIG. 9, which is a schematic illustration of the deployment of one of anchors 38 into cardiac tissue, in accordance with an application of the present invention. For these applications, one or more (such as all) of anchors 38 are deployed from left atrium 124, through tissue of the atrial wall, and into tissue of an upper region of the ventricular wall 150 near the atrium. Because the tissue of the upper region of ventricular wall is thicker than that of the atrial wall, deploying the anchors into the upper region of the ventricular wall generally provides more secure anchoring. In addition, because the anchors are not deployed laterally through the atrial wall, the risk of perforating the atrial wall is reduced.

FIGS. 10A-E are schematic illustrations of a system 220 comprising an implant structure 222 comprising sleeve 26 that defines a lumen for insertion therethrough of a coiled element 240, in accordance with some applications of the present invention. Implant structure 222 is generally similar to implant structure 22, as described hereinabove with reference to FIGS. 1, 2, 3A-F, 4-7, 8A-C, and 9, with the exception that (a) coiled element 240 (which comprises a contraction-restricting element 200) is advanced within the lumen of sleeve 26 during the implantation procedure, as described hereinbelow, or is prepositioned in the sleeve prior to commencement of the implantation procedure, and (b) implant structure 222 typically does not comprise crimping element(s) 32 or 34.

Implant structure 222 is implanted along the annulus of the native mitral valve in a manner as described hereinabove with reference to FIGS. 2, 3A-C, 8A-C, and 9, with regard to the implantation of implant structure 22 along the annulus of the mitral valve. In this configuration, implant structure 222 is typically configured to not contract the posterior portion of the annulus along the middle scallop (P2) of the posterior leaflet, and to contract portions of the annulus along (a) a lateral scallop (P1) of the posterior leaflet and extending to left fibrous trigone 4, and (b) the medial scallop (P3) of the posterior leaflet and extending to right fibrous trigone 2.

Sleeve 26 of implant structure 222 is shaped so as to define an opening at proximal end 49 thereof. A contraction-restricting-element advancement tube 230 is advanced toward implant structure 222 through a lumen of a delivery tube 232. It is to be noted that outer tube 62 (shown in FIGS. 2 and 3A-C) of manipulator 60 may be advanced within delivery tube 232 during the anchoring of implant structure 222 to the annulus. For some applications, advancement tube 230 may be slidable within sheath 104 (shown in FIGS. 8A-C and 9).

Figure 10A:
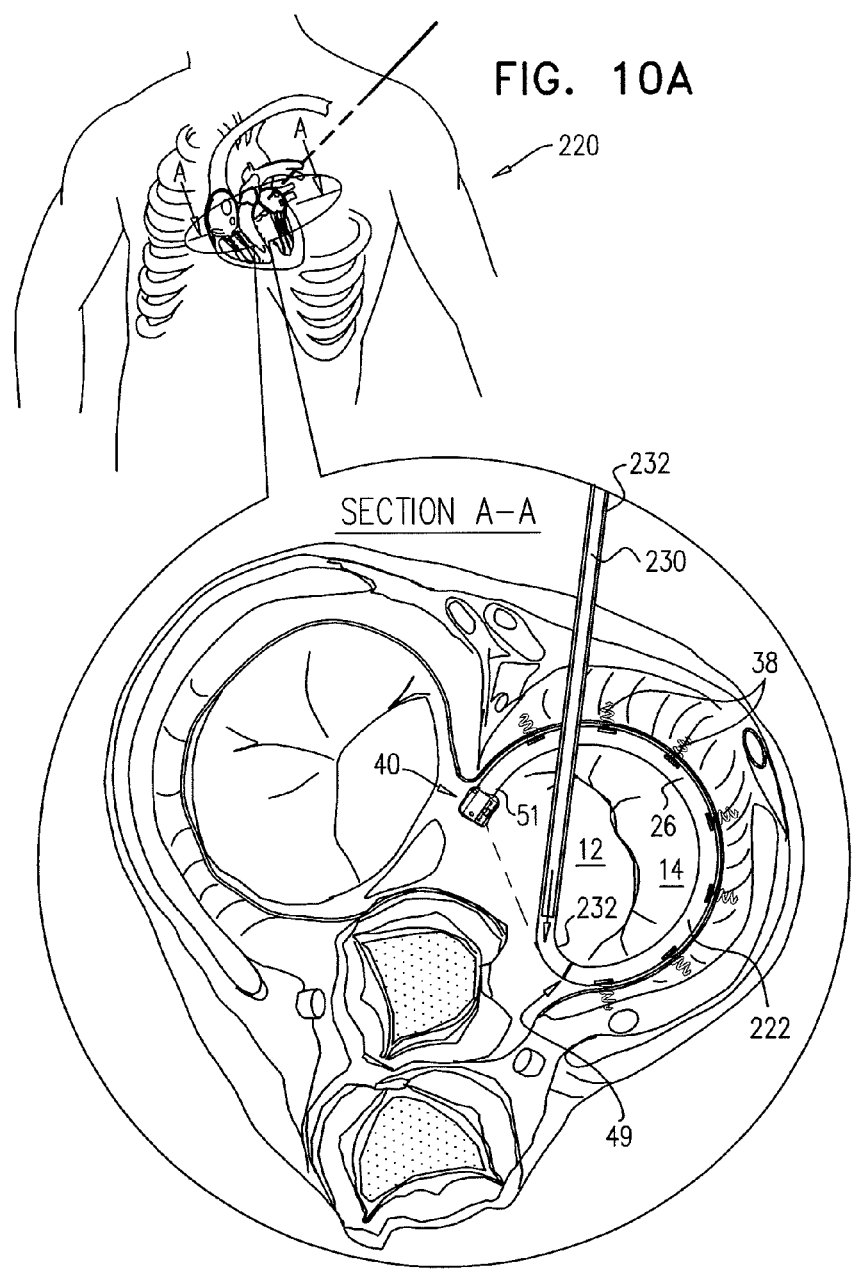
Figure 10B:
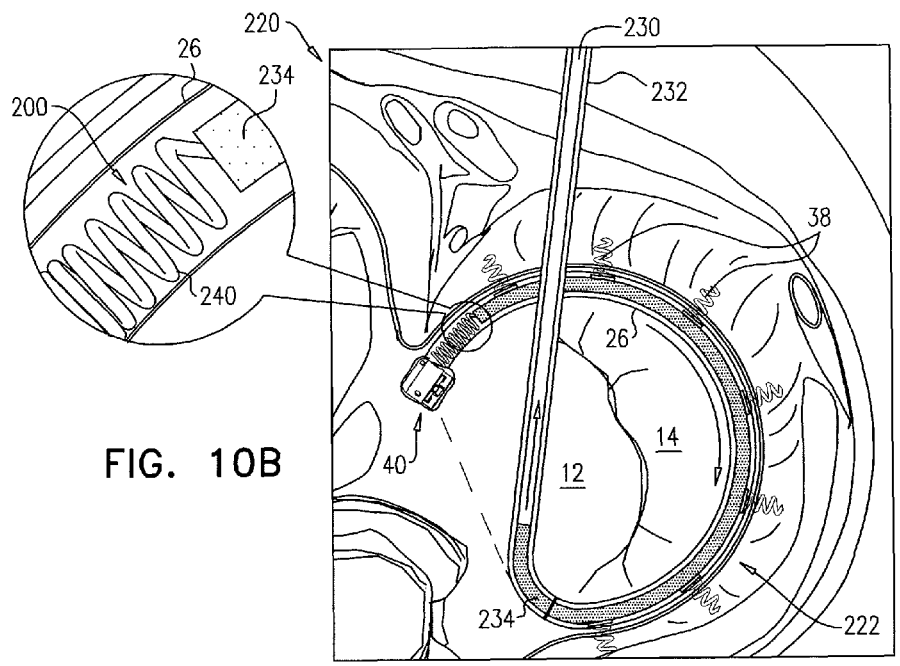

Advancement tube 230 is advanced within the lumen of sleeve 26 until distal end 51 thereof. For some applications, delivery tube 232 is also advanced within the lumen of sleeve 26 until distal end 51 thereof (not shown for clarity of illustration). As shown in FIG. 10B, advancement tube 230 houses an overtube 234 which, in turn, houses coiled element 240. Coiled element 240 comprises a flexible material, e.g., nitinol, which is biased to assume the coiled shape shown in FIG. 10C. For some applications in which the coiled element comprises such a flexible material, coiled element 240 is disposed within overtube 234 in a state in which coiled element 240 is generally straightened from its coiled state, i.e., at least partially uncoiled. In order to deploy element 240 within the lumen of sleeve 26, overtube 234 is retracted in the direction indicated by the arrow in FIG. 10B. For some applications, a pusher (not shown) disposed within overtube 234 proximally to element 240 pushes on element 240 as overtube 234 is retracted. During the deployment of coiled element 240, successive portions of element 240 are exposed from within overtube 234 and assume the pre-determined coiled configuration, as shown.

Figure 10C:
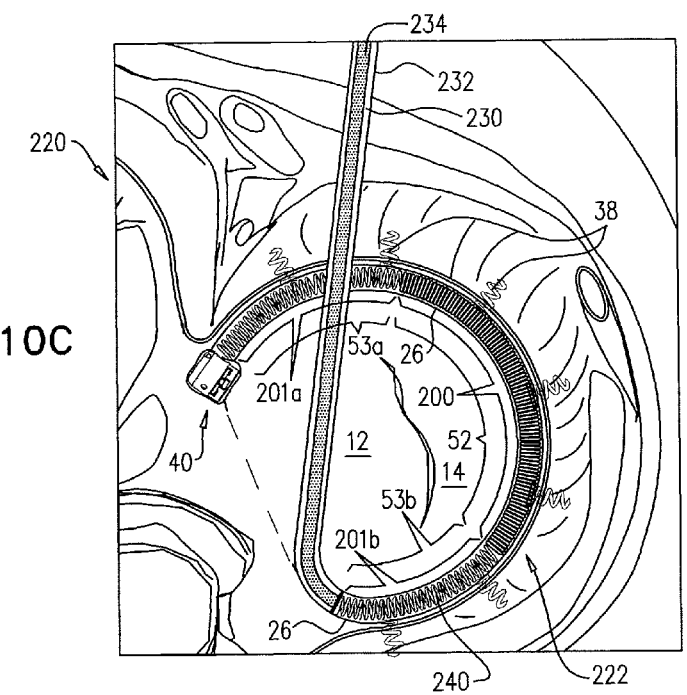

As shown in FIG. 10C, coiled element 240 is advanced within the lumen of sleeve 26 and comprises contraction-restricting element 200 and contractible portions 201a and 201b. In its deployed configuration, i.e., its coiled configuration, element 240 is typically shaped so as to define a diameter of between 2 and 6 mm, e.g., 3 mm. As shown in FIG. 10D, following the advancement of coiled element 240 within the lumen of sleeve 26, overtube 234, advancement tube 230, and delivery tube 232 are removed from within the body of the patient, and the opening at proximal end 40 of implant structure 222 is typically closed, such as by closure mechanism 290. For some applications, closure mechanism 290 comprises closure mechanism 290, as described hereinabove with reference to FIGS. 1 and 3D-E. For some applications, closure mechanism 290 comprises closure mechanism 290, as will be described hereinbelow with reference to FIGS. 14A-B.

As shown in FIGS. 10C-D, contraction-restricting element 200 is a coiled portion of element 240 that is non-compressible, and contractible portions 201a and 201b (that are coupled to, or flank, contraction-restricting element 200) are respective portions of element 240 that are compressible. Contraction-restricting element 200 defines a pitch that is smaller than that of portions 201a and 201b (as shown in the blow-ups in FIG. 10D). Thus, if coiled element 240 were to be positioned along a longitudinal axis, contraction-restricting element 200 would restrict contraction of element 240 (and thereby implant structure 222) along the longitudinal axis, while contractible portions 201a and 201b would allow contraction of element 240 (and thereby implant structure 222) along the longitudinal axis. When coiled element 240 is positioned within the lumen of sleeve 26, as shown in FIGS. 10C-D, (1) contraction-restricting element 200 defines contraction-restricted portion 52 of structure 222 that is disposed along the portion of the annulus at posterior leaflet 14, and (2) contractible portions 201a and 201b define respective contraction-facilitated portions 53a and 53b of structure 222 that are contractible and expandable in response to respective tightening or loosening of contracting member 30 (not shown for clarity of illustration) responsively to the actuation of contracting mechanism 40. For some applications, contraction-restricting element 200 has a length of more than 3 mm and/or less than 120 mm (e.g., a length of 3 mm-120 mm), and defines contraction-restricted portion 52, portion 52 having a length of more than 3 mm and/or less than 120 mm (e.g., a length of 3 mm-120 mm). During the ongoing contraction of structure 222 responsively to the actuation of contracting mechanism 40, contractible portions 201a and 201b facilitate longitudinal contraction of portions 53a and 53b, respectively, while contraction-restricting element 200 restricts longitudinal contraction of portion 52, but facilitates radial movement of portion 52 toward the center of the valve (i.e., in the direction as indicated by the arrows). This radial movement of portion 52 brings leaflet 14 toward leaflet 12.

It is to be noted that one contraction-restricting element 200 and two contractible portions 201a and 201b are shown in FIGS. 10A-D by way of illustration and not limitation, and that coiled element 240 may comprise any suitable number of elements 200 or portions 201. For example, in FIG. 10E coiled element 240 is shown, the coiled element defining two contraction-restricting elements 200a and 200b, and two contractible portions 201a and 201b. When coiled element 240 is positioned within the lumen of sleeve 26, as shown in FIG. 10E, (1) contraction-restricting element 200a defines contraction-restricted portion 52a of structure 222 that is disposed along the portion of the annulus at posterior leaflet 14, (2) contraction-restricting element 200b defines contraction-restricted portion 52b of structure 22 that is disposed in a vicinity of trigone 4, and (3) contractible portions 201a and 201b define respective contraction-facilitated portions 53a and 53b of structure 222 that are contractible and expandable in response to respective tightening or loosening of contracting member 30 (not shown for clarity of illustration) responsively to the actuation of contracting mechanism 40. Typically, contraction-restricted portion 52a comprises more than 10% (e.g., more than 20%), and/or less than 60% (e.g., less than 30%) of the resting length of coiled element 240. For some applications, each of contraction-facilitated portions 53a and 53b comprises less than 50% (e.g., less than 20%, or less than 10%) of the resting length of coiled element 240. For some applications, the total length of the contraction-facilitated portions of coiled element 240 comprises less than 50%, e.g., less than 30%, of the resting length of the coiled element.

In the configuration shown in FIG. 10E, coiled element 240 defines two contraction-restricting elements 200a and 200b, one of which is disposed along the portion of the annulus at posterior leaflet 14, and one of which is disposed in a vicinity of one of the trigones. However, the scope of the present invention includes configurations in which the coiled element defines three contraction-restricting elements 200, one of which is disposed along the portion of the annulus at posterior leaflet 14, and two of which are disposed in vicinities of respective trigones of the subject. For some applications, coiled element 240 defines two contraction-restricting elements 200, which are disposed in vicinities of respective trigones of the subject, e.g., as described with reference to FIG. 12.

For some applications, the implantable structures described herein are configured such that the contraction-restricted portions and the contraction-facilitated portions of the implantable structures are disposed adjacent to respective portions of the mitral annulus, so as to facilitate reshaping of the mitral annulus in a desired manner. The lengths of the contraction-restricted portions and the contraction-facilitated portions typically correspond to the corresponding portions of the mitral annulus. Typically, upon placement of the implantable structures described herein at the mitral annulus, contraction-restricted portions 52 and contraction-facilitated portions 53 are asymmetrically disposed with respect to the mitral annulus. Further typically, lengths of the contraction-restricted portions and the contraction-facilitated portions are not equal to one another. Alternatively, lengths of the contraction-restricted portions and the contraction-facilitated portions are equal to one another.

Reference is again made to FIGS. 10A-E. It is to be noted that although system 220 is advanced and implanted within the heart of the patient using a minimally-invasive procedure, any suitable procedure may be used to advance and implant system 220, e.g., a transcatheter procedure or a surgical procedure, such as an open-heart surgical procedure.

Figure 11B:
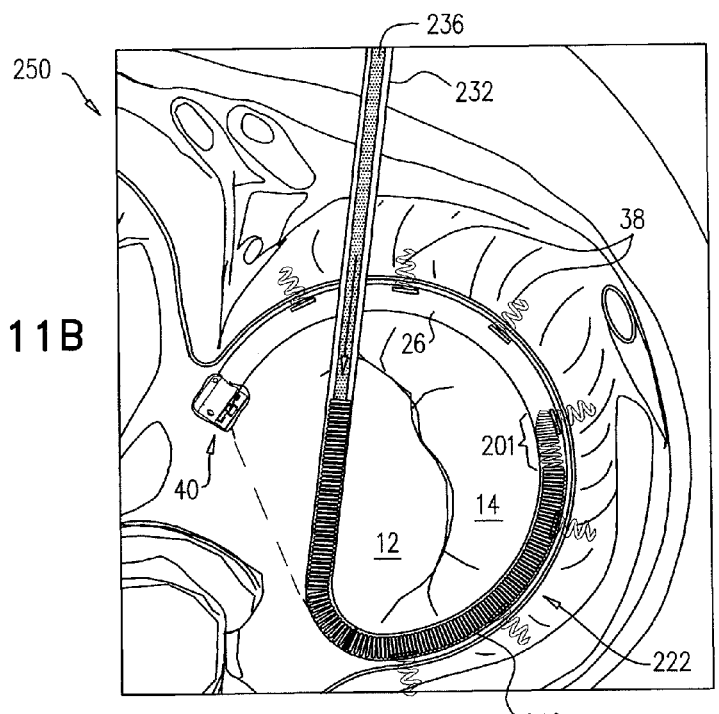
Figure 11C:
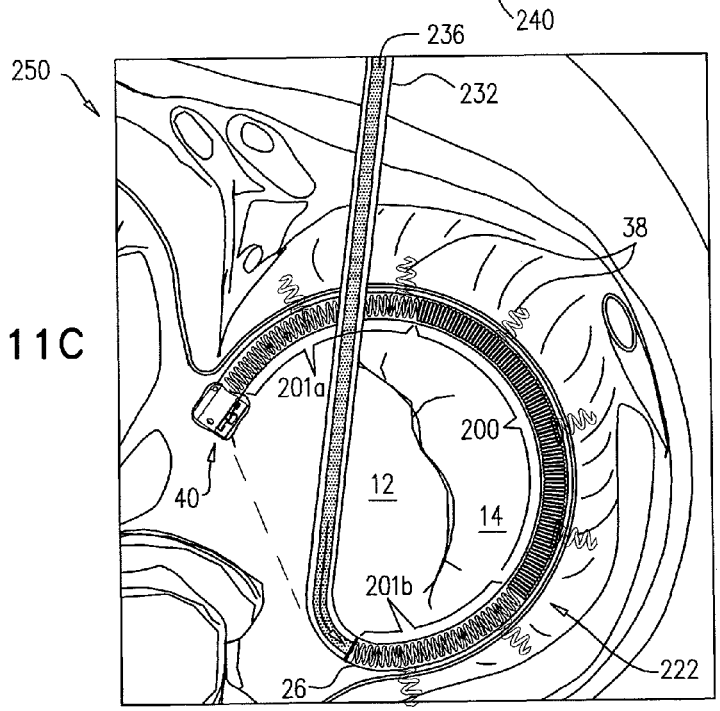
Figure 11D:
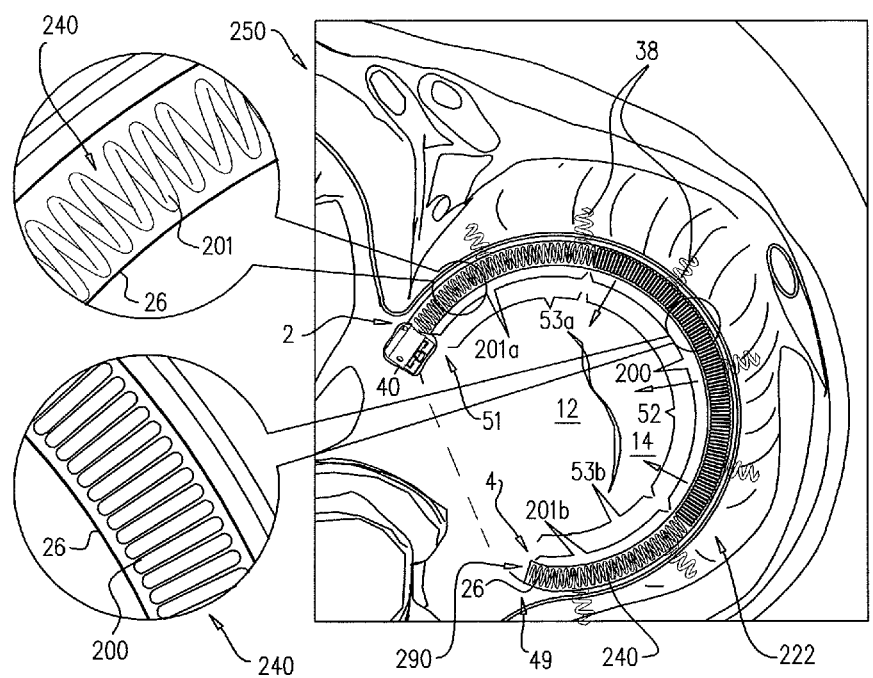

Reference is now made to FIGS. 11A-D, which are schematic illustrations of a system 250 that is similar to system 220 described hereinabove with reference to FIGS. 10A-E, with the exception that coiled element 240 is not advanced within overtube 234, in accordance with some applications of the present invention. Coiled element 240 is instead advanced directly within the lumen of delivery tube 232 and into the lumen of sleeve 26 in its coiled state, as shown in FIGS. 11A-C. Typically, a pushing tube 236 slides within delivery tube 232 proximally to coiled element 240 in order to push coiled element 240 from within the lumen of delivery tube 232 into sleeve 26. For some applications, delivery tube 232 is advanced within the lumen of sleeve 26 until distal end 51 thereof, and coiled element 240 is positioned within the lumen of sleeve 26 when tube 232 is retracted and pushing tube 236 pushes on coiled element 240.

Figure 12:
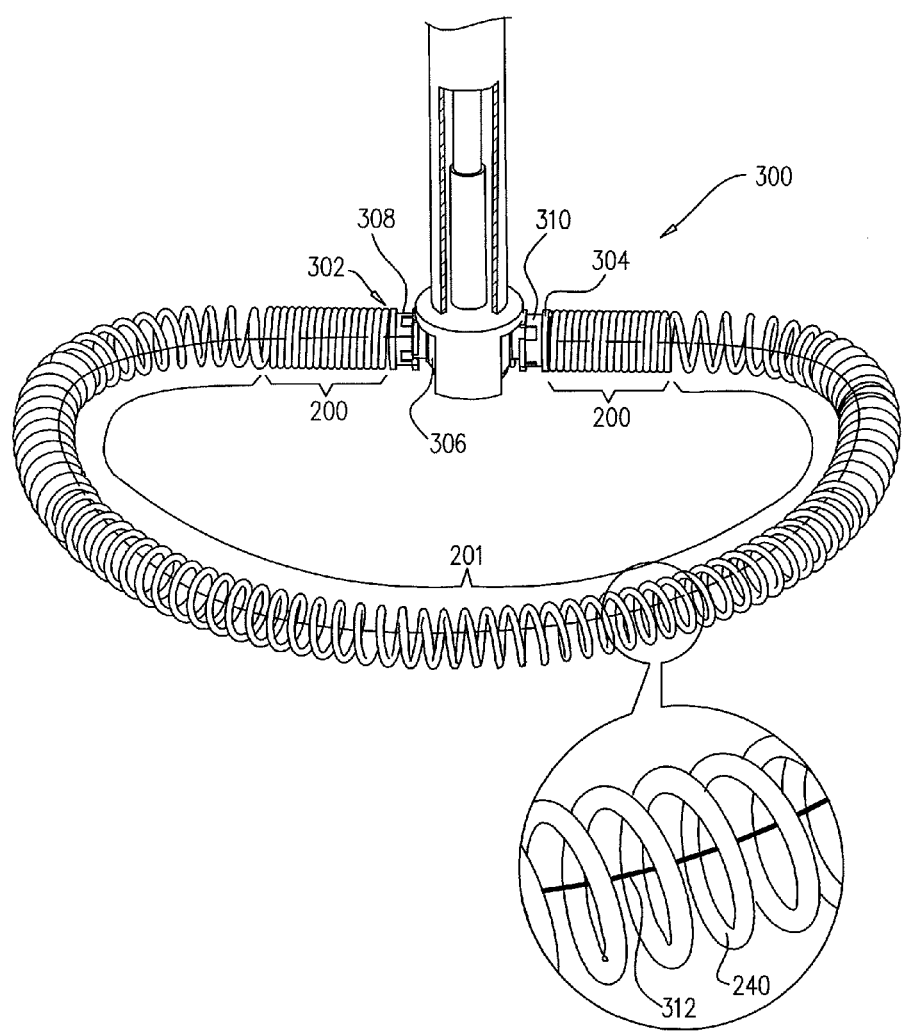
FIG. 12 is a schematic illustration of an implant structure configured to treat the mitral valve coupled to a contraction-restricting element, in accordance with some applications of the present invention.

Reference is now made to FIG. 12, which is a schematic illustration of coiled element 240, in accordance with some applications of the present invention. For some applications, techniques described herein are practiced in combination with techniques described in U.S. patent application Ser. No. 12/341,960 to Cabiri (published as US 2010/0161047), which is incorporated herein by reference. FIG. 12 is generally similar to FIG. 5 of the aforementioned Cabiri application. FIG. 12 shows a system 120 for repairing a dilated annulus of a subject comprising an annuloplasty structure 300 that defines an annuloplasty ring, in accordance with some applications of the present invention. Annuloplasty structure 300 comprises first and second ends 302 and 304, respectively, which are coupled to (e.g., welded to) a housing 306 that houses contracting mechanism 40 (which is generally as described hereinabove). Housing 306 is shaped to provide first and second coupling members 308 and 310 which are coupled to first and second ends 302 and 304, of structure 300, respectively.

For some applications, structure 300 comprises a linear, elongate structure in a resting configuration thereof. Prior to implantation, first and second ends 302 and 304 of structure 300 are welded or otherwise attached to coupling members 308 and 310, respectively, thereby facilitating the formation of structure 300 into a substantially ring-shaped structure. As described in U.S. patent application Ser. No. 12/341,960 to Cabin (published as US 2010/0161047), structure 300 typically comprises a body portion (e.g., coiled element 240) defining a lumen for housing flexible member 312. A first end of flexible member 312 is coupled to contracting mechanism 40, while a second end of flexible member 312 is coupled to second end 304 of structure 300.

As shown, structure 300 defines a substantially ring-shaped configuration, e.g., a "D"-shaped configuration, as shown, which conforms to the shape of the annulus of a mitral valve of the subject. Prior to contracting of structure 300, the coiled element 240 is relaxed and structure 300 defines a first perimeter thereof. Coiled element provides contraction-restricting elements 200 which comprise a material in a configuration in which those portions are flexible and less longitudinally compressible, e.g., not longitudinally compressible, with respect to contractible portion 201 of coiled element 240, for example, as described hereinabove. Contraction-restricting elements 200 are configured to be disposed in the vicinity of the trigones of the mitral valve of the heart, e.g., along the fibrous portion of the annulus that is between the trigones when structure 300 is anchored, sutured, fastened or otherwise coupled to the annulus of the mitral valve. Contraction-restricting elements 200 impart rigidity to structure 300 in the portion thereof that is disposed between the fibrous trigones such that structure 300 better mimics the conformation and functionality of the mitral valve.

Typically, both contraction-restricting elements 200 have a combined length of 10-50 mm.

Structure 300 defines contractible portion 201 and contraction-restricting elements 200. Typically, a radius of curvature at a center of the contractible portion of coiled element 240 is smaller than a radius of curvature at a center of contraction-restricting elements 200, when no external force is applied to the annuloplasty structure.

It is to be noted that contractible portion 201 and contraction-restricting elements 200 of structure 300 comprise a coiled element by way of illustration and not limitation. For example, contractible portion 201 and contraction-restricting elements 200 may comprise stent-like struts, or a braided mesh. In either configuration, contraction-restricting elements 200 are chronically longitudinally compressed in a resting state of structure 300.

For some applications coiled element 240 is used in combination with implant structures 222 and 250 (described with reference to FIGS. 10A-11D), the coiled element defining two contraction-restricting elements 200, which are disposed in vicinities of respective trigones of the subject, e.g., as described with reference to FIG. 12.

Figure 13:
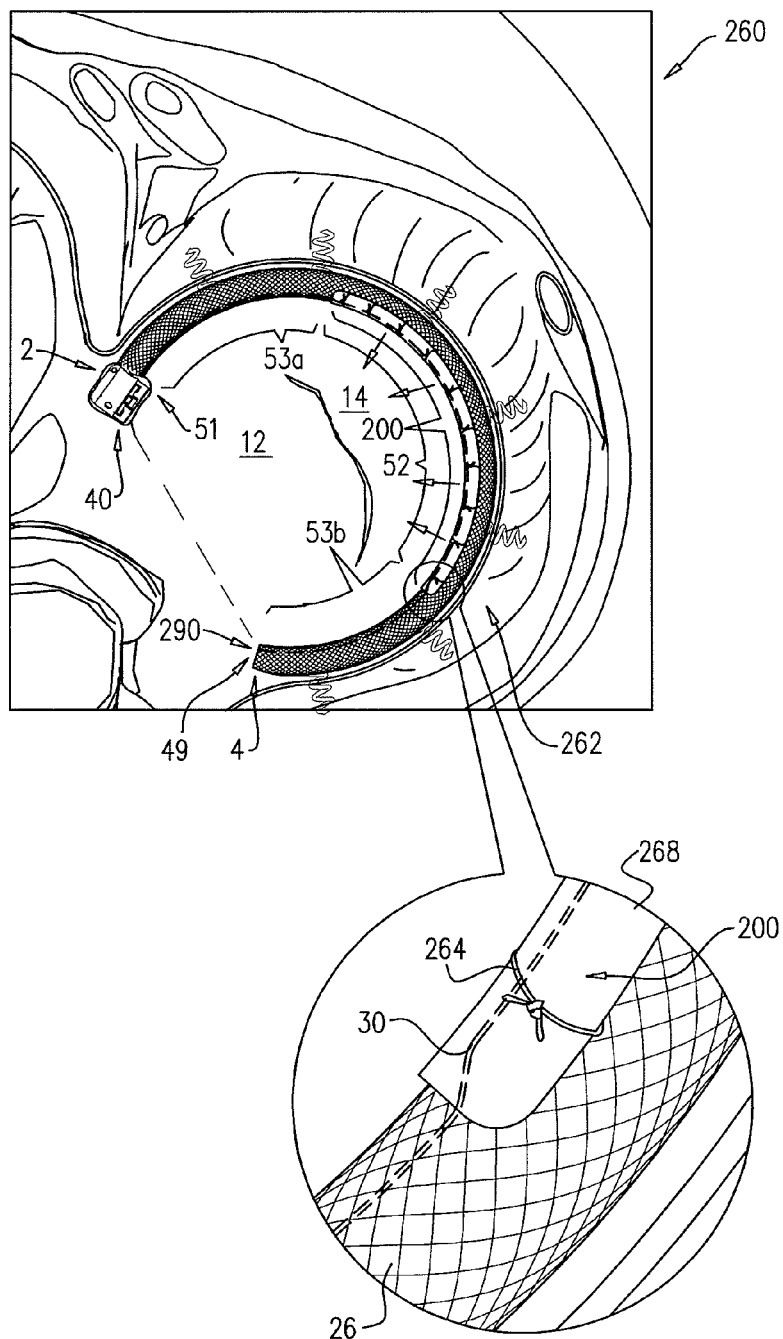
FIG. 13 is a schematic illustration of an implant structure, in accordance with some applications of the present invention.

FIG. 13 is a schematic illustration of a system 260 comprising an implant structure 262 and contraction-restricting element 200 comprising a contraction-restricting segment 268 that is coupled to an outer surface of sleeve 26, in accordance with some applications of the present invention. For some applications, segment 268 comprises a coiled element, as described hereinabove. For other applications, segment 268 comprises a tubular element comprising a material, e.g., a semi-rigid material (such as nitinol, polyethylene, and/or silicone, e.g., high-rigidity silicone), which restricts compression along a longitudinal axis of segment 268.

Typically, segment 268 is coupled to sleeve 26 by being sutured thereto via sutures 264, by way of illustration and not limitation, typically before implant 262 is advanced within the body of the patient. Segment 268 may be coupled to sleeve 26 using any suitable coupling technique. Segment 268 is typically coupled to sleeve 26 prior to advancing implant 262 within the body of the patient.

Segment 268 is typically coupled to portion of sleeve 26 designated for implantation along the annulus of the valve at posterior leaflet 14. Alternatively or additionally, segment 268 is coupled to a portion of the sleeve designated for implantation in a vicinity of one or both trigones 2 and 4. The coupling of segment 268 to the portion of sleeve 26 defines contraction-restricted portion 52 of structure 262, while the remaining portions of sleeve 26 not coupled to segment 268 define contraction-facilitated portions 53a and 53b of structure 262. In general, the techniques described hereinabove with respect to contraction-restricting element 200, with reference to FIGS. 10A-12, may be applied to segment 268, mutatis mutandis.

Implant structure 262 is generally similar to implant structure 22, as described hereinabove with reference to FIGS. 1, 2, 3A-F, 4-7, 8A-C, and 9, with the exception that contraction-restricting element 200 is coupled to the outer surface of sleeve 26, and implant structure 262 typically does not comprise crimping element(s) 32 or 34. Structure 262 is typically implanted along the annulus in a manner as described hereinabove with reference to FIGS. 2, 3A-C, 8A-C, and 9, with regard to the implantation of implant structure 22 along the annulus of the mitral valve.

Following the implantation of structure 262 along the annulus, portions of implant structure 262 are contracted using contracting mechanism 40, as described hereinabove. During the ongoing contraction of structure 262 responsively to the actuation of contracting mechanism 40, contraction-facilitated portions 53a and 53b are contracted, while contraction-restricting element 200 restricts longitudinal contraction of contraction-restricted portion 52, but facilitates radial movement of portion 52 toward the center of the valve (i.e., in the direction as indicated by the arrows). This radial movement of portion 52 brings leaflet 14 toward leaflet 12.

Following the contracting of structure 262 by mechanism 40, the opening at proximal end 49 of implant structure 262 may be closed, such as by closure mechanism 290. For some applications, closure mechanism 290 comprises closure mechanism 290, as described hereinabove with reference to FIGS. 1 and 3D-E. For some applications, closure mechanism 290 comprises closure mechanism 290, as will be described hereinbelow with reference to FIGS. 14A-B.

It is to be noted that although contraction-restricting segment 268 is shown in FIG. 13 as comprising a tubular element, for some applications, a different element, e.g., a suture, is used to define contraction-restricted portion 52 of implant structure 262. For example, coiled element 240 may be placed inside sleeve 26. One or more contraction-restricting elements (e.g., a suture, a staple, a ratchet mechanism, and/or a bracket) are placed around portions of the coiled element, in order to decrease the pitch of the coiled element at the portions, thereby reducing the contractibility of the portions.

For some applications, a healthcare professional places the contraction-restricting element around given portions of the coiled element intra-procedurally, the portions of the coiled element corresponding to respective portions of a subject's mitral annulus. For example, subsequent to determining the size of the subject's mitral valve, and before placing the implant structure inside the patient's body, the healthcare professional may place contraction-restricting element around given portions of the coiled element, in order to reduce the contractibility of the portions. For some applications, the healthcare professional applies sutures to the coiled element while the element is disposed inside a sizer. For some applications, the sizer is used to guide the suturing and to prevent the healthcare professional from placing a suture through contracting member 30 (shown in FIG. 1, for example).

FIGS. 14A-B show a system 280 comprising an implant structure 281 and closure mechanism 290 comprising self-closing strips 282*a* and 282*b*, in accordance with some applications of the present invention. Implant structure 281 is generally similar to implant structure 22, as described hereinabove with reference to FIGS. 1, 2, 3A-F, 4-7, 8A-C, and 9, with the exception that closure mechanism 290 at proximal end 49 of structure 281 comprises strips 282*a* and 282*b* and does not comprise crimping element(s) 32 or 34.

Strips 282*a* and 282*b* are typically coupled to (e.g., by being threaded through) portions of proximal end 49 of structure 281 in the vicinity of opening 25. Strips 282*a* and 282*b* define generally arcuate elements which comprise a flexible material (e.g., nitinol). Strips 282*a* and 282*b* have a tendency to close and assume the configuration shown in FIG. 14B. Strips 282*a* and 282*b* are opened from their closed state when a tool (e.g., such as manipulator 60, as shown, and described hereinabove with reference to FIGS. 1, 2, 3A-C, 8A-C, 9, or delivery tube 232 described hereinabove with reference to FIGS. 10A-E and 11A-D) is advanced within the lumen of sleeve 26 (as shown in FIG. 14A). Once the tool is removed from within the lumen, strips 282*a* and 282*b* assume their biased state thereby closing opening 25 at proximal end 49 of structure 281. Thus, strips 282 are automatically-activatable when the delivery tool is removed from the lumen of sleeve 26.

Strips 282*a* and 282*b* are coupled to respective strings 284 which couple strips 282*a* and 282*b* to sleeve 26. Strings 284 are crimped together by a crimp 286.

As shown in FIG. 14A, manipulator 60 is advanceable within the lumen of sleeve 26 so as to facilitate anchoring of structure 281 using anchors 38, in a manner as described hereinabove with reference to FIGS. 2, 3A-C, 8A-C, and 9, with regard to the implantation of implant structure 22 along the annulus of the mitral valve. Following the anchoring, contracting mechanism 40 is actuated in order to adjust a dimension of structure 281. As described hereinabove, contracting mechanism 40 adjusts a tension of contracting member 30 coupled thereto. Contracting mechanism 40 and contracting member 30 are coupled to sleeve 26, in a manner as described hereinabove with reference to FIG. 1. Since contracting member 30 is threaded through sleeve 26, as shown, the adjusting of the tension of contracting mechanism 30 adjusts the dimension of sleeve 26 and thereby, of implant structure 281. Following the adjusting, manipulator 60 is then removed from the body of the patient, allowing strips 282*a* and 282*b* to close around opening 25, and structure 281 remains within the heart. It is to be noted that structure 281 may comprise the stiffening element described hereinabove with reference to FIG. 1.

Reference is made to FIGS. 15A-C, which are schematics illustrations of an exemplary configuration of one of anchors 38, in accordance with an application of the present invention. For some applications, each of tissue anchors 38 comprises a helical tissue coupling element 400, and a tool-engaging head 402, fixed to one end of the tissue coupling element (the proximal end of the tissue coupling element, opposite the distal end that first penetrates the tissue). Anchor 38 comprises a hard material, such as metal, e.g., steel, Nitinol, or stainless steel SS316LVM. Anchor 38 may be manufactured from a single piece of material, or coupling element 400 and tool-engaging head 402 may be manufactured from separate pieces of material and fixed together.

Typically, helical tissue coupling element 400 has an inner diameter D3 of at least 1.5 mm, no more than 2.5 mm, and/or between 1.5 and 2.5 mm, e.g., 1.8 mm, along an entire length thereof along a central longitudinal axis 410 of the anchor (although the inner diameter is shown as being constant along the entire length of coupling element 400, the inner diameter optionally varies along the length of the coupling element). An outer diameter D4 of helical tissue coupling element 400 may be, for example, at least 2.4 mm, no more than 5 mm, and/or between 2.4 and 5 mm, e.g., 2.4 mm.

Tool-engaging head 402 is shaped so as to define an engaging opening 412 that passes entirely through the tool-engaging head along axis 410. The engaging opening is typically at least partially non-circular, such as in order to engage a rotating deployment element of a deployment tool. For example, as shown in FIGS. 15A-C, engaging opening 412 may be shaped so as to define a proximal non-circular internal engaging surface 420, and a distal circular non-engaging surface 422. Proximal engaging surface 420 is shaped to engage a rotating deployment element, such that rotation of the deployment element rotates tool-engaging head 402 and anchor 38. For example, proximal engaging surface 420 may be rectangular (e.g., square), teethed (e.g., defining a plurality of squares with which the rotating element can engage), star-shaped, polygonal (e.g., octagonal), or any other appropriate non-circular shape.

A portion of the deployment element may pass partially or completely through distal non-engaging surface 422, without engaging this surface. The non-engaging surface may serve as a shoulder, which pushes against the tissue, providing resistance when the anchor has been sufficiently screwed into the tissue. Optionally, the deployment element does not pass entirely through distal non-engaging surface 422, such that the deployment element does not press against or into the tissue. Alternatively, the deployment element may protrude slightly from the distal non-engaging surface 422, when no force is applied to the deployment element by the tissue. Optionally, when the anchor is pressed against the tissue, inner spaces in the tool-engagement head 402 of the anchor allow the deployment element to sink into the anchor, and not press against the tissue. Engaging opening 412 typically has a cross-sectional area (perpendicular to axis 410) of at least 0.8 mm2, such as at least 1.2 mm2.

For some applications, a proximal-most portion 424 of helical tissue coupling element 400, at the end which is fixed to tool-engaging head 402, is generally straight and oriented generally parallel to axis 410, i.e., at angle of between 0 and 15 degrees with the axis, such as 0 degrees. Proximal-most portion 424 typically has a length of between 0.5 and 2 mm, such as about 1 mm.

The outer perimeter of tool-engaging head 402 is typically circular, and an outer diameter D5 of tool-engaging head 402 may be, for example, at least 2 mm, no more than 7 mm, and/or between 2 and 7 mm, such as between 2.5 and 5 mm, e.g., 2.4 mm, 2.5 mm, or 3 mm.

The outer diameter of anchor 38 may be, for example, at least 2 mm, no more than 7 mm, and/or between 2 and 7 mm, such as between 2.5 and 5 mm. The entire length of anchor 38, measured along axis 410, is typically at least 2.5 mm, no greater than 10 mm, and/or between 2.5 and 10 mm, such as between 3 and 4.5 mm. A length L1 of tissue coupling element 400, measured along axis 410, may be at least 2.5 mm, no greater than 10 mm, and/or between 2.5 and 10 mm, such as between 3 and 4.5 mm. Typically, helical tissue coupling element 400 has between 3 and 5 turns.

The proximal end of tissue coupling element 400 is typically fixed to tool-engaging head 402 near the outer perimeter of the tool-engaging head, such that the tissue coupling element does not block engaging opening 412. For example, as labeled in the top-view of the anchor in FIG. 15C, the tissue coupling element may be fixed to the tool-engaging head such that one or more of the following dimension characterize the anchor:
- a distance D7 between (a) a center 431 of the proximal end of tissue coupling element 400 and (b) an outer perimeter of tool-engaging head 402 is no more than 20% of a width D5 of tool-engaging head 402 (the width is a diameter for applications in which the head is circular), such as no more than 10% of width D3. For example, distance D7 may be between 0.1 and 0.3 mm, e.g., 0.2 mm;
- a distance D8 between (a) a most radially-inward portion 428 of the proximal end of tissue coupling element 200 (i.e., the portion of the proximal end that is closest to central longitudinal axis 410 of the anchor) and (b) the outer perimeter of tool-engaging head 202 is no more than 40% of width D5 of tool-engaging head 202 (the width is a diameter for applications in which the head is circular), such as no more than 30% of width D5, or no more than 20% of width D5. For example, distance D8 may be between 0.3 and 0.5 mm, e.g., 0.4 mm; and/or
- a distance between (a) a most radially-outward portion 430 of the proximal end of tissue coupling element 400 (i.e., the portion of the proximal end that is furthest from central longitudinal axis 410 of the anchor) and (b) the outer perimeter of tool-engaging head 402 is no more than 10% of width D5 of tool-engaging head 402 (the width is a diameter for applications in which the head is circular), such as no more than 5% of width D5, e.g., 0. For example, the distance may be between 0 and 0.1 mm, e.g., 0 mm.

Anchor 38, including both helical tissue coupling element 400 and tool-engaging head 402, is thus shaped so as to provide a channel along the entire length of the anchor, through which a flexible inner shaft can pass, and through which a rotating deployment element can pass when in its radially-compressed state. More generally, as shown in FIG. 15B, the channel is sized and shaped such that a right circular cylinder 432 could be placed within the channel, coaxial with anchor 38 (i.e., the axis of the cylinder coincides with central longitudinal axis 410 of anchor 38), and along the entire length of the tissue anchor, the cylinder having a diameter D6 of at least 1 mm, such as at least 2 mm. It is to be understood that cylinder 432 is an abstract geometric shape, rather than an element of an embodiment of the invention, and, as such, is perfectly cylindrical, i.e., is not shaped so as to define any grooves or other surface or internal anomalies. No portion of anchor 38 intersects central longitudinal axis 410.

Reference is now made to FIGS. 1-15C. Implant structures 22, 222, 262, 281, and 300 may be advanced toward annulus 140 in any suitable procedure, e.g., a transcatheter procedure, a percutaneous procedure, a minimally invasive procedure, or an open heart procedure (in which case one or more elements of systems 20, 220, 250, 260, and 280 are typically rigid). Regardless of the approach, the procedure typically includes the techniques described hereinabove with reference to FIGS. 8A-C and 9.

It is to be noted that the positioning of contraction-restricting element(s) 200 along implant structures 22, 222, 262, 281, and 300 is shown by way of illustration and not limitation, and that contraction-restricting element(s) 200 (and any amount thereof) may be placed anywhere along implant structures 22, 222, 262, 281, and 300.

For some applications, following initial contraction of implant structures 22, 222, 262, and 281 during the implantation procedure, implant structures 22, 222, 262, and 281 may be further contracted or relaxed at a later time after the initial implantation, such as between several weeks and several months after the initial implantation. Using real-time monitoring, tactile feedback and optionally in combination with fluoroscopic imaging, a rotation tool or anchor driver 68 of deployment manipulator 60 is reintroduced into the heart and used to contract or relax implant structures 22, 222, 262, and 281.

Although implant structures 22, 222, 262, and 281 has been described hereinabove as comprising a partial annuloplasty ring, for some applications of the present invention, implant structure 22 instead comprises a full annuloplasty ring. Implant structures 22, 222, 262, and 281 may comprise an annular portion of a structure, a ring, or a partial ring, which facilitate coupling thereto of a prosthetic valve which replaces the native atrioventricular valve. Typically, implant structures 22, 222, 262, and 281 function to treat (e.g., facilitate repair or replacement of) the native atrioventricular valve of the patient.

For some applications of the present invention, systems 20, 220, 250, 260, and 280 are used to treat an atrioventricular valve other than the mitral valve, i.e., the tricuspid valve. For these applications, implant structures 22, 222, 262, and 281, and other components of systems 20, 220, 250, 260, and 280 described hereinabove as being placed in the left atrium are instead placed in the right atrium. Although implant structures 22, 222, 262, and 281 are described hereinabove as being placed in an atrium, for some application implant structures 22, 222, 262, and 281 are instead placed in either the left or right ventricle.

Features of implant structures 22, 222, 262, 281, and 300 described with reference to respective figures are not limited to the prostheses shown in those figures. Rather, features of the implant structures shown in any of the figures could be used in combination with any of the other features described herein, mutatis mutandis. Examples of the features that may be combined with each other include, but are not limited to:
- crimping elements 32 and 34,
- flap 27, 30
- stiffening elements 36
- coiled element 240,
- contraction-restricting segment 268, and
- self-closing strips 282a and 282b.

For some applications, the scope of the present invention includes embodiments described in the following applications, which are incorporated herein by reference. In an embodiment, techniques and apparatus described in one or more of the following applications are combined with techniques and apparatus described herein:

PCT Publication WO 06/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed Feb. 16, 2007;

U.S. Provisional Patent Application 61/001,013 to Gross et al., entitled, "Segmented ring placement," filed Oct. 29, 2007;

PCT Publication WO 08/068,756 to Gross et al., entitled, "Segmented ring placement," filed Dec. 5, 2007;

U.S. patent application Ser. No. 11/950,930 to Gross et al., entitled, "Segmented ring placement," filed Dec. 5, 2007, which published as US 2008/0262609;

U.S. patent application Ser. No. 12/435,291 to Maisano et al., entitled, "Adjustable repair chords and spool mechanism therefor," filed on May 4, 2009, which published as US 2010/0161041;

U.S. patent application Ser. No. 12/437,103 to Zipory et al., entitled, "Annuloplasty ring with intra-ring anchoring," filed on May 7, 2009, which published as US 2010/0286767;

PCT Publication WO 10/004,546 to Gross et al., entitled, "Annuloplasty devices and methods of delivery therefor," filed on Jun. 15, 2009;

U.S. patent application Ser. No. 12/548,991 to Maisano et al., entitled, "Implantation of repair chords in the heart," filed on Sep. 21, 2009, which published as US 2010/0161042;

PCT Publication WO 10/073,246 to Cabiri et al., entitled, "Adjustable annuloplasty devices and mechanisms therefor," filed Dec. 22, 2009;

U.S. patent application Ser. No. 12/706,868 to Miller et al., entitled, "Actively-engageable movement-restriction mechanism for use with an annuloplasty structure," filed Feb. 17, 2010, which published as US 2010/0211166;

PCT Publication WO/2010/128502 to Maisano et al., entitled, "Implantation of repair chords in the heart," filed May 4, 2010;

U.S. patent application Ser. No. 12/608,316 to Miller et al., entitled, "Tissue anchor for annuloplasty ring," filed on Oct. 29, 2009, which published as US Patent Application Publication 2011/0106247

U.S. patent application Ser. No. 12/689,693 to Hammer et al., entitled, "Deployment techniques for annuloplasty ring," filed on Jan. 19, 2010, which published as US Patent Application Publication 2010/0280605; and/or PCT Publication WO/2010/128503 to Zipory et al., entitled, "Deployment techniques for annuloplasty ring and overwire rotation tool," filed May 4, 2010.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
an annuloplasty structure configured for implantation along an annulus of an atrioventricular valve of a heart of a subject, the structure comprising:
a sleeve defining a lumen therethrough;
an elongate coiled element disposed entirely within the lumen of the sleeve, the coiled element comprising:
at least one first coiled portion having coils that are flexible and longitudinally compressible; and
at least one second coiled portion in series with the first coiled portion, the second coiled portion having coils that are flexible and less longitudinally compressible than the coils of the first coiled portion;
a contracting member disposed within a lumen of the coiled element, the contracting member being slidable through the first and second coiled portions of the coiled element in order to adjust a perimeter of the annuloplasty structure; and
a contracting mechanism coupled to a portion of the contracting member, the contracting mechanism being:
attached to the coiled element at the second coiled portion, and
configured to adjust the perimeter of the annuloplasty structure by applying a force to the contracting member, wherein a length of the second coiled portion is 10-50 mm.

2. The apparatus according to claim 1, wherein the second coiled portion comprises first and second second-coiled-portion-elements, wherein the contracting mechanism is attached to the coiled element at the second coiled portion between the first and second second-coiled-portion-elements, and wherein the length of the second coiled portion comprises a combined length of the first and second second-coiled-portion-elements.

3. The apparatus according to claim 1, wherein a radius of curvature at a center of the first coiled portion is smaller than a radius of curvature at a center of the second coiled portion, when no external force is applied to the annuloplasty structure.

4. A method, comprising:
positioning an annuloplasty structure along an annulus of an atrioventricular valve of a subject, the annuloplasty structure including:
a sleeve defining a lumen therethrough, and
an elongate coiled element disposed entirely within the lumen of the sleeve, the coiled element including:
at least one first coiled portion having coils that are flexible and longitudinally compressible; and
at least one second coiled portion in series with the first coiled portion, the second coiled portion having coils that are flexible and less longitudinally compressible than the coils of the first coiled portion and having a length of 10-50 mm;
a contracting member disposed within a lumen of the coiled element, the contracting member being slidable through the first and second coiled portions of the coiled element in order to adjust a perimeter of the annuloplasty structure; and
a contracting mechanism coupled to a portion of the contracting member, the contracting mechanism being:
attached to the coiled element at the second coiled portion, and
configured to adjust the perimeter of the annuloplasty structure by applying a force to the contracting member;
fastening the annuloplasty structure to the annulus; and
adjusting the perimeter of the annuloplasty structure by applying the force to the contracting member and compressing the first coiled portion of the coiled element.

5. Apparatus, comprising:
an annuloplasty structure configured for implantation along an annulus of an atrioventricular valve of a heart of a subject and shaped so as to define a substantially "D"-shaped configuration having a straight portion and a curved portion, the structure comprising:
a sleeve defining a lumen therethrough;
an elongate coiled element disposed entirely within the lumen of the sleeve, the coiled element comprising:

at least one first coiled portion having coils that are flexible and longitudinally compressible, the curved portion of the annuloplasty structure comprising the first coiled portion; and at least one second coiled portion in series with the first coiled portion, the second coiled portion having coils that are flexible and less longitudinally compressible than the coils of the first coiled portion, the straight portion of the annuloplasty structure comprising the second coiled portion;

a contracting member disposed within a lumen of the coiled element, the contracting member being slidable through the first and second coiled portions of the coiled element in order to adjust a perimeter of the annuloplasty structure; and a contracting mechanism coupled to a portion of the contracting member, the contracting mechanism being:

attached to the coiled element at the straight portion of the annuloplasty structure, and configured to adjust the perimeter of the annuloplasty structure by applying a force to the contracting member.

6. The apparatus according to claim 5, wherein the annuloplasty structure comprises an annuloplasty ring.

7. The apparatus according to claim 5, further comprising a contraction-restricting element configured to be coupled to the second coiled portion of the coiled element, wherein the second coiled portion is configured to be flexible and less longitudinally compressible than the first coiled portion at least in part by virtue of the contraction-restricting element being coupled thereto.

8. The apparatus according to claim 7, wherein the contraction-restricting element comprises an element selected from the group consisting of: a suture, a staple, a ratchet mechanism, and a bracket.

9. The apparatus according to claim 5, wherein the valve includes a native mitral valve of the subject, and wherein the structure is configured for implantation along a native annulus of the native mitral valve in a manner in which at least the first coiled portion of the annuloplasty structure is disposed along a portion of the annulus at a posterior leaflet of the valve.

10. The apparatus according to claim 9, wherein the second coiled portion is configured to restrict contraction of the second coiled portion while facilitating radial movement of the second coiled portion of the annuloplasty structure.

11. The apparatus according to claim 5,
wherein the atrioventricular valve includes a mitral valve,
wherein the coiled element comprises a plurality of second-coiled-portion-elements, and
wherein the annuloplasty structure is configured for implantation along the annulus in a manner in which:
a first second-coiled-portion-element of the second-coiled-portion-elements is configured to be coupled to the annulus in a vicinity of a left trigone adjacent to the mitral valve, and
a second second-coiled-portion-element of the second-coiled-portion-elements is configured to be coupled to the annulus in a vicinity of a right trigone adjacent to the mitral valve.

12. The apparatus according to claim 11, wherein a combined length of the first and second second-coiled-portion-elements is 10-50 mm.

13. The apparatus according to claim 5, wherein:
the sleeve has first and second end portions and a body portion that is between the first and second end portions; and the contracting member extends along the body portion between the first and second end portions of the sleeve, the contracting member having first and second end portions, the first end portion of the contracting member being coupled to the sleeve in a vicinity of the first end portion thereof, and the second end portion of the contracting member being coupled to the sleeve in a vicinity of the second end portion thereof.

14. The apparatus according to claim 13, wherein the annuloplasty structure is configured to be implanted along an annulus of a mitral valve of the subject in a manner in which the annuloplasty structure is formed into at least a portion of an annuloplasty ring.

15. The apparatus according to claim 5, wherein the coiled element is longitudinally slidable within the lumen of the sleeve.

16. The apparatus according to claim 5, wherein the contracting member is threaded one or more times through the sleeve.

17. The apparatus according to claim 5, wherein a radius of curvature at a center of the first coiled portion is smaller than a radius of curvature at a center of the second coiled portion, when no external force is applied to the annuloplasty structure.

18. A method, comprising:
positioning along an annulus of an atrioventricular valve of a subject an annuloplasty structure shaped so as to define a substantially "D"-shaped configuration having a straight portion and a curved portion, the annuloplasty structure including:
a sleeve defining a lumen therethrough, and
an elongate coiled element disposed entirely within the lumen of the sleeve, the coiled element including:
at least one first coiled portion having coils that are flexible and longitudinally compressible, the curved portion of the annuloplasty structure comprising the first coiled portion; and
at least one second coiled portion in series with the first coiled portion, the second coiled portion having coils that are flexible and less longitudinally compressible than the coils of the first coiled portion, the straight portion of the annuloplasty structure comprising the second coiled portion;
a contracting member disposed within a lumen of the coiled element, the contracting member being slidable through the first and second coiled portions of the coiled element in order to adjust a perimeter of the annuloplasty structure; and
a contracting mechanism coupled to a portion of the contracting member, the contracting mechanism being:
attached to the coiled element at the straight portion of the annuloplasty structure, and
configured to adjust the perimeter of the annuloplasty structure by applying a force to the contracting member;
fastening the annuloplasty structure to the annulus; and
adjusting the perimeter of the annuloplasty structure by applying the force to the contracting member and compressing the first coiled portion of the coiled element.

19. The method according to claim 18, further comprising coupling a contraction-restricting element to an outer surface of the annuloplasty structure.

20. The method according to claim 18, wherein adjusting comprises restricting contraction of the second coiled portion of the annuloplasty structure while facilitating radial movement of the second coiled portion of the annuloplasty structure.

21. The method according to claim 18, wherein positioning the annuloplasty structure along the annulus of the atrioventricular valve comprises positioning the annuloplasty structure in a manner in which the curved portion of the annuloplasty structure is disposed along a portion of the annulus at a posterior leaflet of the valve, and the straight portion is disposed along a portion of the annulus at an anterior leaflet of the valve.

* * * * *